US008193200B2

(12) United States Patent
Sitaraman et al.

(10) Patent No.: US 8,193,200 B2
(45) Date of Patent: Jun. 5, 2012

(54) ANTAGONISTS OF A2B ADENOSINE RECEPTORS FOR TREATMENT OF INFLAMMATORY BOWEL DISEASE

(75) Inventors: Shanthi V. Sitaraman, Atlanta, GA (US); Joel M. Linden, Charlottesville, VA (US); Guoquan Wang, Charlottesville, VA (US); Robert Douglas Thompson, Charlottesville, VA (US); Jayson M. Rieger, Charlottesville, VA (US)

(73) Assignees: University of Virginia Patent Foundation, Charlottesville, VA (US); Emory University, Atlanta, GA (US)

( * ) Notice: Subject to any disclaimer, the term of this patent is extended or adjusted under 35 U.S.C. 154(b) by 403 days.

(21) Appl. No.: 11/982,817

(22) Filed: Nov. 5, 2007

(65) Prior Publication Data

US 2008/0176845 A1     Jul. 24, 2008

Related U.S. Application Data

(60) Provisional application No. 60/878,613, filed on Jan. 4, 2007.

(51) Int. Cl.
*A61K 31/522* (2006.01)
*A61K 31/496* (2006.01)
(52) U.S. Cl. .............................. 514/263.22; 514/252.16
(58) Field of Classification Search .......................... None
See application file for complete search history.

(56) References Cited

U.S. PATENT DOCUMENTS

| | | | |
|---|---|---|---|
| 4,452,788 A | 6/1984 | Bristol et al. | |
| 4,612,315 A | 9/1986 | Jacobson et al. | |
| 4,696,932 A | 9/1987 | Jacobson et al. | |
| 4,968,672 A | 11/1990 | Jacobson et al. | |
| 5,300,298 A | 4/1994 | LaNoue | |
| 5,443,836 A | 8/1995 | Downey et al. | |
| 5,446,046 A | 8/1995 | Belardinelli et al. | |
| 6,437,124 B1 | 8/2002 | Daluge et al. | |
| 7,342,006 B2 * | 3/2008 | Wang et al. | 514/211.08 |
| 2007/0059740 A1 | 3/2007 | Linden | |

FOREIGN PATENT DOCUMENTS

| | | |
|---|---|---|
| EP | 0203721 A2 | 12/1986 |
| EP | 0374808 A2 | 6/1990 |
| WO | WO-9000056 | 1/1990 |
| WO | WO-9000056 A1 | 1/1990 |
| WO | WO-9511681 A1 | 5/1995 |
| WO | WO-9942093 A2 | 8/1999 |

OTHER PUBLICATIONS

Asamoah et al., Gastroenterology, (Apr. 2005), 128(4), Suppl. 2, pp. A654.*
Sitaraman et al., Adenosine Receptors (2007), pp. 131-144.*
Kolachala, V. , et al., "TNF-alpha Upregulates Adenosine 2b (A2b) Receptor Expression and Signalling in Intestinal Epithlial Cells: A Basis for A2bR Overexpression in Colitis", *Cell. Mol. Life Sci.*, 62., (2005),2647-2657.
Sitaraman, S. V., et al., "Neutrophil-Epithelial Crosstalk at the Intestinal Lumenal Surface Mediated by Reciprocal Secretion of Adenosine and IL-6", *The Journal of Clinical Investigation*, 107(7), (2001),861-869.
Sitaraman, S. V., et al., "The Adenosine 2b Receptor Is Recruited to the Plasma Membrane and Associates With E3KARP and Ezrin Upon Agonist Stimulation", *The Journal of Biological Chemistry*, 277(36), (2002),33188-33195.
"International Application Serial No. PCT/US00/15233, International Search Report mailed Nov. 28, 2000", 8 pgs.
"International Application Serial No. PCT/US00/15233, Response filed Jun. 19, 2001 to Written Opinion mailed Mar. 19, 2001", 35 pgs.
"International Application Serial No. PCT/US00/15233, Written Opinion mailed Mar. 19, 2001", 7 pgs.
"International Application Serial No. PCT/US99/04009, International Search Report mailed Sep. 13, 1999", 10 pgs.
"International Application Serial No. PCT/US99/04009, Written Opinion mailed Dec. 29, 1999", 10 pgs.
"The gene card for acpi", [retrieved Apr. 2, 2009]. Retrieved from the Internet: <URL: http://www.genecards.org/cgi-bin/carddisp.pl?gene=ACP1&search=acp 1>, 13 pgs.
Alexander, S. P., et al., "Characterization of the human brain putative A2B adenosine receptor expressed in Chinese hamster ovary (CHO. A2B4) cells", British Journal of Pharmacology, 119(6), (Nov. 1996), 1286-1290.
Auchampach, John A., et al., "Canine Mast Cell Adenosine Receptors: Cloning and Expression of the A3 Receptor and Evidence that Degranulation is Mediated by the A2B Receptor", Molecular Pharmacology, 52 (5), (Nov. 1997), 846-860.
Barcz, E., et al., "The influence of theobromine on angiogenic activity and proangiogenic cytokines production of human ovarian cancer cells", Oncology Reports, 5 (2), (Mar.-Apr. 1998), 517-520.
Barnes, P. J., et al., "Theophylline in the Management of Asthma: Time for Reappraisal?", European Respiratory Journal, 7, (1994), 579-591.
Bjorck, T, et al., "Isolated Bronchi from Asthmatics are Hyperresponsive to Adenosine, which Apparently Acts Indirectly by Liberation of Leukotrienes and Histamine", American Review of Respiratory Disease, 145, (1992), 1087-1091.
Bjork, T., et al., "Isolated Bronchi from Asthmatics are Hyperresponsive to Adenosine, which Apparently Acts Indirectly by Liberation of Leukotrienes and Histamine", Am. Rev. Respir. Dis, 145, , (1992), pp. 1087-1091.
Botitni, N., et al., "Genotypes of cytosolic low molecular weight protein tyrosine phosphate correlate with age at onset of type I diabeties in a sex specific manner", Metabolism, 51(4), (2002), 419-422.
Brackett, L. E., et al., "Functional Characterization of the A2b Adenosine Receptor in NIH 3T3 Fibroblasts", Biochemical Pharmacology, 47(5), (1994), 801-814.
Bruns, R. F., "Adenosine Antagonism by Purines, Pteridines and Benzopteridines in Human Fibroblasts", Biochemical Pharmacology, 30, (1981), pp. 325-333.

(Continued)

*Primary Examiner* — Phyllis G. Spivack
(74) *Attorney, Agent, or Firm* — Schwegman, Lundberg & Woesnner, P.A.

(57) ABSTRACT

The present invention relates to method for treating inflammatory bowel disease that includes administration of an effective amount of an antagonist of $A_{2B}$ adenosine receptors (ARs).

2 Claims, 11 Drawing Sheets

OTHER PUBLICATIONS

Figure 1:
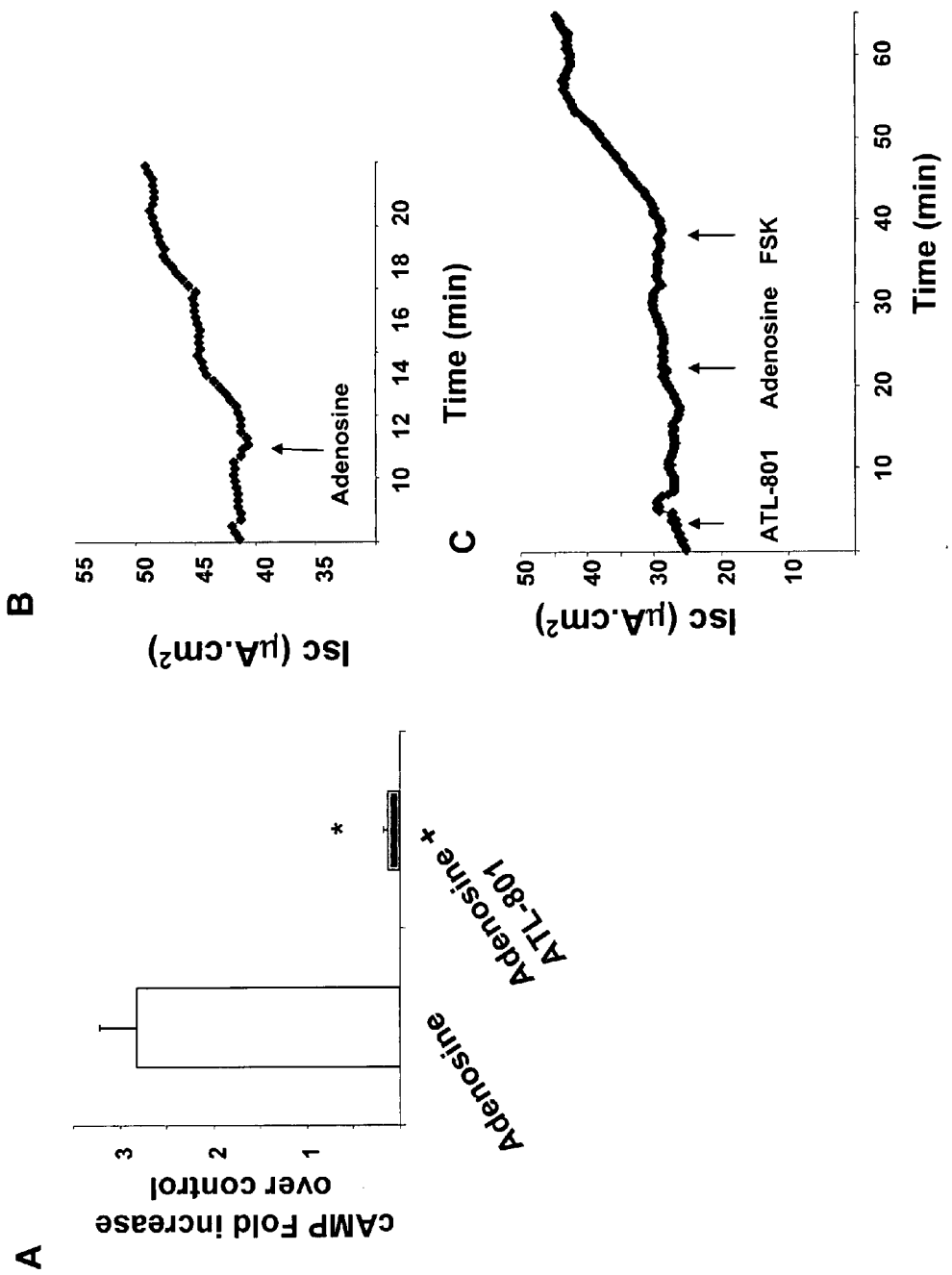

Bruns, R. F., et al., "Adenosine receptor binding: Structure-activity analysis generates extremely potent xanthine antagonists", Proceedings of the National Academy of Sciences, 80 (7), , (Apr. 1983), pp. 2077-2080.

Bruns, R. F., et al., "Binding of the A1-selective adenosine antagonist 8-cyclopentyl-1,3-dipropylxanthine to rat brain menbranes", Naunyn-Schmiedeberg's Archives of Pharmacology, (1987), 59-63.

Chapman, K. R., et al., "Long-Term Xanthine Therapy of Asthma—Enprofylline and Theophylline Compared", Chest, 106 (5), (Nov. 1994), 1407-1413.

Clancy, J. P., et al., "Adenosine and its nucleotides activate wild-type and R117H CFTR through an A2B receptor-coupled pathway", American Journal of Physiology, 276 (Issue 2), Cell Physiology, (Feb. 1999), pp. C361-C369.

Clarke, H., et al., "The Protective Effects of Intravenous Theophylline and Enprofylline against Histamine- and Adenosine 5'-Monophosphate-provoked Bronchoconstriction : Implications for the Mechanisms of Action of Xanthine Derivatives in Asthma", Pulmonary Pharmacology, 2, (1989), 147-154.

Cooper, J., et al., "An endogenous A2B adenosine receptor coupled to cyclic AMP generation in human embryonic kidney (HEK 293) cells", British Journal of Pharmacology, 122, (1997), pp. 546-550.

Crist, G. H., et al., "Tissue-Specific effects of in vivo adenosine receptor blockade on glucose uptake in Zucker rats", The FASEB Journal, 12, (Oct. 1998), pp. 1301-1308.

Cristalli, G., et al., "Characterization of Potent Ligands at Human Recombinant Adenosine Receptors", Drug Development Research, 45, Research Overview, (1998), 176-181.

Cushley, M. J., et al., "Adenosine-induced bronchoconstriction in asthma: Role of mast cell-mediator release", J. Allergy Clin. Immunol., 75 (2), (Feb. 1985), 272-278.

Daly, J. W., et al., "Molecular Probes for Adenosine Receptors", In: The Nervous System, J.A. Ribeiro, ed., Taylor & Francis, London, (1989), 41-52.

Daly, J. W., et al., "Subclasses of Adenosine Receptors in the Central Nervous System: Interaction with Caffeine and Related Methylxanthines", Cellular and Molecular Neurobiology, 3 (1), (1983), 69-80.

De Zwart, M., et al., "A Functional Screening of Adenosine Analogues at the Adenosine A2B Receptor: A Search for Potent Agonists", Nucleosides & Nucleotides, 17(6), (1998), 969-985.

De Zwart, M., et al., "Potent Antagonists for the Adenosine A2B Receptor. II. Triazolotriazines with High Affinity", Ferrara Abstracts, Abstract No. 107, (1998), 1 pg.

Drazen, J. M., et al., "Treatment of Asthma with Drugs Modifying the Leukotriene Pathway", Drug Therapy, Review Article, 340 (3), (Jan. 21, 1999), 197-206.

Felgner, P. L., et al., "Lipofection: A highly efficient, lipid-mediated DNA-transfection procedure", Proc. Natl. Acad. Sci. USA, 84, (Nov. 1987), 7413-7417.

Feoktistov, I., et al., "Adenosine A2b Receptors Evoke Interleukin-8 Secretion in Human Mast Cells—An Enprofylline-Sensitive Mechanism with Implications for Asthma", The Journal of Clinical Investigation, 96, (1995), 1979-1986.

Feoktistov, I., et al., "Role of p38 Mitogen-Activated Protein Kinase and Extracellular Signal-Regulated Protein Kinase Kinase in Adenosine A2B Receptor-Mediated Interleukin-8 Production in Human Mast Cells", Molecular Pharmacology, 55, (1999), 726-734.

Forsythe, P., et al., "Adenosine, mast cells and asthma", Inflammation Research, 48, (1999), 301-307.

Francis, J. E., "Highly Selective Adenosine A2 Receptor Agonists in a Series of N-Alkylated 2-Aminoadenosines", Journal of Medicinal Chemistry, 34 (8), (1991), 2570-2579.

Fredholm, B. B., et al., "Actions of Caffeine in the Brain with Special Reference to Factors That Contribute to Its Widespread Use", Pharmacological Reviews, 51 (1), (1999), 83-133.

Jacobson, K. A., et al., "1,3-Dialkylxanthine Derivatives Having High Potency as Antagonists at Human A2b Adenosine Receptors", Drug Development Research, 47 (1),, (1999), 45-53.

Jacobson, K. A., et al., "8-Substituted Xanthines as Antagonists at A1- and A2-Adenosine Receptors", Biochemical Pharmacology, 37(19), (1988), 3653-3661.

Jacobson, K. A., et al., "A Functionalized Cogener Approach to Adenosine Receptor Antagonists: Amino Acid Conjugates of 1,3-Dipropylxanthine", Molecular Pharmacology, 29, (1985), 126-132.

Jacobson, K. A., et al., "Adenosine Receptors: Pharmacology, structure-activity relationships and therapeutic potential", Journal of Medicinal Chemistry., 35(3), (Feb. 7, 1992), 407-422.

Jacobson, K. A., et al., "Chapter 6—Development of Selective Purinoceptor Agonists and Antagonists", In: Purinergic Approaches in Experimental Therapeutics, Edited by K.A. Jacobson et al., Wiley-Liss, Inc., (1997), 101-128.

Jacobson, K. A., et al., "Electrophilic Derivatives of Purines as Irreversible Inhibitors of A1 Adenosine Receptors", Journal of Medicinal Chemistry, 32(5), (1989), 1043-1051.

Jacobson, K. A., et al., "Functionalized Congeners of 1,3-Dialkylxanthines: Preparation of Analogues with High Affinity for Adenosine Receptors", Journal of Medicinal Chemistry, 28(9), (Sep. 1985), 1334-1340.

Jacobson, K. A., et al., "Probing the adenosine receptor with adenosine and xanthine biotin conjugates", Federation of European Biomedical Societies, 184(1), (May 1985), 30-35.

Jacobson, K. A., et al., "Stimulation by Alkylxanthines of Chloride Efflux in CFPAC-1 Cells Does Not Involve A1 Adenosine Receptors", Biochemistry, 34(28), (1995), 9088-9094.

Jacobson, K. A., et al., "Structure-Activity Relationships of 8-Styrylxanthines as A2-Selective Adenosine Antagonists", Journal of Medicinal Chemistry, 36(10), (1993), 1333-1342.

Jacobson, K. A., et al., "Sulfur-Containing 1,3-Dialkylxanthine Derivatives as Selective Antagonists at A1-Adenosine Receptors", Journal of Medicinal Chemistry, 32(8), (1989), 1873-1879.

Jacobson, K. A., et al., "Xanthine Functionalized Congeners as Potent Ligands at A2-Adenosine Receptors", Journal of Medicinal Chemistry, 30(1), (Jan. 1987), 211-214.

Ji, X., et al., "Use of the Triazolotriazine [3H]ZM 241385 as a Radioligand at Recombinant Human A2B Adenosine Receptors", Drug Design and Discovery, 16, (1999), 217-226.

Jiang, Q., et al., "Mutagenesis Reveals Structure-Activity Parallels between Human A2A Adenosine Receptors and Biogenic Amine G Protein-Coupled Receptors", Journal of Medicinal Chemistry, 40 (16), (1997), 2588-2595.

Jin, X, et al., "Inosine Binds to A3 Adenosine Receptors and Stimulates Mast Cell Degranulation", The Journal of Clinical Investigation, 100(11), (1997), 2849-2857.

Kim, H. O., et al., "Structure-Activity Relationships of 1,3-Dialkylxanthine Derivatives at Rat A3 Adenosine Receptors", Journal of Medicial Chemistry, 37(20), (Sep. 30, 1994), 3373-3382.

Kim, Y., et al., "Acyl-Hydrazide Derivatives of a Xanthine Carboxylic Congener (XCC) as Selective Antagonists at Human A2b Adenosine Receptors", Drug Development Research, 47(4), (1999), 178-188.

Kim, Y., et al., "Derivatives of the Triazoloquinazoline Adenosine Antagonist (CGS 15943) Having High Potency at the Human A2B and A3 Receptor Subtypes", Journal of Medicinal Chemistry, 41(15), (1998), 2835-2845.

Kim, Yong-Chul, et al., "Anilide derivatives of an 8-phenylxanthine carboxylic congener are highly potent and selective antagonists at human A2b adenosine receptors", J. Med. Chem.,43(6), (Feb. 26, 2000), 1165-1172.

Kohno, Y., et al., "Activation of A3 Adenosine Receptors on Human Eosinophils Elevates Intracellular Calcium", Blood, 88(9), (Nov. 1, 1996), 3569-3574.

Konduri, G. G., et al., "Adenosine Is a Pulmonary Vasodilator in Newborn Lambs", American Review of Respiratory Disease, 146(3), (Sep. 1992), 670-676.

Linden, J., et al., "125I-Labeled 8-Phenylxanthine Derivatives: Antagonist Radioligands for Adenosine A1 Receptors", Journal of Medicinal Chemistry, 31(4), (Apr. 1988), 745-751.

Linden, J., et al., "Characterization of Human A2B Adenosine Receptors: Radioligand Binding, Western Blotting, and Coupling to Gq in Human Embryonic Kidney 293 Cells and HMC-1 Mast Cells", Molecular Pharmacology, 56, (1999), 705-713.

Linden, J., et al., "Molecular Biology and Pharmacology of Recombinant Adenosine Receptors", In: Cardiovascular Biology of Purines, Eds: G. Burnstock, et al., Kluwer Publishers, (1998), pp. 1-20.

Linden, J., "Molecular Characterization of A2A and A2B Adenosine Receptors (AR)", Drug Development Research, 43(1), Ferrara Abstract No. 7, (Jan. 1998), 1 pg.

Lucarini, N., et al., "Phosphotyrosine protein phosphate and diabetic disorders. Further studies on the relationship between low molecular weight acid phosphasate genotype and degree of glycemic control", Disease Markers, 14, (1998), 121-125.

Lunell, E., et al., "Effects of Enprofylline, a Xanthine Lacking Adenosine Receptor Antagonism, in Pateitns with Chronic Obstructive Lung Disease", European Journal of Clinical Pharmacoloy, 22, (1982), 395-402.

Marquardt, D. W., "An Algorithm for Least-Squares Estimation of Nonlinear Parameters", Journal of the Society for Industrial and Applied Mathematics, 11(2), (Jun. 1963), 431-441.

Martin, P. J., et al., "2-Phenylethoxy-9-Methyladenine: An Adenosine Receptor Antagonist That Discriminates between A2 Adenosine Receptors in the Aorta and the Coronary Vessels from the Guinea Pig", The Journal of Pharmacology and Experimental Therapeutics, 265(1), (Apr. 1993), 248-253.

Mino, R. P., et al., "Adenosine A2b Receptor Inhibition Decreases Retinal Neovascularization in Mice With Oxygen Induced Retinopathy", The Associaton for Research in Vision and Ophthalology (ARVC), [online]. Retrieved from the Internet: <URL: www.arvo.org/arvo/arvo00/50936w.gif>, (Mar. 1, 2000), 2 pgs.

Neary, J. T., et al., "Trophic actions of extracellular nucleotides and nucleosides on glial and neuronal cells", Trends in Neurosciences, 19(1), (1996), 13-18.

Nyce, J. W., et al., "DNA antisense therapy for asthma in an animal model", Nature, 385, (Feb. 20, 1997), 721-725.

Olah, M. E., et al., "125I-4-Aminobenzyl-5'-N-methylcarboxamidoadenosine, a High Affinity Radioligand for the Rat A3 Adenosine Receptor", Molecular Pharmacology, 45, (1994), 978-982.

Palmer, T. M., et al., "125I-4-(2-[7-Amino-2-{2-fury}{1,2,4}triazolo{2,3-a}{1,3,5}triazin-5-yl-amino]ethyl)phenol, a High Affinity Antagonist Radioligand Selective for the A2a Adenosine Receptor", Molecular Pharmacology, 48(6), (Dec. 1995), 970-974.

Papesch, V., et al., "Synthesis of 1-Mono- and 1,3-Di-Substituted 6-Amino-Uracils. Diuretic Activity", The Journal of Organic Chemistry, 16(7), (Jul. 1951), 1879-1890.

Ramkumar, V., et al., "The A3 adenosine receptor is the unique adenosine receptor which facilitates release of allergic mediators in mast cells", Journal of Biological Chemistry, 268(23), (Aug. 15, 1993), 16887-16890.

Resnick, M. B., et al., "Activated Eosinophils Evoke Chloride Secretion in Model Intestinal Epithelia Primarily via Regulated Release of 5'-AMP", The Journal of Immunology, 151(10), (Nov. 15, 1993), 5716-5723.

Schwabe, U., et al., "Characterization of Adenosine Receptors in Rat Brain by (−)[3H]N6-Phenylisopropyladenosine", Archives of Pharmacology, 313 (3), (Sep. 1980), 179-187.

Shamim, M. T., et al., "Effects of 8-Phenyl and 8-Cycloalkyl Substituents on the Activity of Mono-, Di-, and Trisubstituted Alkylxanthines with Substitution at the 1-,3-, and 7-Positions", Journal of Medicinal Chemistry, 32(6), (1989), 1231-1237.

Shepard, R. K., et al., "Adenosine-Induced Vacoconstriction in Vitro. Role of the Mast Cell and A3 Adenosine Receptor", Circulation Research, 78(4), (Apr. 1996), 627-634.

Stowell, C. P., et al., "A Fluorescamine Assay for Submicrogram Quantities of Protein in the Presence of Triton X-100", ANalytical Biochemistry, 85 (85), , (1978), pp. 572-580.

Strohmeier, G. R., et al., "The A2b Adenosine Receptor Mediates cAMP Responses to Adenosine Receptor Agonists in Human Intestinal Epithela", The Journal of Bioligical Chemistry, 270 (5), (Feb. 3, 1995), pp. 2387-2394.

Van Der Wenden, E. M., et al., "8-Substituted adenosine and theophylline-7-riboside analogues as potential partial agonists for the adenosine A1 receptor", European Journal of Pharmacology, Molecular Pharmacology Section 290, , (1995), pp. 189-199.

Vassallo, R., et al., "Theophylline: Recent Advances in the Understanding of Its Mode of Action and Uses in Clinical Practice", Mayo Clin. Proc., 76, Review, (Apr. 1998), pp. 346-354.

* cited by examiner

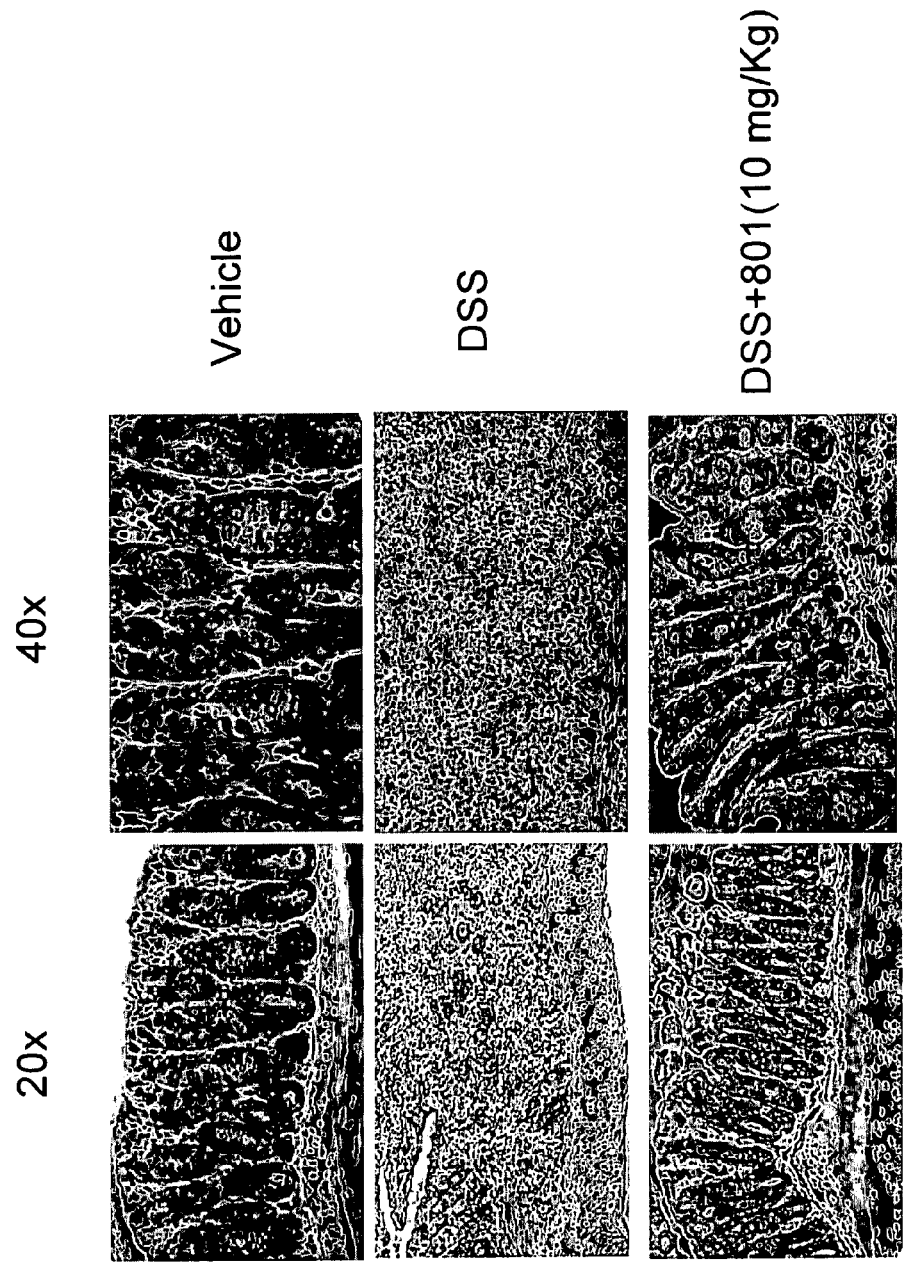

ANTAGONISTS OF A2B ADENOSINE RECEPTORS FOR TREATMENT OF INFLAMMATORY BOWEL DISEASE

CROSS-REFERENCE TO RELATED APPLICATIONS

The present application claims the priority benefits of U.S. Provisional Application No. 60/878,613, filed 4 Jan. 2007, which is expressly incorporated fully herein by reference.

GOVERNMENT RIGHTS

The present invention was made with the assistance of U.S. Government funding (National Institute of Diabetes and Digestive and Kidney Diseases Grant DK06411 (S.V.S), DK 02831 (D.M) and Digestive Disease Research Center grant 5R24DK064399-02). The U.S. Government may have certain rights in this invention.

FIELD OF THE INVENTION

The present invention relates to method for treating inflammatory bowel disease (IBD) that includes administration of an effective amount of an antagonist of $A_{2B}$ adenosine receptors (ARs).

BACKGROUND OF THE INVENTION

Inflammatory bowel disease (IBD) is a group of illnesses, primarily ulcerative colitis or Crohn's disease, that affects the intestines. It has been estimated that over 600,000 Americans suffer from some type of IBD annually. IBD typically causes the intestines to become inflamed. Symptoms of IBD can include abdominal cramps and pain, diarrhea, bleeding, and weight loss.

Ulcerative Colitis (UC) is an inflammation of the lining of the colon and rectum, particularly the mucosa. The disease typically begins in the rectosigmoid area extending proximally through the colon, and may eventually attack the majority of the large bowel resulting in acute and/or chronic inflammation. Acute and chronic inflammation within the colonic mucosa generates inflammatory mediators, called cytokines, which perpetuate the inflammatory process. UC is characterized by flare-ups followed by long periods of remissions. It is a lifelong disease that is estimated to affect as many as two million people in the United States. The major symptoms of ulcerative colitis are bloody diarrhea and abdominal pain, often with fever and weight loss. Additional symptoms of UC include increased stool frequency, rectal bleeding, cramping, weight loss, anemia, intestinal pain, and fever. The clinical course of ulcerative colitis is variable. Victims of UC are also at an increased risk for the development of intestinal cancer. The onset of UC may even cause psychological problems for some people, such as anxiety and depression, while under the strain of this debilitating disease.

Crohn's disease is a chronic disorder that causes inflammation of the digestive or gastrointestinal tract. While not limited to any specific area of the GI tract, it typically affects the end of the small intestine and beginning of the large intestine or colon. UC is generally limited to the colon. Crohn's disease can be difficult to distinguish from UC. Some patients are simply diagnosed with colitis when a specific diagnosis is too difficult. Crohn's disease, like UC, is marked by an abnormal response by the immune system. Unlike UC, Crohn's disease affects more than just the mucosa (superficial layers), Crohn's disease can affect all layers of the intestine, sometimes in a random fashion.

Currently, there is no medical cure for IBD. The available treatments aim at reducing inflammation of the epithelium of the colon, thereby controlling gastrointestinal (GI) symptoms. The major classes of medications used today include aminosalicylates, corticosteroids (e.g., prednisone), and immunomodulatory medicines (e.g., azathioprine and cyclosporine). In view of the deficiency the existing methods of treating ulcerative colitis, it is desirable to develop more effective therapeutic agents.

SUMMARY OF THE INVENTION

The present invention provides a novel method for treating inflammatory bowel disease (e.g., ulcerative colitis and/or Crohn's disease) comprising administering to a patient in need thereof a therapeutically effective amount of an $A_{2B}$ adenosine receptor antagonist or a pharmaceutically acceptable salt thereof.

The invention also provides pharmaceutical compositions comprising an $A_{2B}$ receptor antagonist or a pharmaceutically acceptable salt thereof effective to treat inflammatory bowel disease and a pharmaceutically acceptable excipient.

The invention provides a compound of the present invention or a pharmaceutically acceptable salt thereof for use in medical therapy.

The invention also provides the use of a compound of the present invention or a pharmaceutically acceptable salt thereof for the manufacture of a medicament for the treatment of inflammatory bowel disease.

BRIEF DESCRIPTION IN THE DRAWINGS

The accompanying drawings, which are incorporated herein and form a part of the specification, illustrate some examples of the present invention and together with the description, serve to explain the principles of the invention.

FIG. 1: A2b receptor antagonist ATL-801 inhibits adenosine induced cAMP and chloride secretion: A. T84 monolayers were grown on snap wells and mounted on Using chamber. The cells were stimulated with adenosine (100 µM) after pretreatment with or without ATL-801. cAMP levels were measured as described in the Methods section. Data represented as fold increase over control, ATL-801+ adenosine (gray bar) and adenosine alone (open bar)*p<0.0025, n=3. B. Murine colonic mucosal stripping from the distal colon was mounted on Ussing chamber. The increase in Isc was determined as described in Methods section. After a sustained base-line Isc, the mucosa was stimulated with adenosine (100 µM). Data represents peak Isc response with adenosine. C. Murine colonic mucosa pretreated with ATL-801 (100 µM) 5 minutes before stimulating with Adenosine or Forskolin (10 µM).

Figure 2:
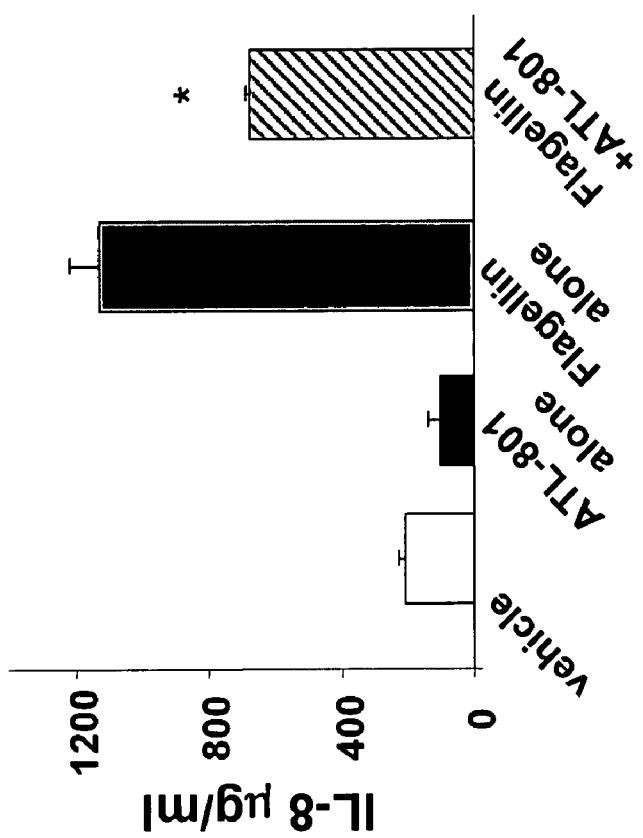

FIG. 2: A2b receptor antagonist ATL-801 inhibits flagellin-induced IL-8 secretion: T84 monolayers were grown on transwells and stimulated with flagellin (100 ng) with or without ATL-801 for 5 hrs. IL-8 was measured as described in the Methods section. Data represented as µM/ml ATL-801+ flagellin (striped bar) and flagellin alone (gray bar) *p<0.007, n=3.

Figure 3:
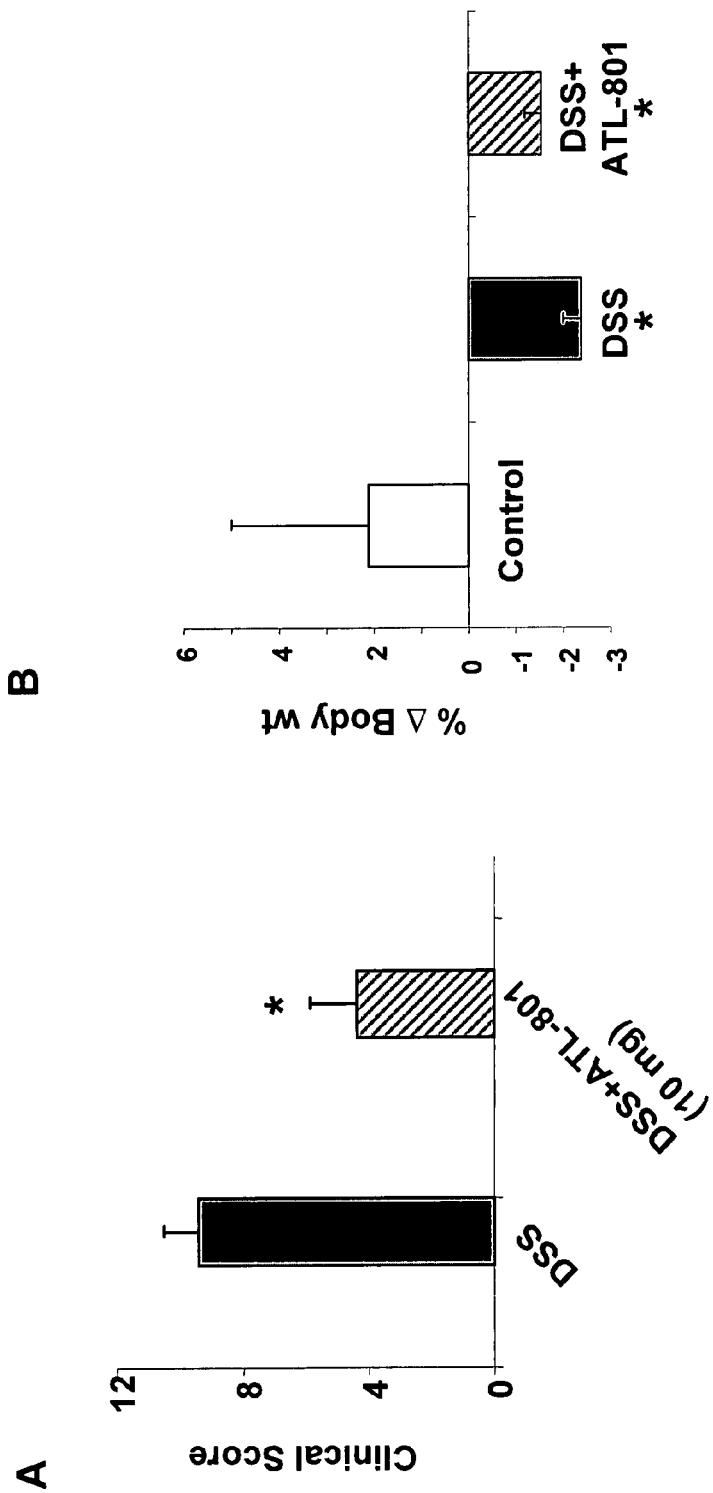

FIG. 3: A2b receptor antagonist attenuates DSS-induced colitis: Mice were weighed and randomized into 3 groups: water, DSS alone (3%), ATL-801 with DSS for 6 days, at which time they were sacrificed. A. Disease severity was assessed as described in the Methods section. The data is represented as clinical score. B. Percent change in body weight compared to day 0. Striped bar represents the group that received ATL-801. Gray bar represents group that received DSS alone. Results are expressed as mean ±S.E., n=5, *p<003.

FIG. 4: A2b receptor antagonist inhibits inflammation associated with DSS: Mice were weighed and randomized into 3 groups: water, DSS alone (3%), ATL-801 with DSS for 6 days, at which time they were sacrificed. A. Colons were removed from mice on day 6, fixed in formalin, paraffin-embedded, sectioned, and stained with H&E. Representative sections of colon from each group are shown. Control mice given water (panel 1), DSS alone (panel 2), DSS+ ATL-801 (panel 3) n=5. B. Myeloperoxidase activity was significantly lower in mice fed with DSS along with ATL-801: Mice were weighed and randomized into 3 groups: water, DSS alone (3%) and ATL-801 (10.0 mg/kg) with DSS for 6 days, at which time they were sacrificed. Colons were snap frozen in liquid nitrogen, and myeloperoxidase was measured as an index of neutrophil infiltration into the injured tissue, as described in the Methods section. Each bar represents mean ±SE. n=5 animals each group. ATL-801+DSS represented as striped bar, DSS-alone gray bar. Open bar represents control mice given water. *p<0.015 and *p<0.038 for mice receiving ATL-801, 10 mg/Kg, in their diet.

Figure 5:
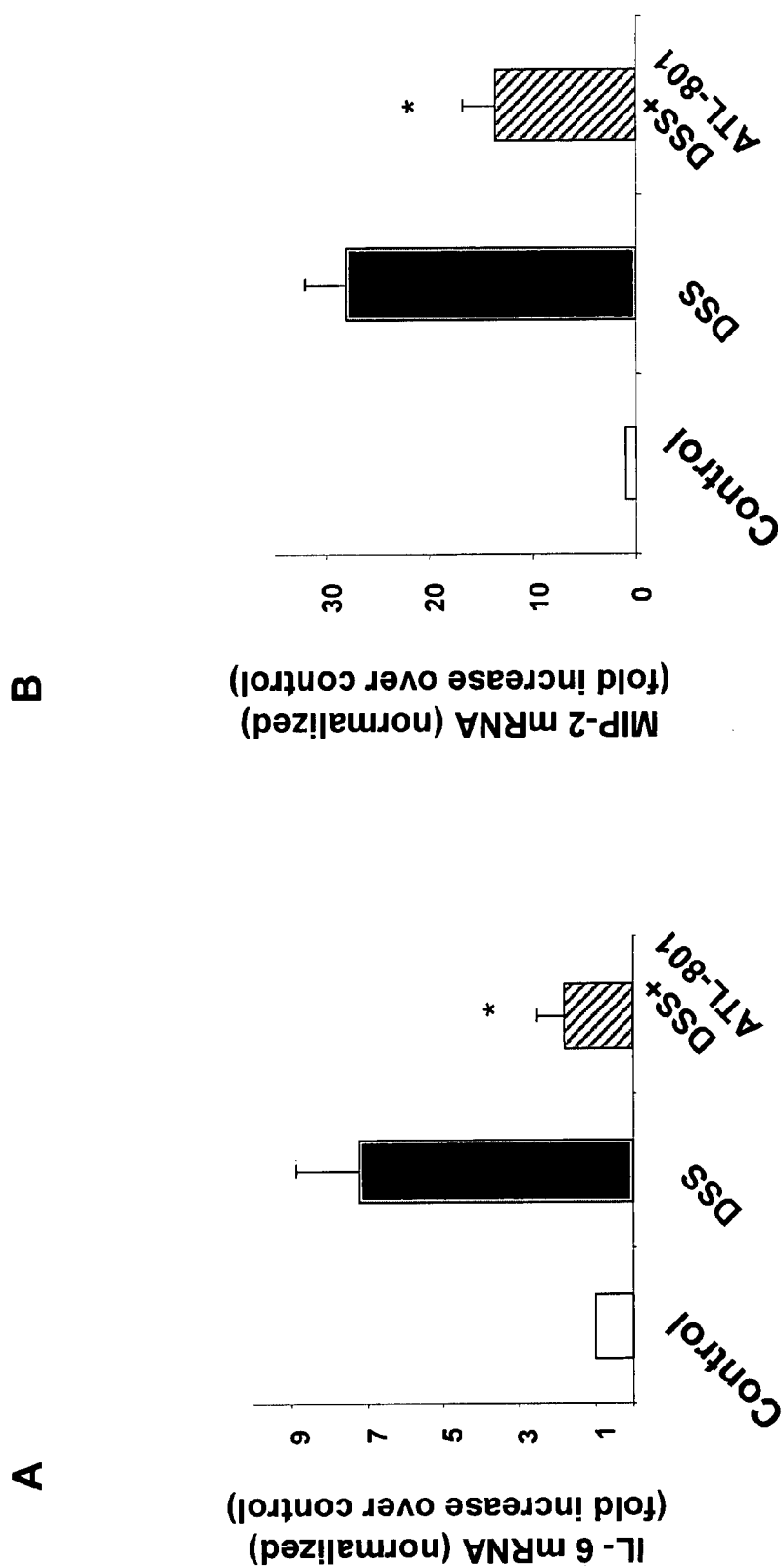

FIG. 5: A2b receptor antagonist inhibits cytokine level in colitis: Mice were weighed and randomized into 3 groups: water, DSS alone (3%), ATL-801 with DSS for 6 days, at which time they were sacrificed. Colonic mucosal stripping was frozen. Total RNA was isolated, reverse transcribed and subjected to real time PCR analysis for IL-6 mRNA as described in Methods section. A.IL-6 mRNA normalized to 36B4 is represented as normalized fold increase over control mice n=5, DSS vs DSS+ATL-801 p<0.01. B.MIP-2 mRNA normalized to 36B4 is represented as fold increase over control n=5, DSS vs DSS+ATL-801 p<0.02. Open bar represents control, gray bar represents DSS alone, striped bar DSS+ATL-801.

Figure 6:
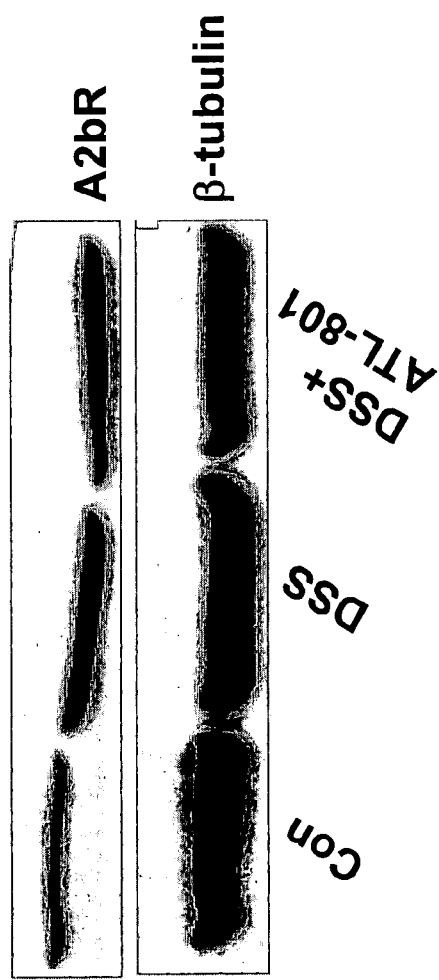

FIG. 6: A2b receptor antagonist does not inhibit A2b receptor expression: Mice were weighed and randomized into 3 groups: water, DSS alone (3%), ATL-801 with DSS for 6 days, at which time they were sacrificed. Colonic tissue was homogenized and cell lysates were subjected to immunoblotting using anti-A2b receptor antibody (1:1000). β-tubulin was used as loading control. Blot shown is representative of 4 animals per condition.

Figure 7:
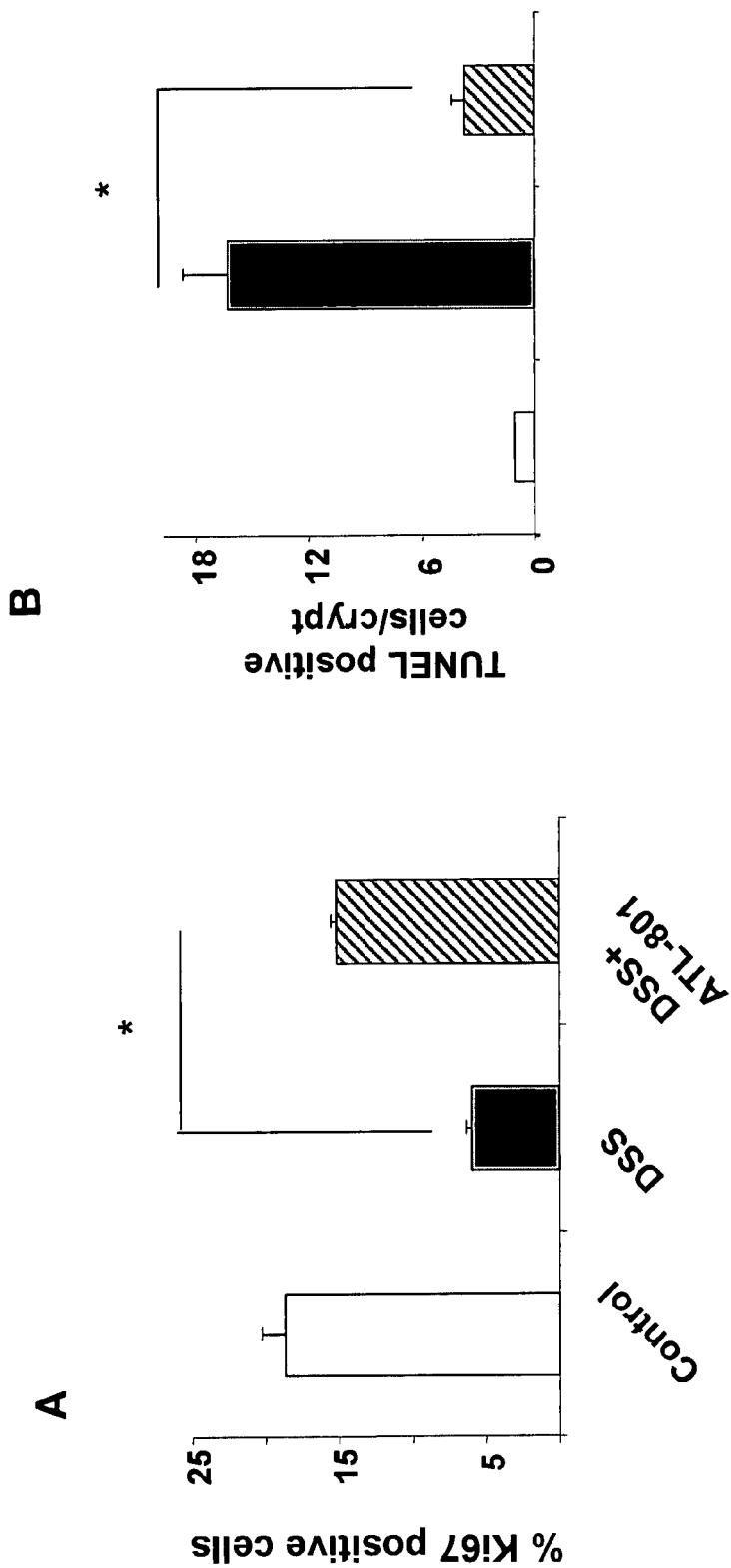

FIG. 7: A2b receptor antagonist enhances proliferation and inhibits apoptosis in DSS-colitis: A. Paraffin embedded sections were stained for ki67 graph represents number of ki67 positive cells. B. Represents number of Caspase 3 and TUNEL positive cells as described in Methods section. Number of cells that stained positive for ki67 and caspase-3 and TUNEL were counted. Data represents average positive cells/per crypt from a total of 30 crypts per mice, 3 mice per group. Open bar control, gray bar DSS group and striped bar DSS+ATL-801.

Figure 8:
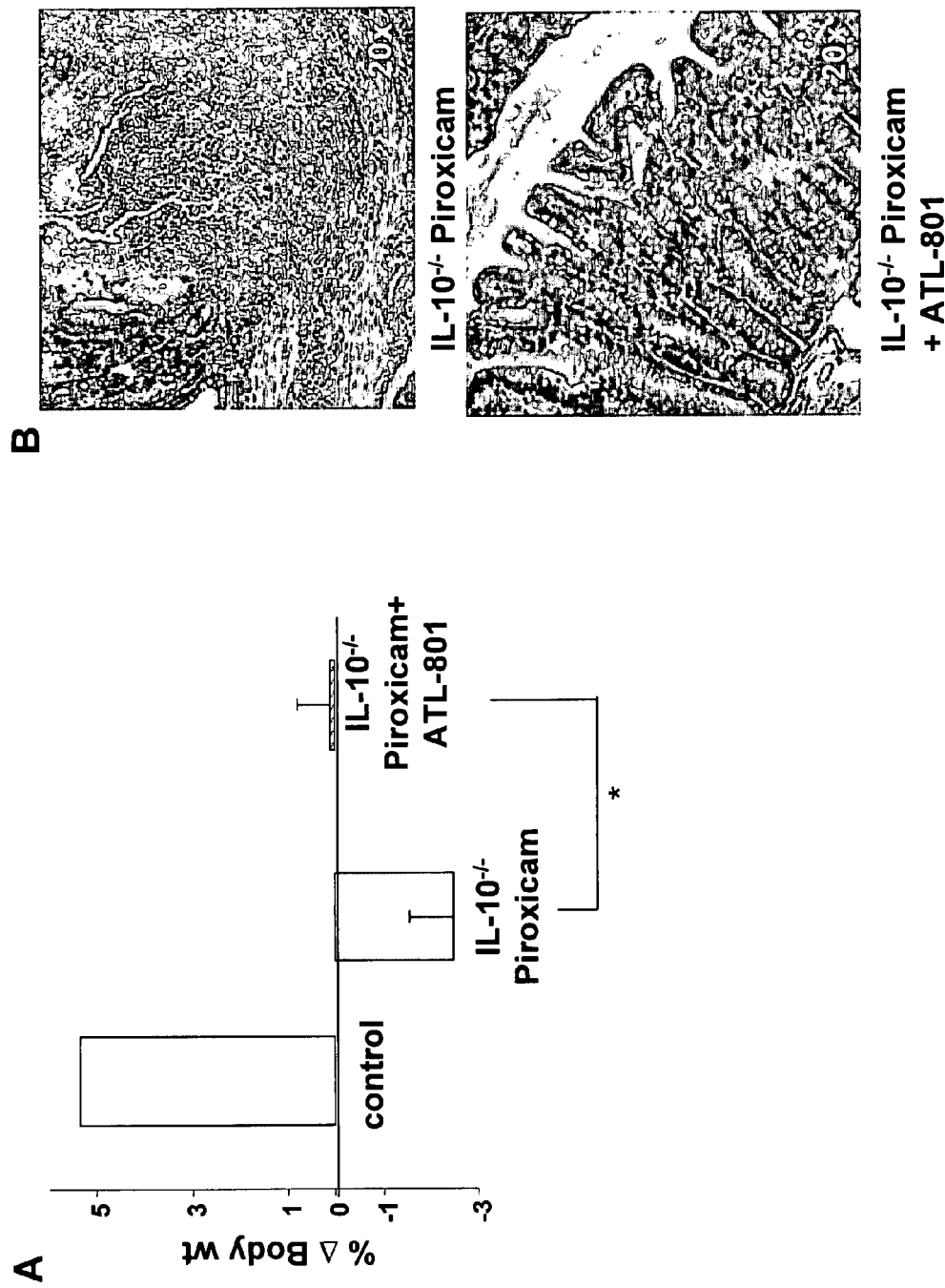

FIG. 8: A2b receptor antagonist inhibits colitis in IL-10$^{-/-}$ mice: IL-10$^{-/-}$ mice were weighed and randomized into 4 groups. Group 1 was comprised of control mice, group 2 received piroxicam alone (200 mg/kg diet) for 2 weeks to induce colitis, group 3 received ATL-801 (10 mg/kg) along with 2 weeks of piroxicam and then was continued on ATL-801 for 2 more weeks, while group 4 received ATL-801 alone for all 4 weeks. A. Percent body weight change is shown. Open bar control, gray bar represents IL-10$^{-/-}$ treated with piroxicam, stripped bar IL-10$^{-/-}$ mice treated with piroxicam and ATL-801, B. Mice were sacrificed after 4 weeks and colons were fixed in formalin, paraffin-embedded, sectioned and stained with H&E. Representative sections of colon from group 2 and group 3 are shown at 20× magnifications. Top panel represents the group that received piroxicam alone. Bottom panel represents the group that received piroxicam with ATL-801 in their diet (n=5).

Figure 9:
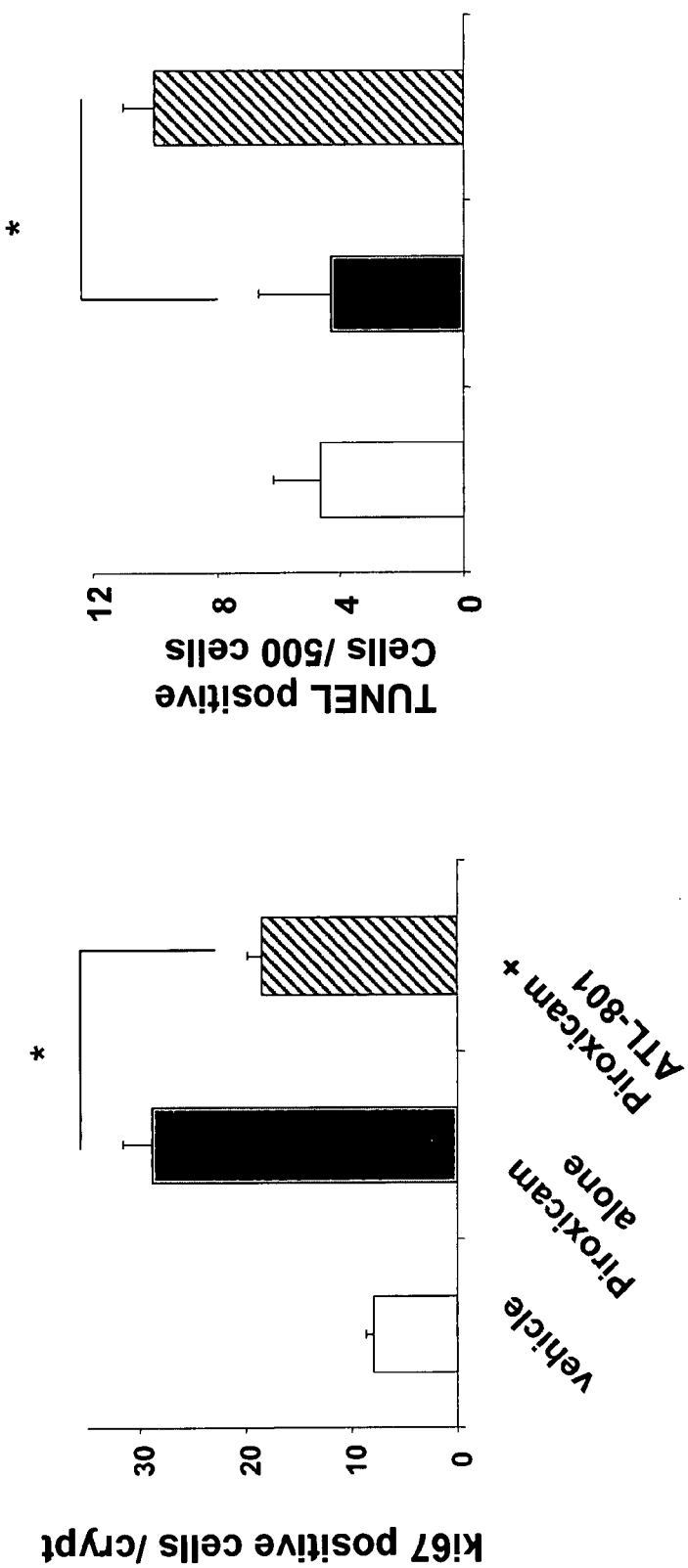

FIG. 9: A2b receptor inhibition suppresses proliferation associated with piroxicam-induced colitis: IL-10$^{-/-}$ mice were weighed and randomized into 4 groups. Group 1 was comprised of control mice, group 2 received piroxicam alone (200 mg/kg diet) for 2 weeks to induce colitis, group 3 received ATL-801 (10 mg/kg) along with 2 weeks of piroxicam and then was continued on ATL-801 for 2 more weeks, while group 4 received ATL-801 alone for all 4 weeks. Mice were sacrificed after 4 weeks and colons were fixed in formalin. A. Paraffin-embedded sections were processed for ki67. B Frozen sections were used for TUNEL staining as described in Methods section. Open bar control, gray bar represents IL-1$^{-/-}$ treated with piroxicam, stripped bar IL-1$^{-/-}$ mice treated with piroxicam and ATL-801.

Figure 10:
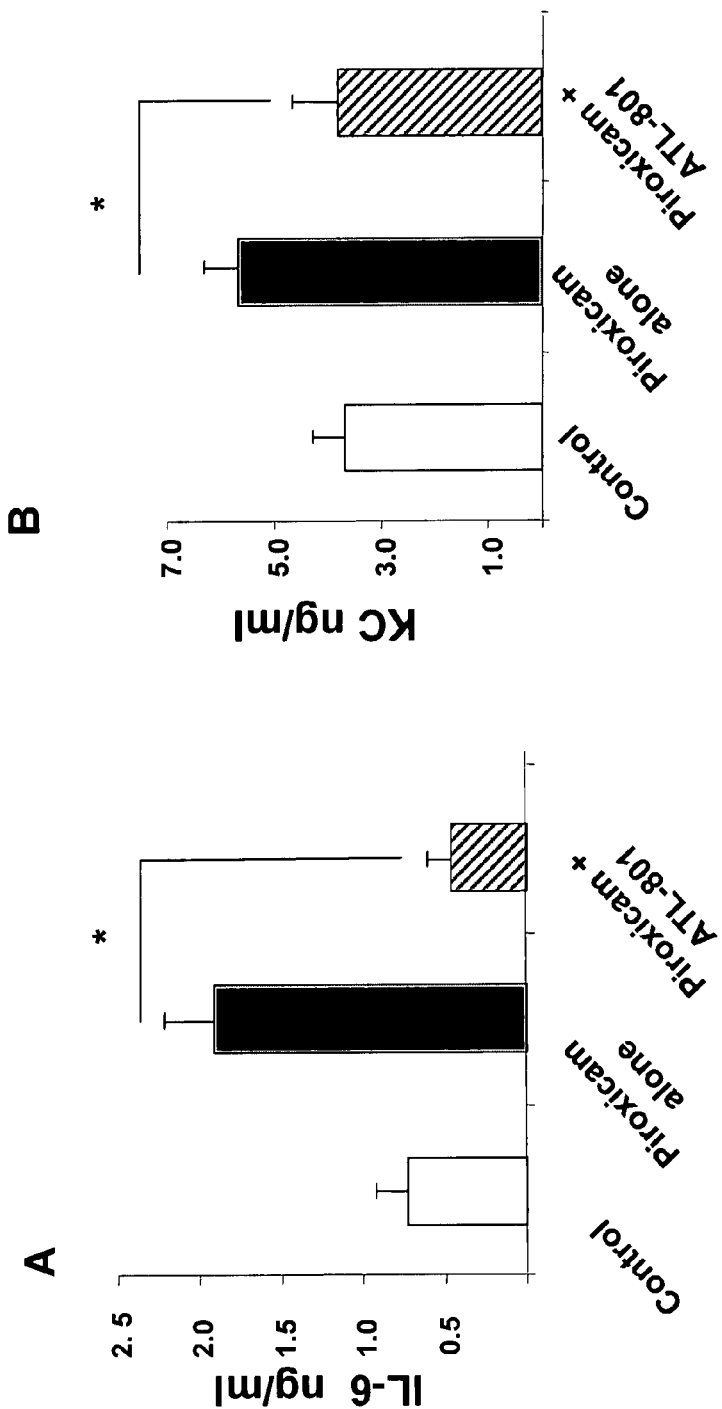

FIG. 10: A2b receptor inhibition suppresses production of pro-inflammatory cytokines: Colonic tissue culture supernatants obtained from IL-10$^{-/-}$ mice treated with piroxicam with or without ATL-801 were processed for IL-6 and KC secretion as described in Methods section. A. IL-6 levels in IL-10-mice treated with ATL-801 (stripped bar, p<0.006) (n=5) compared to piroxicam alone (gray bar). B. KC levels in IL-10$^{-/-}$ mice treated with ATL-801 (stripped bar, p<0.003) compared to piroxicam alone (gray bar), open bar represents control mice.

DETAILED DESCRIPTION OF THE INVENTION

It has now been discovered that a selective A2b receptor antagonist, ATL-801, ameliorates experimental colitis in two mouse models that represent both acute and chronic forms of gut inflammation. In the first model, colitis was induced by oral administration of DSS. In these mice, ATL-801 protected against DSS-induced colitis and showed reduced inflammatory cell infiltration, focal crypt damage, epithelial injury, and ulceration. One of the findings was that DSS+ATL-801 treated mice showed marked reduction in diarrhea, as demonstrated by solid stool pellets and increased stool weight compared to mice treated with DSS alone, which had diarrhea and no stool in the colon as reflected by lower weight of the colon. This result is consistent with a known effect of adenosine in mediating cAMP-dependent chloride secretion and secretory diarrhea. Although A2b receptor has been well documented to mediate chloride secretion in epithelial cell lines in vitro, this is the first demonstration of an effect of A2b receptor on diarrhea in vivo. Diarrhea associated with intestinal inflammation is multifactorial. The results on the inhibition of adenosine-induced chloride secretion by ATL-801 in colonic mucosal stripping ex vivo in conjunction with the inhibition of colitis associated diarrhea by ATL-801 suggests inhibition of chloride secretion as a potential mechanism by which ATL-801 reduces diarrhea.

In addition to the effect of ATL-801 on diarrhea, inflammatory infiltration was reduced in both DSS and IL-10$^{-/-}$ mice models of colitis. In the DSS model which is characterized by neutrophil infiltration, crypt damage and ulcers, ATL-801 reduced the extent of neutrophil infiltration as assessed by histology as well as MPO assay. There was significantly reduced ulceration and crypt damage by ATL-801 in a dose-dependent fashion. Similarly, ATL-801 protected against chronic inflammatory infiltrates and epithelial hyperplasia that characterize colitis in IL-10$^{-/-}$ mice. Finally, the protection against colitis by ATL-801 was reflected in reduced IL-6 and KC secretion in ex vivo colon cultures obtained from colitic mice.

In light of Applicants discovery that $A_{2B}$ adenosine receptor antagonists can be useful for treating inflammatory bowel disease, the present invention provides a novel method for treating inflammatory bowel disease, comprising: administering to a patient in need thereof a therapeutically effective amount of an $A_{2B}$ adenosine receptor antagonist.

The present invention also provides a novel method wherein the inflammatory bowel disease is ulcerative colitis.

The present invention also provides a novel method wherein the inflammatory bowel disease is Crohn's disease.

The present invention also provides a novel method, wherein the $A_{2B}$ adenosine receptor antagonist is a substituted xanthine.

The present invention also provides a novel method, wherein the $A_{2B}$ adenosine receptor antagonist is a substituted 8-phenyl-xanthine or a substituted 8-(5-6 membered heteroaryl)-xanthine.

$A_{2B}$ antagonists are well known and have been described in numerous patents and patent publications. The following patents and patent publications are representative examples, all of which are incorporated herein by reference: U.S. No. 60/805,030; US 2005/0065341; U.S. Ser. Nos. 11/362,393; 11/362,387; and 11/362,392. Additional publications that show $A_{2B}$ antagonists include: U.S. Pat. No. 6,825,349; WO2006/028810; U.S. Pat. No. 6,977,300; US 2003/207879; WO2003063800; U.S. Pat. Nos. 6,117,878; 6,545,002; US 2003/171383; US 2003/229067; US 2004/176399; WO2000/73307; WO2003/002566; WO2003/006465; WO2003/042214; WO2003/053366; WO2003/063800; U.S. Pat. Nos. 5,734,051; 5,734,052; 6,180,791; WO1994/26744; WO2001/16134; US 2003/087904; U.S. Pat. No. 4,548,820; EP0698607; EP0619316; EP0607607; EP0590919; EP0559893; EP0449175; EP0389282; EP0267607; EP0203721; and, EP0092398.

The present invention also provides a novel method, wherein the $A_{2B}$ adenosine receptor antagonist is a compound of formula I or a stereoisomer or pharmaceutically acceptable salt:

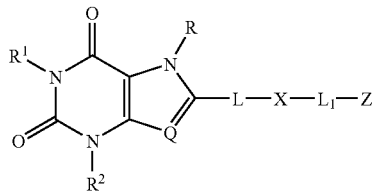

I wherein:

Q is N or CH;

R is selected from H, $(C_1-C_5)$alkyl, halo$(C_1-C_8)$alkyl, $(C_3-C_5)$alkenyl, and $(C_3-C_5)$alkynyl;

$R^1$ and $R^2$ are independently selected from H, $(C_1-C_8)$alkyl, $(C_3-C_8)$alkenyl, $(C_3-C_8)$alkynyl, $(C_1-C_8)$alkoxy, $(C_3-C_8)$cycloalkyl, $(C_3-C_8)$cycloalkyl$(C_1-C_8)$alkyl-, $(C_4-C_{10})$heterocycle, $(C_4-C_{10})$heterocycle$(C_1-C_8)$alkyl-, $(C_6-C_{10})$aryl, $(C_6-C_{10})$aryl$(C_1-C_8)$alkyl-, $(C_5-C_{10})$heteroaryl, and $(C_5-C_{10})$heteroaryl$(C_1-C_8)$alkyl-;

L and $L_1$ are independently absent or are independently $C_1-C_4$ alkylene linking groups wherein from 0-2 of the carbon atoms of the linking groups are independently replaced by non-peroxide oxy (—O—), thio (—S—), sulfinyl (—SO—), sulfonyl (—S(O)$_2$—) and amine-N(H)—, and the linker is optionally substituted with 1, 2, or 3 substituents independently selected from halo, cyano, nitro, —OR$^a$, —SR$^a$, $(C_6-C_{10})$aryl, —O$(C_6-C_{10})$aryl, halo$(C_1-C_4)$alkyl, and —NR$^b$R$^c$;

X is selected from a 5-14 membered heteroaryl ring having one nitrogen atom and optionally interrupted by 1, 2, or 3 non-peroxide oxy (—O—), thio (—S—), sulfinyl (—SO—), sulfonyl (—S(O)$_2$—) or amine-N(R$^9$)-groups and the heteroaryl is optionally substituted with 1, 2, 3, or 4 substituents independently selected from halo, cyano, nitro, —OR$^a$, —SR$^a$, $(C_1-C_8)$alkyl, $(C_6-C_{10})$aryl, —O$(C_6-C_{10})$aryl, hydroxy$(C_1-C_8)$alkyl, R$^b$R$^c$N$(C_1-C_8)$alkyl, halo$(C_1-C_8)$alkyl, —NR$^b$R$^c$, —C(O)R$^a$, —COOR$^a$, and —C(O)NR$^b$R$^c$;

Z is selected from —OR$^3$, —SR$^3$, halo, —S(O)$_m$—NR$^4$R$^5$, —NR$^4$R$^5$, and 5-14 membered heterocycle or heteroaryl wherein the heterocycle or heteroaryl is optionally substituted with 1, 2, 3, or 4 substituents independently selected from halo, cyano, nitro, —OR$^a$, —SR$^a$, $(C_1-C_8)$alkyl, $(C_6-C_{10})$aryl, —O$(C_6-C_{10})$aryl, hydroxy$(C_1-C_8)$alkyl, R$^b$R$^c$N$(C_1-C_8)$alkyl, halo$(C_1-C_8)$alkyl, —NR$^b$R$^c$, —C(O)R$^a$, —COOR$^a$, and —C(O)N$^b$R$^c$;

$R^3$ is selected from $(C_1-C_8)$alkyl, $(C_3-C_8)$alkenyl, $(C_3-C_8)$alkynyl, $(C_6-C_{10})$aryl, $(C_6-C_{10})$aryl$(C_1-C_8)$alkyl-, $(C_5-C_{10})$heteroaryl, $(C_5-C_{10})$heteroaryl$(C_1-C_8)$alkyl-, —C(O)R$^6$, and —C(O)NR$^7$R$^8$;

$R^4$ and $R^5$ are independently selected from H, $(C_1-C_8)$alkyl, $(C_3-C_8)$alkenyl, $(C_3-C_8)$alkynyl, $(C_1-C_8)$alkoxy, $(C_3-C_8)$cycloalkyl, $(C_3-C_8)$cycloalkyl$(C_1-C_8)$alkyl-, $(C_6-C_{18})$polycycloalkyl, $(C_6-C_{18})$polycycloalkyl$(C_1-C_8)$alkyl-, $(C_3-C_{10})$heterocycle, $(C_3-C_{10})$heterocycle$(C_1-C_8)$alkyl-, —NR$^7$R$^8$, $(C_6-C_{10})$aryl, $(C_6-C_{10})$aryl$(C_1-C_8)$alkyl-, $(C_5-C_{10})$heteroaryl, $(C_5-C_{10})$heteroaryl$(C_1-C_8)$alkyl-, —$(C_2-C_4$—Y)$_q$—(CH$_2$)$_{2-4}$—X$^1$, —C(O)R$^6$, —CO$_2$R$^6$, —C(O)NR$^7$R$^8$, and —S(O)$_2$—NR$^7$R$^8$;

$X^1$ is selected from —OR$^6$, —C(O)R$^6$, —CO$_2$R$^6$, and —NR$^7$R$^8$;

Y is selected from oxy (—O—), thio (—S—), sulfinyl (—SO—), sulfonyl (—S(O)$_2$—) and amine-N(R$^9$)—;

$R^6$ is selected from H, $(C_1-C_8)$alkyl, R$^a$O$(C_1-C_8)$alkyl, R$^b$R$^c$N$(C_1-C_8)$alkyl, halo$(C_1-C_8)$alkyl, $(C_3-C_6)$cycloalkyl, $(C_3-C_6)$cycloalkyl$(C_1-C_4)$alkyl-, $(C_3-C_{10})$heterocycle, $(C_3-C_{10})$heterocycle$(C_1-C_8)$alkyl-, $(C_6-C_{10})$aryl, $(C_6-C_{10})$aryl$(C_1-C_8)$alkyl-, $(C_4-C_{10})$heteroaryl, and $(C_4-C_{10})$heteroaryl$(C_1-C_8)$alkyl-;

$R^7$, $R^8$, and $R^9$ are independently selected from H, $(C_1-C_8)$alkyl, R$^a$O$(C_1-C_8)$alkyl, R$^b$R$^c$N$(C_1-C_8)$alkyl, halo$(C_1-C_8)$alkyl, $(C_3-C_{10})$heterocycle, $(C_6-C_{10})$aryl, $(C_6-C_{10})$aryl$(C_1-C_8)$alkyl-, $(C_4-C_{10})$heteroaryl; —COOR$^a$, —C(O)R$^a$, and —C(O)NR$^b$R$^c$;

alternatively, $R^7$ and $R^8$ together with the atoms to which they are attached form a saturated or partially unsaturated, mono-, bicyclic-, or aromatic ring having 3, 4, 5, 6, 7, or 8, ring atoms and there optionally being 1, 2, 3, or 4 heteroatoms selected from non-peroxide oxy (—O—), thio (—S—), sulfinyl (—SO—), sulfonyl (—S(O)$_2$—) or amine-N(R$^b$)-in the ring;

wherein the alkyl, alkenyl, cycloalkyl, alkynyl, aryl, heterocycle or heteroaryl groups of $R^1$, $R^2$, $R^3$, $R^4$, $R^5$, $R^6$, $R^7$, $R^8$, and $R^9$ are optionally substituted with one or more substituents independently selected from halo, cyano, nitro, —OR$^a$, SR$^8$, $(C_1-C_8)$alkyl, $(C_6-C_{10})$aryl, —O$(C_6-C_{10})$aryl, hydroxy$(C_1-C_8)$alkyl, R$^b$R$^c$N$(C_1-C_8)$alkyl, halo$(C_1-C_8)$alkyl, —NR$^b$R$^c$, —C(O)R$^a$, —COOR$^a$, and —C(O)NR$^b$R$^c$;

$R^a$ is selected from H, and $(C_1-C_6)$alkyl;

$R^b$ and $R^c$ are each independently H, $(C_1-C_6)$alkyl, $(C_1-C_6)$alkoxy, $(C_3-C_8)$cycloalkyl, $(C_1-C_6)$alkylthio, $(C_6-C_{10})$aryl, $(C_6-C_{10})$aryl$(C_1-C_6)$alkyl-, heteroaryl, and heteroaryl$(C_1-C_6)$-alkyl-;

alternatively, $R^b$ and $R^c$ together with the nitrogen to which they are attached, form a ring selected from pyrrolidyl, piperidyl, piperazinyl, azepinyl, diazepinyl, morpholinyl, and thiomorpholinyl;

m is independently selected from 1, and 2; and, q is independently selected from 1, 2, 3, and 4.

The present invention also provides a novel method, wherein the antagonist is a compound of formula Ia or Ib or a stereoisomer or pharmaceutically acceptable salt:

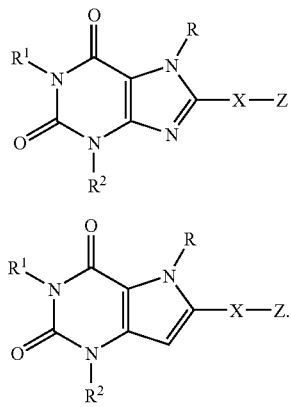

The present invention also provides a novel method, wherein:

R is selected from H, methyl, and ethyl;

$R^1$ is selected from $(C_1-C_4)$alkyl, $(C_3-C_4)$alkenyl, $(C_3-C_4)$alkynyl, $(C_3-C_6)$cycloalkyl, and $(C_3-C_6)$cycloalkyl$(C_1-C_4)$alkyl-;

$R^2$ is selected from H, $(C_1-C_4)$alkyl, $(C_3-C_4)$alkenyl, $(C_3-C_4)$alkynyl, $(C_3-C_6)$cycloalkyl, and $(C_3-C_6)$cycloalkyl$(C_1-C_4)$alkyl-;

X is selected from imidazolyl, triazolyl, triazinyl, oxazoyl, isoxazoyl, thiazolyl, isothiazoyl, thiodiazolyl, pyrrolyl, pyrazinyl, tetrazolyl, pyridinyl, pyrimidinyl, indolyl, iso-quinolyl, quinolyl, and triazolopyridinyl, each optionally substituted with 1, 2, or 3 substituents independently selected from halo, cyano, nitro, —$OR^a$, $SR^a$, $(C_1-C_4)$alkyl, $(C_6-C_{10})$aryl, —$O(C_6-C_{10})$aryl, hydroxy$(C_1-C_8)$alkyl, $R^bR^cN(C_1-C_8)$alkyl, halo$(C_1-C_4)$alkyl, —$NR^bR^c$, —$C(O)R^a$, —$COOR^a$, and —$C(O)NR^bR^c$.

Z is selected from —OH, —$O(C_1-C_4)$alkyl, —$O(C_6-C_{10})$aryl, $(C_6-C_{10})$aryl$(C_1-C_4)$alkylO—, —$NR^4R^5$, F, and Cl;

alternatively Z is selected from pyrazolyl, pyrrolidyl, piperidyl, piperazinyl, azepinyl, diazepinyl, morpholinyl, and thiomorpholinyl attached to X via a ring N and optionally substituted with 1, 2, or 3 substituents independently selected from halo, cyano, nitro, —$OR^a$, $SR^a$, $(C_6-C_{10})$aryl, —$O(C_6-C_{10})$aryl, hydroxy$(C_1-C_4)$alkyl, $R^bR^cN(C_1-C_4)$alkyl, halo$(C_1-C_4)$alkyl, —$NR^bR^c$, —$C(O)R^a$, —$COOR^a$, and —$C(O)NR^bR^c$;

$R^4$ is selected from H, $(C_1-C_6)$alkyl, $(C_3-C_4)$alkenyl, hydroxyl$(C_2-C_4)$alkyl, $(C_3-C_6)$cycloalkyl, $(C_3-C_6)$cycloalkyl$(C_1-C_4)$alkyl-, $(C_3-C_6)$heterocycle, $(C_3-C_4)$alkenyl, $(C_3-C_6)$heterocycle$(C_1-C_4)$alkyl-, $(C_6-C_{10})$aryl, $(C_6-C_{10})$aryl$(C_1-C_4)$alkyl-, $(C_5-C_6)$heteroaryl, $(C_5-C_6)$heteroaryl$(C_1-C_4)$alkyl-, —$(C_2-C_4-Y)_q$—$(CH_2)_{2-4}$—$X^1$, —$SO_2NH_2$, —$NR^7R^8$, $C(O)R^6$, —$CO_2R^6$, and —$C(O)NR^7R^8$, each optionally substituted with 1, 2, or 3 substituents independently selected from the group consisting of halo, cyano, nitro, —$OR^a$, $SR^a$, $(C_1-C_4)$alkyl, $(C_6-C_{10})$aryl, —$O(C_6-C_{10})$aryl, hydroxy$(C_1-C_4)$alkyl, $R^bR^cN(C_1-C_4)$alkyl, halo$(C_1-C_4)$alkyl, —$NR^bR^c$, —$C(O)R^a$, —$COOR^a$, and —$C(O)NR^bR^c$;

$R^5$ is selected from $(C_1-C_6)$alkyl, $(C_3-C_4)$alkenyl, hydroxyl$(C_2-C_4)$alkyl, $(C_3-C_6)$cycloalkyl, $(C_3-C_6)$cycloalkyl$(C_1-C_4)$alkyl-, $(C_3-C_6)$heterocycle, $(C_3-C_6)$heterocycle$(C_1-C_4)$alkyl-, $(C_6-C_{10})$aryl, $(C_6-C_{10})$aryl$(C_1-C_4)$alkyl-, $(C_5-C_6)$heteroaryl, $(C_5-C_6)$heteroaryl$(C_1-C_4)$alkyl-, —$SO_2NH_2$, —$NR^7R^8$, $C(O)R^6$, —$CO_2R^6$, and —$C(O)NR^7R^8$, each optionally substituted with 1, 2, or 3 substituents independently selected from the group consisting of halo, cyano, nitro, —$OR^a$, $SR^a$, $(C_1-C_4)$alkyl, $(C_6-C_{10})$aryl, —$O(C_6-C_{10})$aryl, hydroxy$(C_1-C_4)$alkyl, $R^bR^cN(C_1-C_4)$alkyl, halo$(C_1-C_4)$alkyl, —$NR^bR^c$, —$C(O)R^a$, —$COOR^a$, and —$C(O)NR^bR^c$; and, $R^6$ is selected from $(C_1-C_6)$alkyl, $(C_3-C_6)$cycloalkyl, $(C_3-C_6)$cycloalkyl$(C_1-C_4)$alkyl-, $(C_3-C_6)$heterocycle, $(C_6-C_{10})$aryl, $(C_6-C_{10})$aryl$(C_1-C_4)$alkyl-, $(C_5-C_6)$heteroaryl, and $(C_5-C_6)$heteroaryl$(C_1-C_4)$-alkyl-, each optionally substituted with 1, 2, or 3 substituents independently selected from the group consisting of halo, cyano, nitro, $(C_1-C_8)$alkyl, —$OR^a$, —$SR^a$, $(C_6-C_{10})$aryl, —$O(C_6-C_{10})$aryl, hydroxy$(C_1-C_4)$alkyl, $R^bR^cN(C_1-C_4)$alkyl, and —$C(O)NR^bR^c$; halo$(C_1-C_4)$alkyl, —$NR^bR^c$, —$C(O)R^a$, —$COOR^a$, and —$C(O)NR^bR^c$;

The present invention also provides a novel method, wherein:

R is H;

$R^1$ is selected from methyl, ethyl, allyl, propargyl, i-propyl, n-propyl, cyclopropyl, and cyclopropylmethyl;

$R^2$ is selected from methyl, ethyl, allyl, propargyl, i-propyl, n-propyl, cyclopropyl, and cyclopropylmethyl;

X is selected from 2-pyridinyl, 3-pyridinyl, 4-pyridinyl, and [1,2,4]triazolo[4,3-a]pyridin-6-yl, and is optionally substituted with 1, 2, or 3 substituents independently selected from halo, cyano, nitro, —$OR^a$, —$SR^a$, $(C_1-C_4)$alkyl, $(C_6-C_{10})$aryl, —$O(C_6-C_{10})$aryl, hydroxy$(C_1-C_4)$alkyl, $R^bR^cN(C_1-C_4)$alkyl, halo$(C_1-C_4)$alkyl, —$NR^bR^c$, —$C(O)R^a$, —$COOR^a$, and —$C(O)NR^bR^c$.

Z is selected from —OH and —$NR^4R^5$;

alternatively Z is selected from pyrazolyl, pyrrolidyl, piperidyl, piperazinyl, and morpholinyl attached to X via a ring N and optionally substituted with 1 or 2 substituents independently selected from halo, cyano, nitro, —$OR^a$, $SR^a$, $(C_6-C_{10})$aryl, hydroxy$(C_1-C_2)$alkyl, $R^bR^cN(C_1-C_2)$alkyl, halo$(C_1-C_2)$alkyl, —$NR^bR^c$, —$C(O)R^a$, —$COOR^a$, and —$C(O)NR^bR^c$;

$R^4$ is selected from H, $(C_1-C_4)$alkyl, $(C_3-C_4)$alkenyl, hydroxy$(C_2-C_4)$alkyl, $(C_3-C_6)$cycloalkyl, $(C_3-C_6)$cycloalkyl$(C_1-C_2)$alkyl-, $(C_6-C_{10})$aryl, $(C_6-C_{10})$aryl-$(C_1-C_2)$alkyl-, $(C_5-C_6)$heterocycle$(C_1-C_2)$alkyl-, $(C_5-C_6)$heteroaryl, $(C_5-C_6)$heteroaryl$(C_1-C_2)$alkyl-, —$(CH_2-CH_2-O)_q$—$(CH_2-CH_2)$—$OR^a$, —$(CH_2-CH_2-O)_q$—$(CH_2-CH_2)$—$COOR^a$, —$(CH_2-CH_2-O)_q$—$(CH_2-CH_2)$—$NR^aR^b$, and —$NR^7R^8$, each aryl and heteroaryl optionally substituted with 1 or 2 substituents independently selected from the group consisting of halo, cyano, nitro, —$OR^a$, $SR^a$, $(C_1-C_4)$alkyl, $R^bR^cN(C_1-C_2)$alkyl, halo$(C_1-C_2)$alkyl, —$NR^bR^c$, —$C(O)R^a$, —$COOR^a$, and —$C(O)NR^bR^c$;

$R^5$ is selected from $(C_1-C_4)$alkyl, $(C_3-C_4)$alkenyl, hydroxy$(C_2-C_4)$alkyl, $(C_3-C_6)$cycloalkyl, $(C_3-C_6)$cycloalkyl$(C_1-C_2)$alkyl-, $(C_6-C_{10})$aryl, $(C_6-C_{10})$aryl-$(C_1-C_2)$alkyl-, $(C_3-C_6)$heterocycle$(C_1-C_2)$alkyl-, $(C_5-C_6)$heteroaryl, $(C_5-C_6)$heteroaryl$(C_1-C_2)$alkyl-, —$C(O)R^a$, —$CO_2R^6$, and —$C(O)NR^7R^8$, each aryl and heteroaryl optionally substituted with 1 or 2 substituents independently selected from the group consisting of halo, cyano, nitro, —OR$^a$, —SR$^a$, (C$_1$-C$_4$)alkyl, R$^b$R$^c$N(C$_1$-C$_2$)alkyl, halo(C$_1$-C$_2$)alkyl, —NR$^b$R$^c$, —C(O) R$^a$, —COOR$^a$, and —C(O)NR$^b$R$^c$; and, R$^6$ is selected from (C$_6$-C$_{10}$)aryl and (C$_5$-C$_6$)heteroaryl, each optionally substituted with 1, 2, or 3 substituents independently selected from halo, cyano, nitro, (C$_1$-C$_4$)alkyl, halo (C$_1$-C$_4$)alkyl, —COOR$^a$, and —C(O)NR$^b$R$^c$.

The present invention also provides a novel method, wherein:

R$^1$ is selected from ethyl, allyl, n-propyl, and cyclopropylmethyl;

R$^2$ is selected from ethyl, allyl, n-propyl, and cyclopropylmethyl;

X is selected from 2-pyridinyl and 3-pyridinyl, and is optionally substituted with 1 or 2 substituents independently selected from halo, cyano, nitro, —OR$^a$, —SR$^a$, (C$_1$-C$_4$) alkyl, (C$_6$-C$_{10}$)aryl, —O(C$_6$-C$_{10}$)aryl, hydroxy(C$_1$-C$_4$)alkyl, R$^b$R$^c$N(C$_1$-C$_4$)alkyl, halo(C$_1$-C$_4$)alkyl, —NR$^b$R$^c$, —C(O) R$^a$, COOR$^a$, and —C(O)NR$^b$R$^c$.

Z is —NR$^4$R$^5$;

alternatively Z is selected from pyrazolyl, piperazinyl, and morpholinyl attached to X via a ring N and optionally substituted with 1 or 2 substituents independently selected from halo, cyano, nitro, —OR$^a$, —SR$^a$, (C$_6$-C$_{10}$)aryl, hydroxy(C$_1$-C$_2$)alkyl, and halo(C$_1$-C$_2$)alkyl;

R$^4$ is selected from methyl, ethyl, propyl, butyl, allyl, hydroxyethyl, hydroxypropyl, methoxyethyl, methylbenzyl, aminomethylbenzyl, methoxybenzyl, methoxyphenethyl, furylmethyl, cyclopropyl, cyclopropylmethyl, cyclopentyl, cyclohexyl, thiophenyl, tetrahydrofuranylmethyl-, pyrrolidinylethyl-, piperidinylethyl-, morpholinylethyl-, and thiophenylmethyl-;

R$^5$ is selected from methyl, ethyl, propyl, hydroxyethyl, hydroxypropyl, methoxyethyl, cyclopropyl, cyclopropylmethyl, —C(O)R$^6$, —CO$_2$R$^6$, and —C(O)NHR$^7$; and, R$^6$ is pyridyl, optionally substituted with F, Cl, Br, I, CF$_3$, cyano, nitro, —COOR$^a$, and —CONHR$^a$.

The present invention also provides a novel method, wherein:

—X—Z is

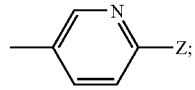

R$^4$ is selected from methyl, ethyl, n-propyl, i-butyl, allyl, methoxyethyl, cyclopropyl, cyclopropylmethyl, tetrahydrofuranylmethyl-, pyrrolidinylethyl-, piperidinylethyl-, morpholinylethyl-, and thiophenylmethyl-; and, R$^5$ is —C(O)R$^6$.

The present invention also provides a novel method, wherein:

R is selected from H, methyl, and ethyl;

R$^1$ and R$^2$ are independently methyl, ethyl, allyl, propargyl, i-propyl, n-propyl, cyclopropyl, cyclopropylmethyl, and n-butyl;

X is 3-pyridyl substituted in the 6 position with Z;

Z is selected from (C$_4$-C$_{10}$)heterocycle and —NR$^4$R$^5$;

R$^4$ is selected from methyl, ethyl, cyclopropyl, and cyclopropylmethyl;

R$^5$ is —C(O)R$^6$;

R$^6$ is (C$_5$-C$_6$) heteroaryl optionally substituted with 1, 2 or 3 substituents independently selected from halo, cyano, nitro, halo(C$_1$-C$_4$)alkyl, —C(O)R$^a$, —COOR$^a$, and —C(O) NR$^b$R$^c$;

R$^a$ is selected from H, methyl, ethyl, propyl, and isopropyl; and,

R$^b$ and R$^c$ are independently selected from H, methyl, ethyl, propyl, isopropyl, and cyclopropyl.

The present invention also provides a novel method, wherein the compound is selected from:

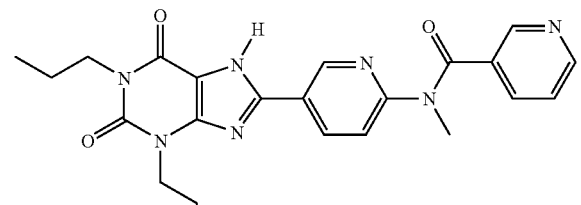

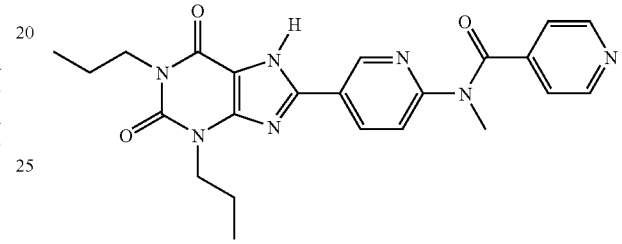

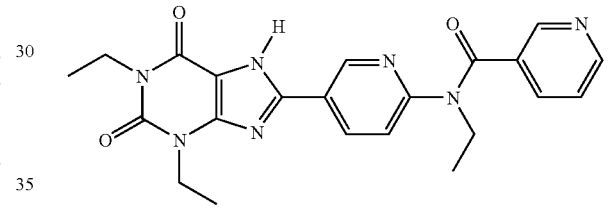

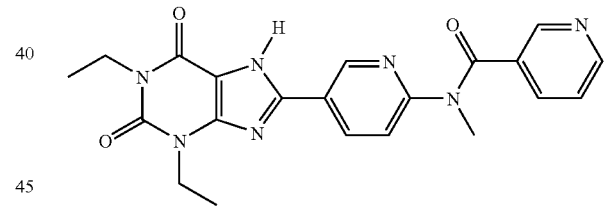

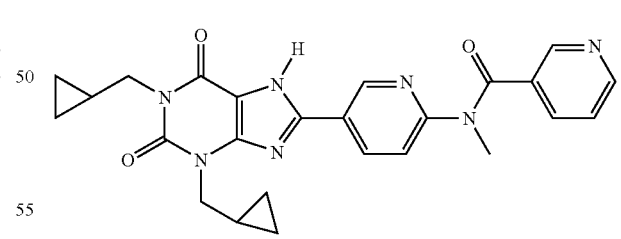

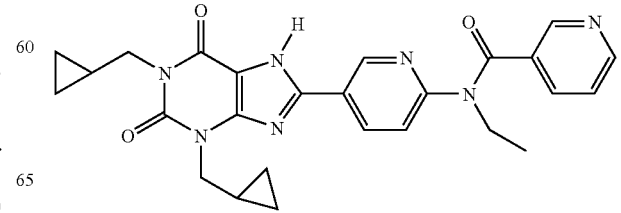

11
-continued
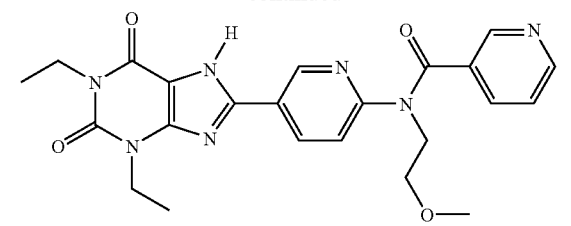
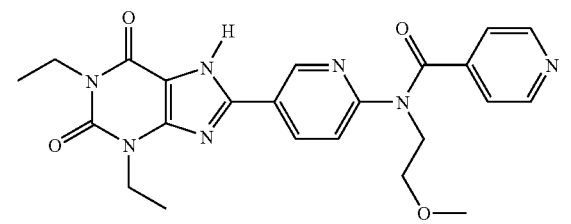
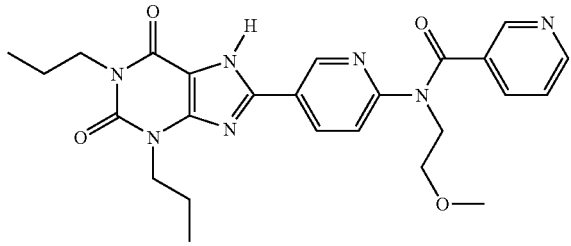
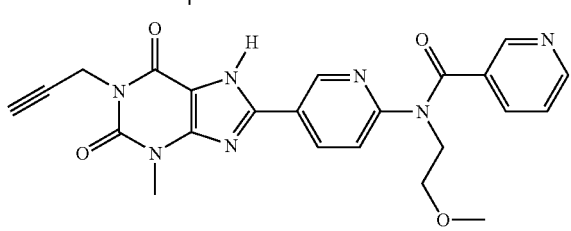
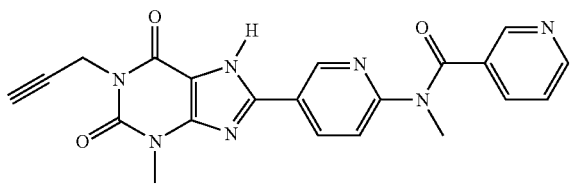
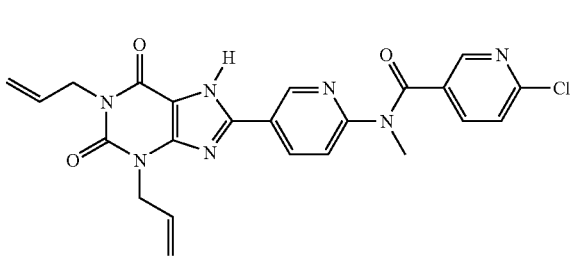
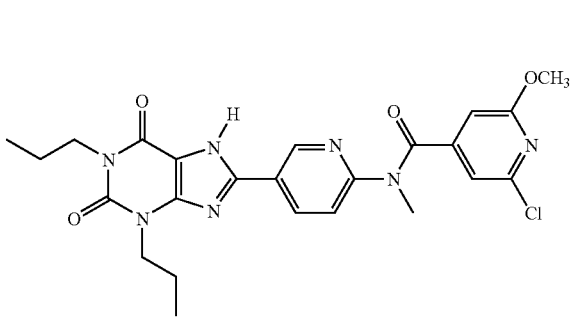
12
-continued
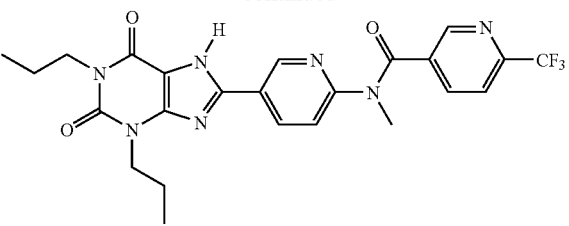
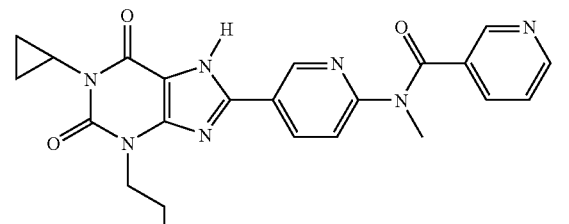
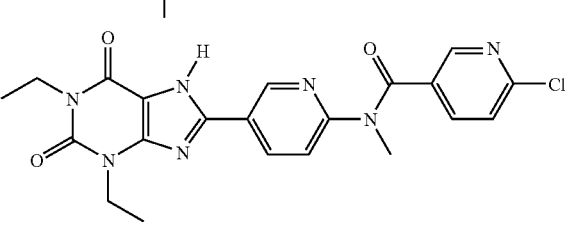
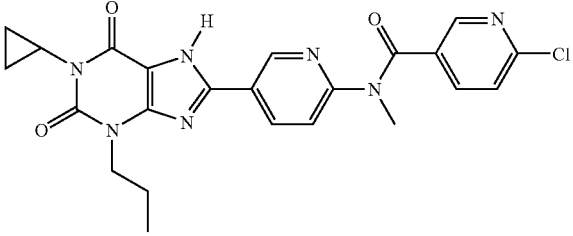
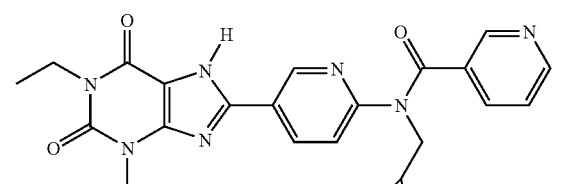
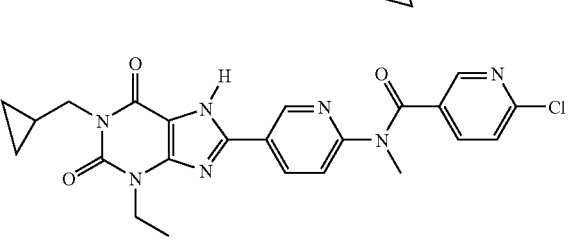
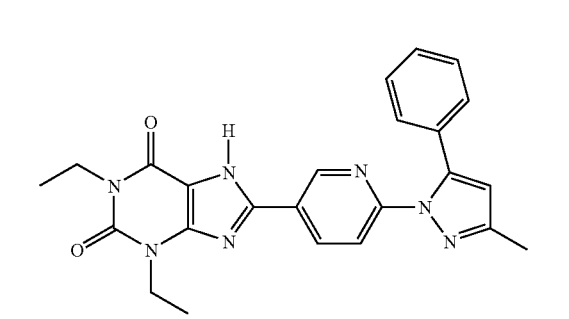

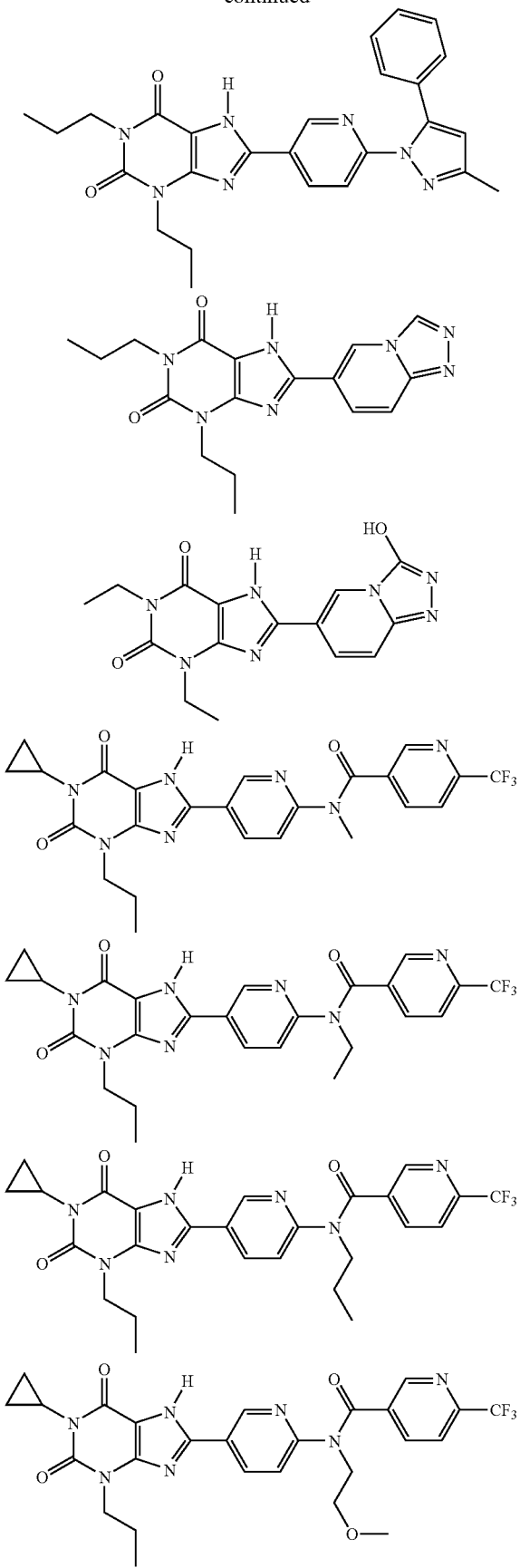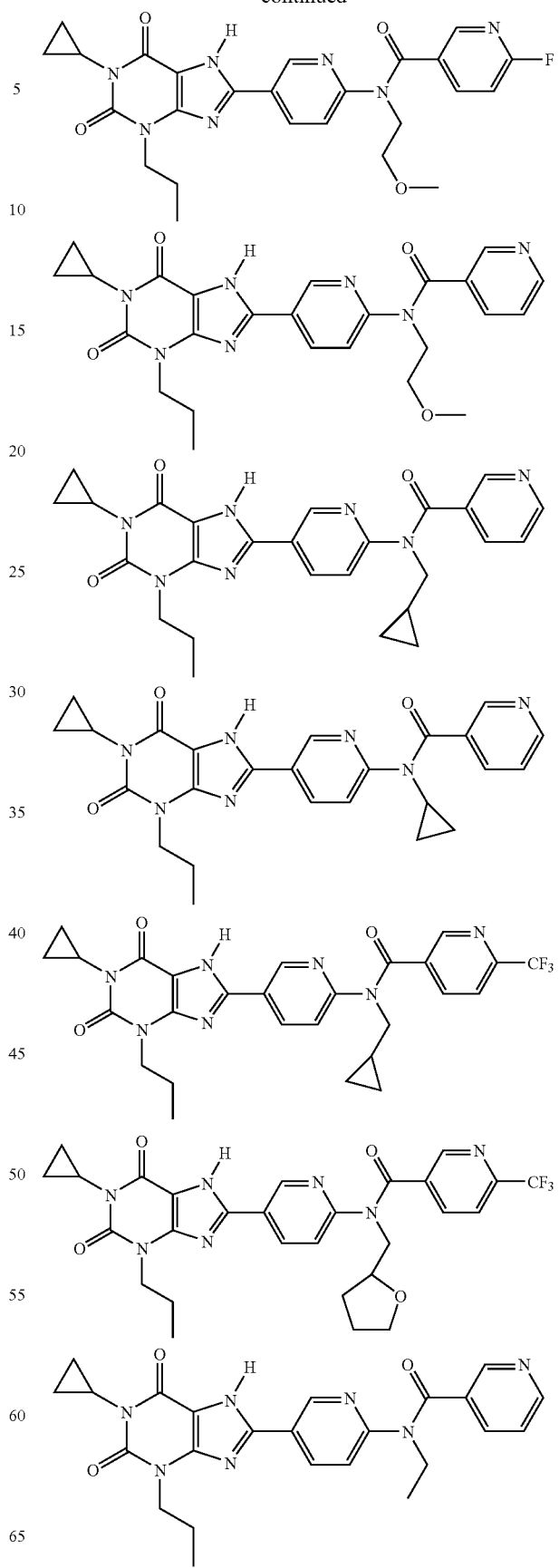

15
-continued
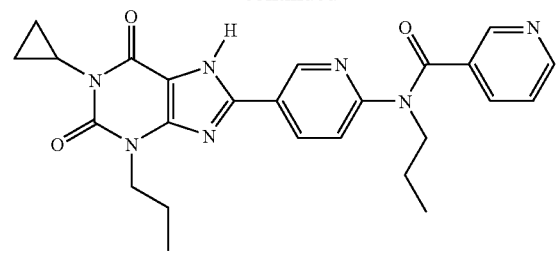
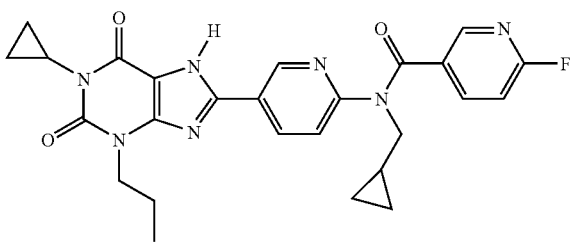
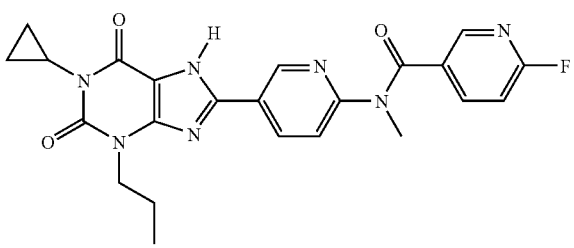
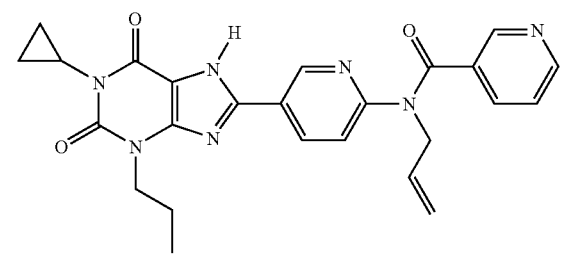
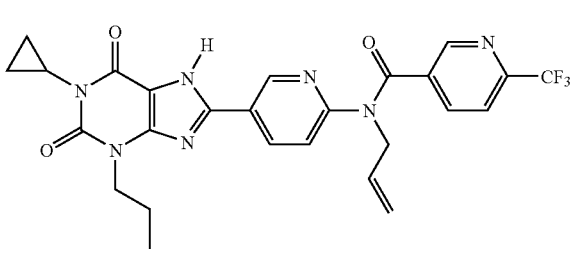
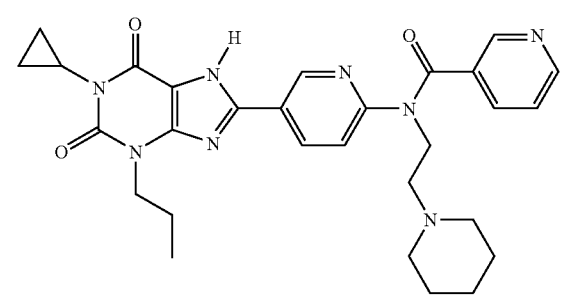
16
-continued
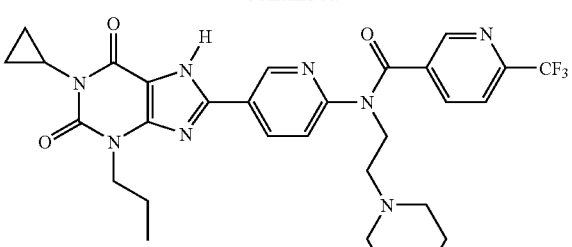
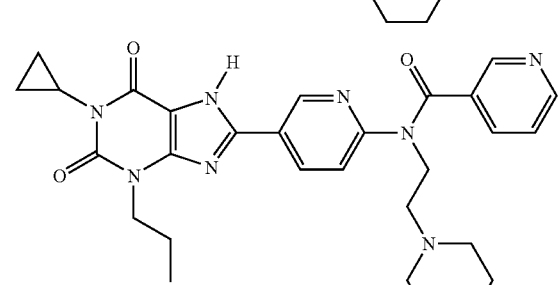
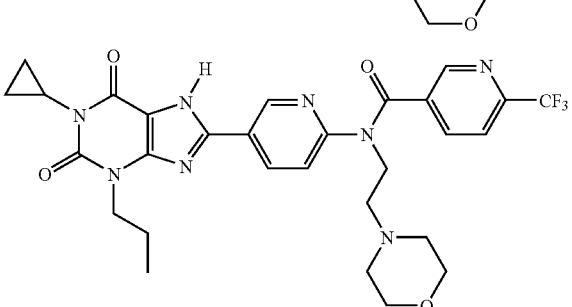
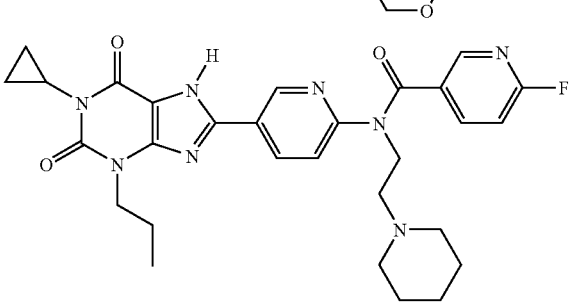
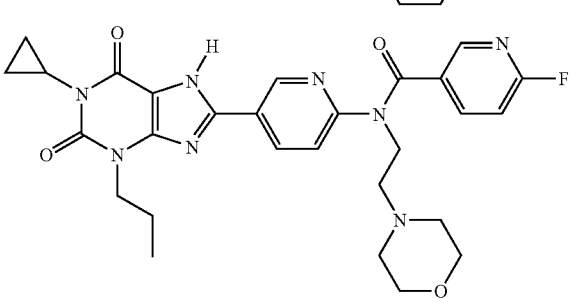
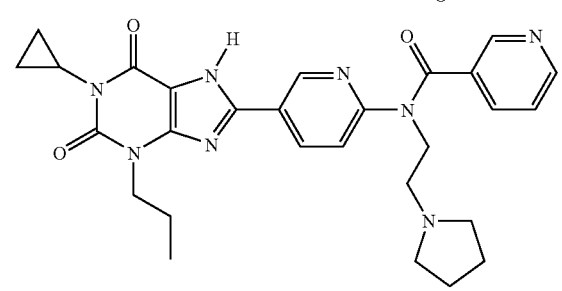

-continued

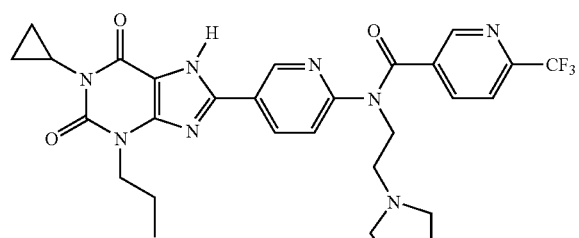
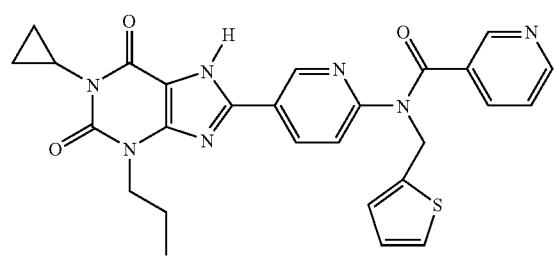
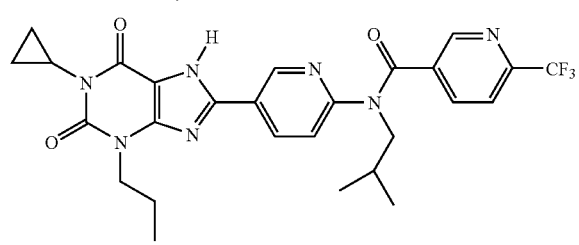
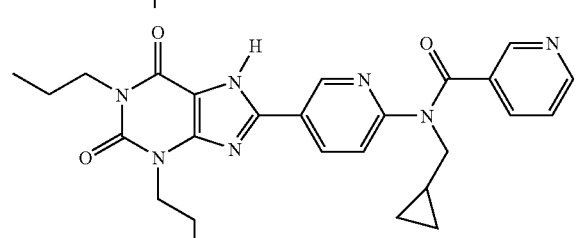
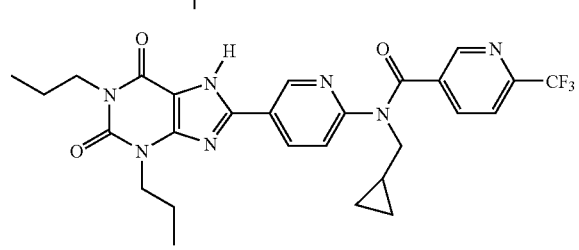
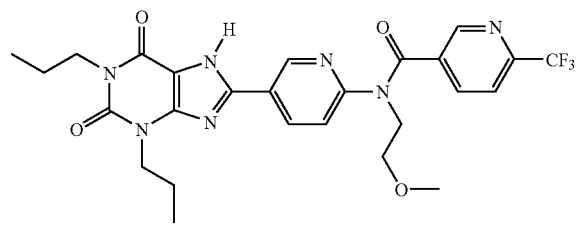
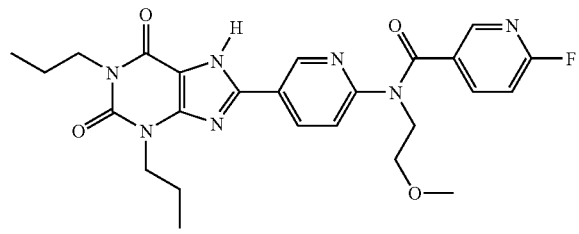

-continued

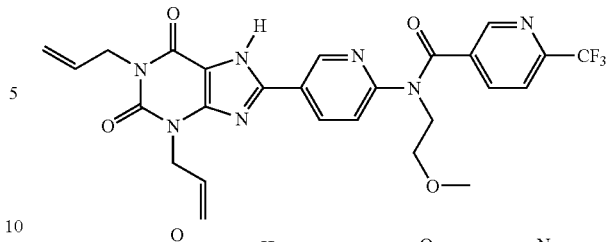
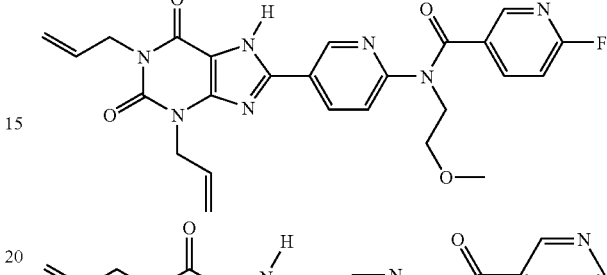
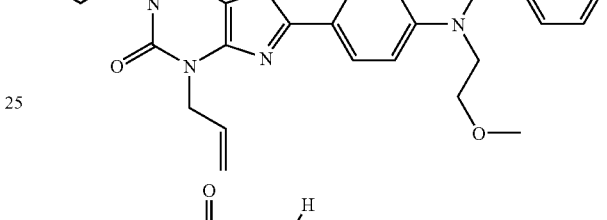
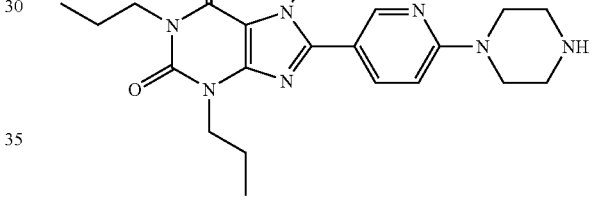
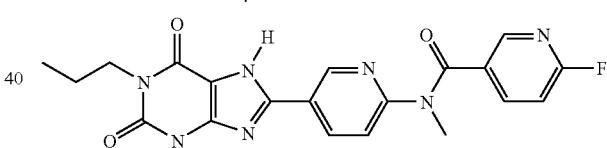
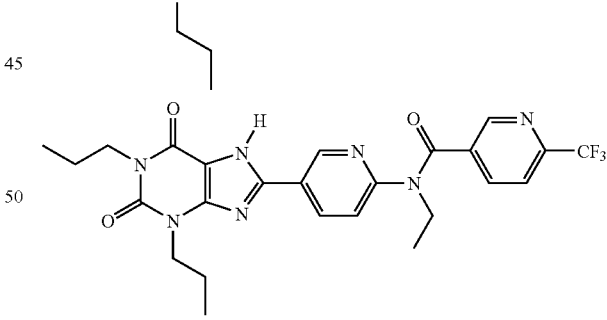

or a pharmaceutically acceptable salt thereof.

It is understood that any embodiment or feature of the present invention whether characterized as preferred or not characterized as preferred may be combined with any other embodiment or feature of the invention, whether such other feature is characterized as preferred or not characterized as preferred.

As is recognized by one of ordinary skill in the art, the imidazole ring of some of the $A_{2B}$ antagonists may exist in tautomeric forms or as tautomers, and thus are also included within the scope of the invention. The tautomeric isomers are represented as the structures (I') and (I"):

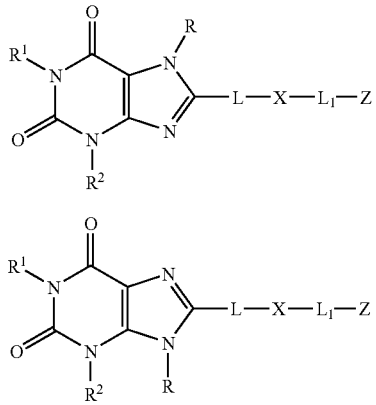

wherein R, $R^1$, $R^2$, L, $L_1$, X, and Z are as defined herein. By naming or referring to one compound, for example, it is understood for the purposes of the present application that its corresponding tautomer is also intended.

The terms "include", "for example", "such as", and the like are used illustratively and are not intended to limit the present invention.

The indefinite articles "a" and "an" mean "at least one" or "one or more" when used in this application, including the claims, unless specifically indicated otherwise.

$A_{2B}$ antagonist refers to an agent that antagonizes the Adenosine $A_{2B}$ receptor with a Ki of <1 µM. An $A_{2B}$ antagonist may be selective for $A_{2B}$ (e.g., at least 10, 50, or 100/1 an other adenosine receptor subtype/$A_{2B}$ receptor). An $A_{2B}$ antagonist may also be cross reactive with other adenosine receptor subtypes (e.g., $A_1$, $A_{2A}$, and $A_3$). The $A_{2B}$ antagonist may antagonize other receptors with a greater or lesser affinity than the $A_{2B}$ receptor.

It will be appreciated by those skilled in the art that compounds of the invention having a chiral center may exist in and be isolated in optically active, and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein; it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine therapeutic activity using the standard tests described herein or using other similar tests which are well known in the art.

Examples of the molecular weight of compounds useful in the present invention can include (a) less than about 500, 550, 600, 650, 700, 750, 800, 850, 900, 950, or 1000 grams per mole; (b) less than about 950 grams per mole; (c) less than about 850 grams per mole, and, (d) less than about 750 grams per mole.

The term "substituted" means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties.

Stable means that the compound is suitable for pharmaceutical use.

The present invention covers stable compounds and thus avoids, unless otherwise specified, the following bond types: heteroatom-halogen, N—S, O—S, O—O, and S—S.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

"Alkyl" includes both branched and straight-chain saturated aliphatic hydrocarbon groups having the specified number of carbon atoms. $C_{1-6}$ alkyl, for example, includes C1, $C_2$, $C_3$, $C_4$, $C_5$, and $C_6$ alkyl groups. Examples of alkyl include methyl, ethyl, n-propyl, i-propyl, n-butyl, i-butyl, s-butyl, t-butyl, n-pentyl, and s-pentyl.

"Haloalkyl" includes both branched and straight-chain saturated aliphatic hydrocarbon groups having the specified number of carbon atoms, substituted with 1 or more halogen (for example—$C_vF_w$ where v=1 to 3 and w=1 to (2v+1)). Examples of haloalkyl include, but are not limited to, trifluoromethyl, trichloromethyl, pentafluoroethyl, and pentachloroethyl.

"Hydroxyalkyl" includes both branched and straight-chain saturated aliphatic hydrocarbon groups having the specified number of carbon atoms, substituted with 1 or more hydroxy groups (e.g., 1, 2, or 3 OH). Examples of hydroxyl alkyl include hydroxymethyl, hydroxyethyl, and hydroxy-n-propyl.

"Alkoxy" is an alkyl-O-group.

"Alkenyl" includes the specified number of hydrocarbon atoms in either straight or branched configuration with one or more unsaturated carbon-carbon bonds that may occur in any stable point along the chain, such as ethenyl and propenyl. $C_{2-6}$ alkenyl includes $C_2$, $C_3$, $C_4$, $C_5$, and $C_6$ alkenyl groups.

"Alkynyl" includes the specified number of hydrocarbon atoms in either straight or branched configuration with one or more triple carbon-carbon bonds that may occur in any stable point along the chain, such as ethynyl and propynyl. $C_{2-6}$ Alkynyl includes $C_2$, $C_3$, $C_4$, $C_5$, and $C_6$ alkynyl groups.

"Cycloalkyl" includes the specified number of hydrocarbon atoms in a saturated ring, such as cyclopropyl, cyclobutyl, cyclopentyl, cyclohexyl, cycloheptyl, and cyclooctyl. $C_{3-8}$ cycloalkyl includes $C_3$, $C_4$, $C_5$, $C_6$, $C_7$, and $C_8$ cycloalkyl groups. Cycloalkyl also include bicycloalkyl and tricycloalkyl, both of which include fused and bridged rings (e.g., norbornane and adamantane).

"Halo" or "halogen" refers to fluoro, chloro, bromo, and iodo.

"Aryl" refers to any stable 6, 7, 8, 9, 10, 11, 12, or 13 membered monocyclic, bicyclic, or tricyclic ring, wherein at least one ring, if more than one is present, is aromatic. Examples of aryl include fluorenyl, phenyl, naphthyl, indanyl, and tetrahydronaphthyl.

"Heteroaryl" refers to any stable 5, 6, 7, 8, 9, 10, 11, or 12 membered, (unless the number of members is otherwise recited), monocyclic, bicyclic, or tricyclic heterocyclic ring that is aromatic, and which consists of carbon atoms and 1, 2, 3, or 4 heteroatoms independently selected from the group consisting of N, O, and S. If the heteroaryl is defined by the number of carbons atoms, then 1, 2, 3, or 4 of the listed carbon atoms are replaced by a heteroatom. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), S(O)$_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable.

Examples of heteroaryl include acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, pyranyl, pyrazinyl, pyrazolyl, pyridazinyl, pyridooxazole, pyridoimidazole, pyridothiazole, pyridinyl, pyridyl, pyrimidinyl, 2H-pyrrolyl, pyrrolyl, quinazolinyl, quinolinyl, 4H-quinolizinyl, quinoxalinyl, quinuclidinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

"Heterocycle" refers to any stable 4, 5, 6, 7, 8, 9, 10, 11, or 12 membered, (unless the number of members is otherwise recited), monocyclic, bicyclic, or tricyclic heterocyclic ring that is saturated or partially unsaturated, and which consists of carbon atoms and 1, 2, 3, or 4 heteroatoms independently selected from the group consisting of N, O, and S. If the heterocycle is defined by the number of carbons atoms, then from 1, 2, 3, or 4 of the listed carbon atoms are replaced by a heteroatom. If the heterocycle is bicyclic or tricyclic, then at least one of the two or three rings must contain a heteroatom, though both or all three may each contain one or more heteroatoms. The N group may be N, NH, or N-substituent, depending on the chosen ring and if substituents are recited. The nitrogen and sulfur heteroatoms optionally may be oxidized (e.g., S, S(O), S(O)$_2$, and N—O). The heterocycle may be attached to its pendant group at any heteroatom or carbon atom that results in a stable structure. The heterocycles described herein may be substituted on carbon or on a nitrogen atom if the resulting compound is stable.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Mammal and patient covers warm blooded mammals that are typically under medical care (e.g., humans and domesticated animals). Examples of mammals include (a) feline, canine, equine, bovine, and human and (b) human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 18th ed., Mack Publishing Company, Easton, Pa., 1990, p 1445, the disclosure of which is hereby incorporated by reference.

"Therapeutically effective amount" includes an amount of a compound of the present invention that is effective when administered alone or in combination to an indication listed herein. "Therapeutically effective amount" also includes an amount of the combination of compounds claimed that is effective to treat the desired indication. The combination of compounds is preferably a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased effect, or some other beneficial effect of the combination compared with the individual components.

Specific and preferred values listed for radicals, substituents, and ranges, are for illustration only; they do not exclude other defined values or other values within defined ranges for the radicals and substituents.

SYNTHESIS

The compounds of the present invention can be prepared by the methods described in US2005/0065341, the contents of which are incorporated herein by reference.

The compounds of the present invention can also be prepared by the methods described in P. J. Scammells, et al., *J. Med. Chem.* 37, 2704-2712 (1994). A diamino-1,3-disubstituted uracil is acylated with 6-chloronicotinoyl chloride in pyridine at 5° C. to provide the compounds of Formula (5a). The resulting amide (5a) is cyclized by refluxing in an aqueous sodium hydroxide solution to provide the compound IA. 6-Chloronicotinoyl chloride is prepared by refluxing 6-hydroxynicotinic acid in thionyl chloride using DMF as the catalyst as shown in Reaction Scheme 1.

Compound A can be alkylated with alkyl bromide or iodide to provide compounds of Formula $A^1$. Compounds A or $A^1$ react with substituted amine at 150-160° C. in a pressure tube to give compounds of Formula B or $B^1$. Compounds of Formula B1 where $R^4$ is hydrogen can react with acyl chloride to afford compounds where $R^4$ is —C(O)$R^6$ (C).

REACTION SCHEME 1

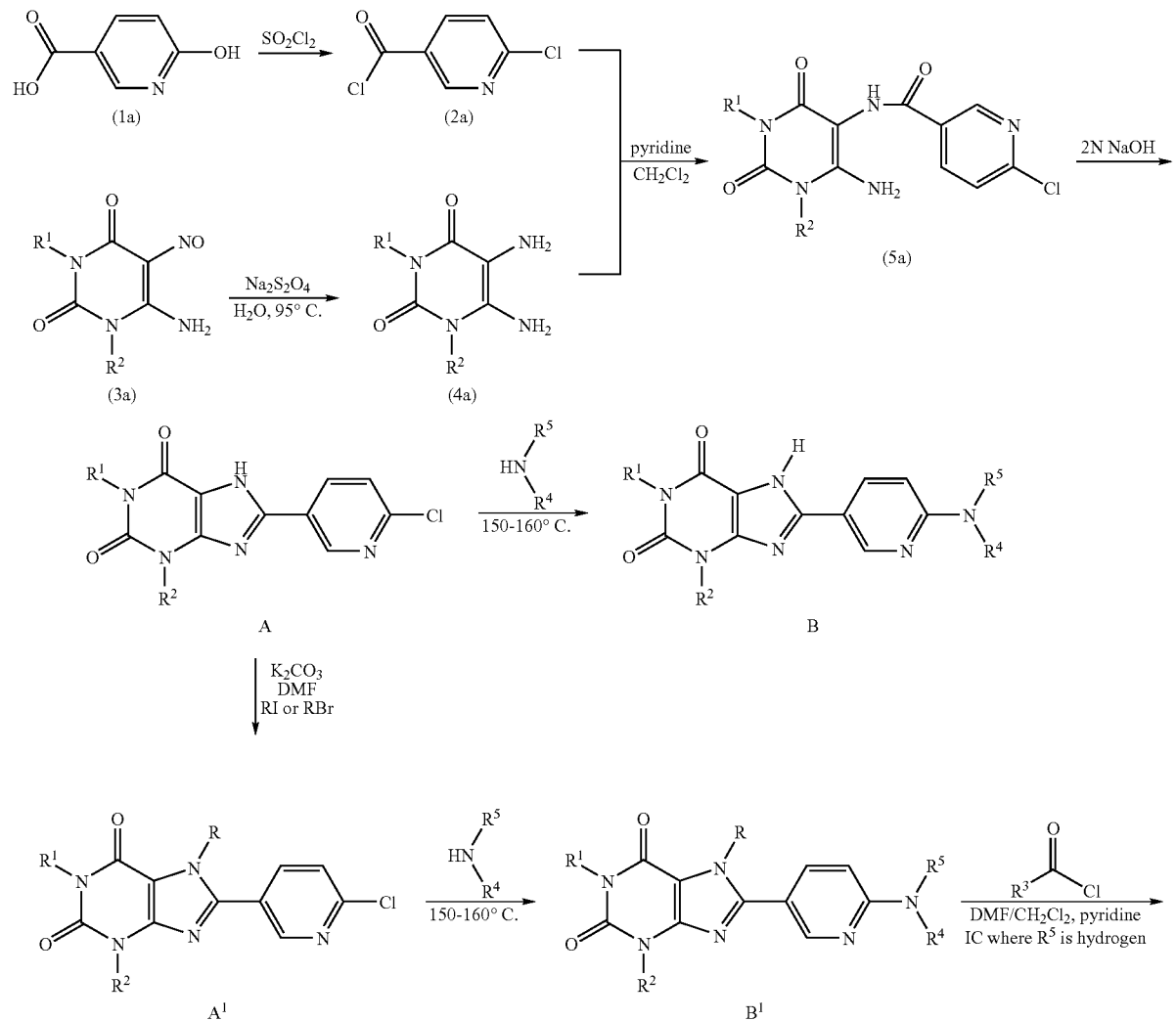

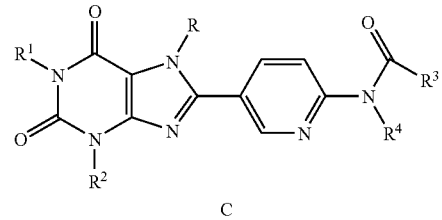

C

The following abbreviations have been used herein:

| | |
|---|---|
| [$^{125}$I]ABA | [$^{125}$I]N$^6$-(4-aminobenzyl)-adenosine |
| $^{125}$I-ABOPX | $^{125}$I-3(4-amino-3-iodobenzyl)-8-oxyacetate-1-propyl-xanthine |
| AR | adenosine receptor |
| CGS 21680 | 2-[4-[(2-carboxyethyl)phenyl]ethyl-amino]-5'-N-ethylcarbamoyl adenosine |
| CPX | 8-cyclopentyl-1,3-dipropylxanthine |
| DMEM | Dulbecco modified eagle medium |
| DMF | N,N-dimethylformamide |
| DMSO | dimethylsulfoxide |
| EDTA | ethylenediaminetetraacetate |
| HEK cells | human embryonic kidney cells |
| $K_i$ | equilibrium inhibition constant |
| NECA | 5'-(N-ethylcarbamoyl)adenosine |
| R-PIA | R-N$^6$-phenylisopropyladenosine |
| TEA | triethylamine |
| TLC | Thin layer chromatography |
| ZM 241385 | 4-(2-[7-amino-2-{furyl}{1,2,4}triazolo{2,3-a}{1,3,5}triazin-5-ylaminoethyl)phenol |

The compounds of the present invention can be formulated as pharmaceutical compositions and administered to a mammalian host, such as a human patient in a variety of forms adapted to the chosen route of administration, e.g., orally or parenterally, by intravenous, intramuscular, topical, inhalation or subcutaneous routes. Exemplary pharmaceutical compositions are disclosed in "Remington: The Science and Practice of Pharmacy", A. Gennaro, ed., 20th edition, Lippincott, Williams & Wilkins, Philadelphia, Pa.

Thus, the present compounds may be systemically administered, e.g., orally, in combination with a pharmaceutically acceptable excipient such as an inert diluent or an assimilable edible carrier. They may be enclosed in hard or soft shell gelatin capsules, may be compressed into tablets or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508). Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the present invention in a liquid composition, such as a lotion, will be from (a) about 0.1-25 wt % and (b) about 0.5-10 wt %. The concentration in a semi-solid or solid composition such as a gel or a powder will be (a) about 0.1-5 wt % and (b) about 0.5-2.5 wt %.

The amount of the compound or an active salt or derivative thereof, required for use in treatment will vary not only with the particular compound or salt selected but also with the route of administration, the nature of the condition being treated, and the age and condition of the patient and will be ultimately at the discretion of the attendant physician or clinician. In general, however, a suitable dose will be in the range of from (a) about 1.0-100 mg/kg of body weight per day, (b) about 10-75 mg/kg of body weight per day, and (c) about 5-20 mg per kilogram body weight per day.

The compound can be conveniently administered in unit dosage form; e.g., tablets, caplets, etc., containing (a) about 4-400 mg, (b) about 10-200 mg, and (c) about 20-100 mg of active ingredient per unit dosage form.

Ideally, the active ingredient should be administered to achieve peak plasma concentrations of the active compound of from (a) about 0.02-20 $\mu$M, (b) about 0.1-10 $\mu$M, and (c) about 0.5-5 $\mu$M. These concentrations may be achieved, for example, by the intravenous injection of a 0.005-0.5% solution of the active ingredient, or orally administered as a bolus containing about 4-400 mg of the active ingredient.

The compounds of the invention can also be administered by inhalation from an inhaler, insufflator, atomizer or pressurized pack or other means of delivering an aerosol spray. Pressurized packs may comprise a suitable propellant such as carbon dioxide or other suitable gas. In case of a pressurized aerosol, the dosage unit may be determined by providing a value to deliver a metered amount. The inhalers, insufflators, atomizers are fully described in pharmaceutical reference books such as Remington's Pharmaceutical Sciences Volumes 16 (1980) or 18 (1990) Mack Publishing Co.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

All patents, patent applications, books and literature cited in the specification are hereby incorporated by reference in their entirety. In the case of any inconsistencies, the present disclosure, including any definitions therein will prevail.

The invention has been described with reference to various specific and preferred embodiments and techniques. However, it should be understood that many variations and modifications may be made while remaining within the spirit and scope of the invention.

EXAMPLES

Reagents: Adenosine (Research Biochemicals Int., Natick, Mass.), Reagents for SDS-PAGE, nitrocellulose membranes (0.45-$\mu$m pores) and horseradish peroxidase-conjugated IgG (Bio-Rad, Hercules, Calif.), Piroxicam (Sigma Aldrich, St. Louis, Mo.), Isobutylmethylxanthine (IBMX, Biomol Research Laboratories Inc, Plymouth Meeting, Pa.), cAMP-Screen Kit (Applied Biosystems Bedford, Mass.), Dextran sodium sulphate (DSS, MP Biomedicals Inc, Aurora, Ohio), IL-6 and KC Duoset ELISA kit (R&D systems Inc, Minneapolis, Minn.). ATL-801, an A2b receptor specific inhibitor from Dr. J Linden, (Adenosine Therapeutics University of Virginia, Charlottesville, Va.). The diet containing the ATL-801 inhibitor was obtained from Harlan Tekad Research Diets (Madison, Wis.). Antibodies Ki67 (Novocastra, UK), cleaved Caspase 3 (Cell Signaling, Denvers, Mass.), A2bR (Alpha diagnostics, San Antonio, USA), TUNEL assay kit (Roche Applied Science, Indianapolis, Ind.).

Electrophysiology Studies

Electrophysiologic studies were performed as described previously Mice were euthanized by $CO_2$/hypothermia. The colon was removed and opened along the mesenteric border. The colon was then stripped of its external muscle by blunt dissection. A of mucosa from distal colon was used for Using chamber studies. After a sustained baseline Isc, mucosal layers were stimulated with adenosine (100 $\mu$M) and forskolin (FSK 10 $\mu$M). Antagonist was added to both bathing solutions before stimulating with adenosine.

Experimental Animals

Age and sex matched 6-week-old C57BL6 and IL-10$^{-/-}$ were purchased from Jackson Laboratories (Bar Harbor, Me.) and bred at our facility. IL-10$^{-/-}$ mice used in the study were 6-7-weeks-old at the beginning of the experimental protocol. C57BL6 mice were used for DSS treatment. They were maintained on a 12 hour dark-light cycle and allowed free access to powdered or pelleted diet and tap water under conditions of controlled temperatures (25±2° C.). The Animal Care Committee of the Emory University, Atlanta Ga., approved all procedures performed on animals.

Induction of DSS-Colitis

Colitis was induced in male C57BL/6 mice by oral administration of DSS (molecular wt. 50000; ICN Biomedicals, Aurora, Ohio) at 3% (wt/vol) in tap water ad libitum for 6 days. Age-matched male wild-type C57BL6 mice receiving tap water served as controls. Mice were observed daily and evaluated for changes in body weight and development of clinical symptoms. Mice were given ATL-801 10 mg/Kg diet approximately 20 µg/day/mice) during the administration of DSS.

Piroxicam Induced Colitis

IL-10$^{-/-}$ mice spontaneously develop a chronic, T-cell mediated, transmural colitis that shares many features with human Crohn's disease. Based on this model, there have been several clinical trials using IL-10 treatment for IBD in human patients 13 However, due to the inconsistency in the development of spontaneous colitis in IL-10$^{-/-}$ mice, Berg and his colleagues have described rapid development of colitis in IL-10$^{-/-}$ mice treated with a nonsteroidal anti-inflammatory drug piroxicam (NSAID)[9]. Accordingly, mice were treated with piroxicam, 200 mg/kg diet, for two weeks to induce colitis. Mice were administered ATL-801 for a week prior to treatment with piroxicam, and ATL-801 treatment was continued during piroxicam administration. Two weeks after the induction of colitis, mice were euthanized, and colonic tissue was analyzed.

Clinical Score and Histological Scoring

Assessment of body weights, stool consistency, and the presence of occult/gross blood by a guaic test (Hemoccult Sensa; Beckman Coulter, Fullerton, Calif.) were performed daily for each mouse. Colitis was quantified with a clinical and histological score, as described by Cooper, et. al. Clinical score was based on weight loss, stool consistency, and fecal blood (score range 0-12). Histological scoring was performed based on three variables, extent of inflammatory infiltrate, mucosal ulcers and severity of crypt (score range 0-11). IL-10$^{-/-}$ mouse colon histological scoring (ranging from 0 to 4) was performed as described by Berg, et. al. to assess intestinal lesions and their severity.

Cytokine Measurements

In the DSS-model proinflammatory cytokines were measured by real time PCR. Total RNA was extracted from DSS treated, DSS+ATL-801 and control colonic tissue using the TRizol reagent. After quantification, a reverse transcription (RT) reaction was performed with 2 µg of each sample and oligo-dT primer, using the SuperScript First strand synthesis system for RT-PCR (Invitrogen, CA). The real-time iCycler sequence detection system (Bio-Rad) was used for the real-time RT-PCR. Briefly, 3 ng of reverse transcribed cDNA, 500 nM of gene-specific primers and the iQ SYBR Green Supermix (Biorad, Hercules, Calif.) were amplified at 50° C. for 2 min and 95° C. for 10 min, followed by 40 cycles of 95° C. for 15 s and 60° C. for 1 min. The 36B4 expression levels were used as reference, and fold-induction was calculated using a standard curve. For graphical representation of quantitative PCR data, raw cycle threshold values (Ct values) obtained for treated mice were deducted from the Ct value obtained for internal 36B4 transcript levels, using the Ct method as follows: $\Delta\Delta CT=$(Ct Target–Ct 36B4)treatment–(Ct Target–Ct 36B4) no treatment, and the final data were derived from $2^{-\Delta\Delta CT}$. Primers used: IL-6 sense 5'-ACA AGT CGG AGG CTT AAT TAC ACA T-3' (SEQ ID NO:1) antisense 5'-TTG CCA TTG CAC AAC TCT TTT C-3' (SEQ ID NO:2), MIP-2 sense 5AGT GAA CTG CGC TGT CAA TGC-3' (SEQ ID NO:3) antisense 5' AGG CAA ACT TTT TGA CCG CC 3' (SEQ ID NO:4). In IL-10–/– model proinflammatory cytokines were measured by ELISA in organ cultures. Colon organ cultures were prepared from IL-10$^{-/-}$ mice with and with out ATL-801 along with piroxicam. Colons were dissected from mice and flushed with cold PBS to remove fecal matter. Each colon was cut in to 1 cm length and washed in HBSS with pencillin/streptomycin and cultured in serum free RPMI-1640 supplemented with penicillin and streptomycin. Cultures were incubated at 37° C. in 5% $CO_2$. Supernatants were harvested after 24 hours, centrifuged and stored at –80° C. before IL-6 and keratinocyte derived chemokine, KC levels were measured by ELISA. T84 cells were plated on plastic. After reaching confluency, cells were pretreated with or without ATL-801 (100 µM) for 30 minutes and then treated with flagellin (100 ng/ml) for 5 hours. IL-8 was measured in the supernatants by ELISA.

Myeloperoxidase Assay

Neutrophil infiltration into colon was quantified by measuring myeloperoxidase (MPO) activity as described previously. One unit of MPO activity was defined as the amount that degraded 1 µmol of peroxidase per minute at 25° C. The results were expressed as absorbance per µg of protein.

cAMP Measurement

T84 cells were stimulated with adenosine (100 µM) or forskolin (10 µM) for 7 min, with or without ATL-801 (100 µM). Total cell lysates were processed in the presence of IBMX (phosphodiesterase inhibitor). cAMP levels were measured in whole cell lysates using a competitive cAMP immunoassay kit (Applied Biosystems, Bedford, Mass.) according to the manufacturer's instructions. Luminescence was read with a Luminoscan Ascent plate reader (Thermo Labsystems, Needham Heights, Mass.).

Apoptosis: Apoptotic cells were determined in colonic crypts of the mice that received ATL-801. Apoptotic cells were identified by fluorescent double staining using caspase-3 and terminal deoxyuridine nick-end labeling (TUNEL) as a secondary method to detect apoptosis. After deparaffinization and hydration, paraffin sections of colon were retrieved for antigens in a pressure cooker with sodium citrate (pH 6.0, 10 mM) for 10 min. After cooling, the sections were quenched in 3% $H_2O_2$ in methanol and then blocked with normal goat serum. Caspase-3 was detected with rabbit anti-cleaved-caspase-3 IgG overnight at 4° C. followed by a labeled streptavidin-biotin (LSAB) staining method consisting of successive application of secondary antibody-streptavidin, biotin-horseradish peroxidase, and cyanine-3 tyramide. TUNEL immunohistochemistry was performed using the in situ cell death detection kit, fluorescein, as described by the manufacturer (Roche Applied Science, Indianapolis, Ind.). For IL-10 model, frozen sections were used to stain cleaved caspase 3 and TUNEL. Nuclei were attained by Hoechst to count total crypt cell number. The apoptotic index for both morphologically defined apoptotic cells and fluorescent staining with caspase-3 was calculated as the number of apoptotic cells per crypt.

Immunohistochemistry: Immunohistochemical staining was carried out using Vectastain ABC kit (Vector laboratories Inc) according to manufacturer's protocol. In order to perform the standard staining procedure, tissue sections were deparaffinized and rehydrated. Paraffin sections of colon were retrieved for antigens in a pressure cooker with sodium citrate (pH 6.0, 10 mM) for 10 min before the application of primary A2bR and ki67:antibody (1:500 dilution, incubated 40 overnight). Enzyme-conjugated secondary antibodies were applied and the specific staining was visualized after the addition of the enzyme-specific substrate. These tissues were counterstained by hemotoxylin.

Statistical Analysis

The data are presented as mean ±SE. Statistical analysis was conducted using Student's t-test where $p<0.05$ was considered significant.

A2b receptor antagonist ATL-801 inhibits adenosine-mediated cAMP and chloride secretion: T84 model colonic epithelial cell monolayers were treated with adenosine (100 µM) with or without ATL-801 (100 µM). As shown in FIG. 1A, ATL-801 significantly inhibited adenosine mediated cAMP levels (unstimulated: 1.7±0.05, adenosine alone: 4.7±0.66, adenosine+ATL-801: 0.2±0.06 pmoles/$10^6$ cells p<0.002, n=6, FIG. 1A). To determine the effect of ATL-801 on adenosine-induced chloride secretion, mucosal stripping from mouse colon was placed on Using chamber and baseline Isc was measured with resistance 40 $\Omega \cdot cm^2$. Stimulation of the mouse colonic mucosa with adenosine (100 µM) showed a steady increase in Isc which peaked within 5 min and showed a maximum Δ Isc of 10 µA, as shown in FIG. 1B. ATL-801 abolished adenosine-induced Isc (FIG. 1C). However, as shown in FIG. 1C, ATL-801 did not affect forskolin, a direct activator of adenylate cyclase, mediated Δ Isc (ΔIsc: Adenosine alone=7.9 µA, ATL-801+Adenosine=1.9 µA, ATL-801+FSK=10 µA). Together, these data demonstrate that ATL-801 is a potent inhibitor of adenosine-mediated cAMP response and Isc. Further, these data demonstrate that ATL-801 is specific to adenosine-induced Isc and does not affect other cAMP-dependent Isc responses.

A2b receptor antagonist ATL-801 inhibits flagellin-induced IL-8 secretion: In order to assess the effect of A2b receptor antagonist on cytokine secretion in response to proinflammatory molecules, T84 cells were treated with ATL-801 (100 µM) for 30 minutes and then treated with flagellin (100 ng/ml) for 5 hours. Media was collected and IL-8 was measured by ELISA. As shown in FIG. 2, ATL-801 inhibited flagellin-induced IL-8 secretion by 60% (control: 206±18.5, Flagellin: 1126±, 88.05, Flagellin+ATL-801: 769±13.6, ATL-801 alone: 101±34.6 µg IL-8/ml, p<0.007, n=3). These data demonstrate that ATL-801 downregulates in vitro IL-8 secretion.

A2b receptor antagonist attenuates DSS-induced colitis: To investigate if A2b receptor plays a role in the pathogenesis of intestinal inflammation, the DSS model of colitis was used. Mice received ATL-801 10 mg/Kg in the diet. Control mice received normal drinking water and diet containing ATL-801 alone. The mice were compared for the clinical signs of weight change, stool consistency, and occult blood. All mice exposed to DSS alone developed signs of colitis between days 5 and 6. As shown in the FIGS. 3A&B, the mice receiving DSS alone had a clinical disease activity score of 9.4±1.1. These mice had significant weight loss (5.9±0.6%), frank blood in stool and diarrhea. In contrast, mice given DSS and ATL-801 showed a significantly lower clinical score of 4.4±1.5 (p<0.003). Notably, mice given A2b receptor antagonist along with DSS had solid stools in contrast to DSS-fed mice, which had watery diarrhea. Dissection of the colon of mice fed A2b antagonist showed colon with solid stool pellets, which is reflected in their colon weight (0.48±0.03 g) when compared to DSS fed mice, which had no stool in the colon (0.26±0.03 g, p<0.03 n=5). Together, these data demonstrated protection from DSS induced acute colitis when A2b receptor signaling and function was inhibited. Mice given ATL-801 alone did not show any adverse affects on clinical score.

Reduction of the colon length, which is used as a parameter of inflammation, correlated with the clinical results. After the 6-day experimental period, mice exposed to DSS alone experienced a 30% shortening of the colon length when compared to control mice. Administration of DSS in the presence of A2b receptor antagonist (10 mg/Kg) inhibited colon shortening (6.04±0.16 cm for antagonist compared to 4.5±0.26 cm in DSS alone), in the group not administered DSS, there was no significant difference between the colon lengths of mice given antagonist or vehicle (7.5, 6.5±0.25 respectively).

DSS— induced colitis is characterized by the presence of inflammation of the colon manifested by crypt destruction, mucosal damage, epithelial erosions, and infiltration of inflammatory cells into the mucosal tissue. Tissues collected from mice exposed to DSS were examined histologically and compared with those from normal controls. Histologic scoring was performed in a blinded fashion as described previously. The data obtained corroborated the results obtained from clinical analysis and confirmed the protective role of A2b receptor antagonist against the development of colitis. As shown in Table 2 and FIG. 4, DSS treated mice exhibited obvious signs of colon inflammation and tissue destruction. These mice had extensive crypt damage, epithelial erosion/ulceration, crypt abscess formation, and infiltration of inflammatory cells in the lamina propria and muscularis mucosa of colonic sections (Table 1, FIG. 4). In contrast, histological analysis of the sections from mice fed A2b receptor antagonist in the diet revealed significantly reduced histological inflammation, and these mice appeared protected from DSS-associated mucosal injury with fewer inflammatory infiltrates and ulcerations (FIG. 4, Table 1). Histological scores of 4.1±1.8 (10 mg/Kg) were observed in mice given antagonist+ DSS compared with a score of 9.1±2.1 in the DSS alone group (p<0.05) (Table 1). Histological signs of inflammation were not detected in the water control groups regardless of whether or not they received the antagonist.

TABLE 1

Histological Assessment of Colitis in Mice with or without ATL-801 after administration of 3% DSS for 6 days.

| Parameter | Water | DSS | DSS + ATL 10 mg/Kg |
|---|---|---|---|
| Crypt Damage | 0 | 2.8 ± 1.5 | 1.9 ± 0.6 |
| Inflammation | 0.4 ± 0.2 | 3.7 ± 0.2 | 1.2 ± 0.2 |
| Ulceration | 0 | 2.6 ± 0.6 | 1.0 ± 1 |
| Total Lesion Score | 0.33 ± 0.27 | 9.1 ± 2.1 | 4.1 ± 1.8* |

Figure 4B:
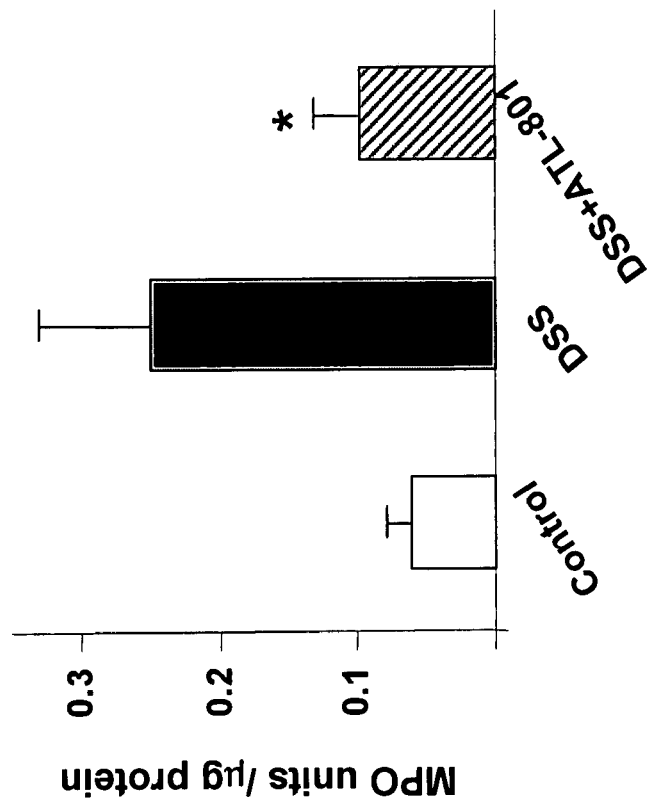

To confirm the histological findings with respect to granulocyte accumulation, the activity of myeloperoxidase (MPO) in the colonic tissue was measured. MPO is an enzyme specific to granulocyte lysosomes, therefore, it directly correlates with the number of neutrophils. Mice fed with DSS alone had significantly increased MPO activity (5 fold, p<0.03) compared with mice given antagonist and DSS (FIG. 4B). Since chronic inflammation is associated with production of pro-inflammatory cytokines such as IL-6,IL-6 mRNA levels were measured in the colonic mucosal tissue of DSS treated mice compared to mice that received DSS along with the antagonist. As shown in FIG. 5A, mice treated with antagonist showed significantly lower IL-6 compared to mice that received DSS alone (DSS: 7.2±1.7, DSS+pATL-801: 1.8±0.7 p<0.01, fold increase compared to untreated). As shown in FIG. 5B, levels of macrophage inflammatory protein-2 (MIP-2, a critical chemokine secreted by macrophages and epithelial cells) were significantly less in ATL-801 treated group (DSS: 28.1±3.8, DSS+ATL-801: 13.62±3.0, p<0.02). Taken together, these data clearly demonstrate that A2b receptor antagonist attenuated not only the clinical characteristics, but also the histologic features associated with DSS-induced colitis.

A2b receptor expression is not affected by the antagonist: Previously it was shown that shown that A2b receptor mRNA and protein expression is upregulated during experimental colitis as well as in patients with active inflammatory bowel disease. In order to determine if ATL-801 affected A2b receptor expression, the effects of A2b receptor antagonist on the A2b receptor level after DSS treatment were studied. Consistent with previous data, it was demonstrated that DSS upregulates A2b receptor levels, as determined by Western blot of colonic lysates (FIG. 6). Administration of A2b receptor antagonist affected neither baseline level of A2b receptor nor DSS-induced increase in A2b receptor expression (FIG. 6).

A2b receptor antagonist enhances proliferation and inhibits apoptosis in DSS-colitis: It was next examined whether inhibition of A2b receptor affects epithelial cell survival in colitis mice. Epithelial cell proliferation was assessed by determining number of cells positive for ki67 and apoptosis was assessed with caspase-3 and TUNEL staining. As shown in FIG. 7A, proliferation index represented by ki67 positive staining showed significant decrease in DSS treated mice compared to DSS+ATL-801 treated mice which is similar to control mice. (control: 18.67±1.62, DSS:5.95±0.31, DSS+ATL:15.13±0.44, control vs DSS p<0.001, DSS vs DSS+ATL-801 p<0.001 n=5). In addition, ATL-801 significantly inhibited apoptosis induced during DSS-colitis. As shown in the FIG. 7B, mice treated with DSS showed more apoptotic positive cells. (DSS:16.3±2.3 and DSS+ATL-801: 3.7±0.7 TUNEL positive cells out of total number of cells counted in each crypt.

A2b receptor antagonist inhibits colitis in IL-10$^{-/-}$ mice: As an alternate model of colitis, the IL-10$^{-/-}$ model was used to study the effect of A2b receptor antagonist on the development of colitis. IL-10$^{-/-}$ mice spontaneously develop a chronic, T-cell mediated, transmural colitis that shares many features with human Crohn's disease However, due to the inconsistency in the development of colitis in IL-10$^{-/-}$ mice, Berg and his colleagues have described rapid development of colitis in IL-10$^{-/-}$ mice treated with a nonsteroidal anti-inflammatory drug, piroxicam. Accordingly, IL-10$^{-/-}$ mice were treated with Piroxicam±ATL-801 (10 mg/Kg) in their diet as described in Methods. Mice were sacrificed at the end of four weeks and colonic tissues were analyzed and histological scoring (ranging from 0 to 4) was performed as described by Berg, et. al. to assess intestinal lesions and their severity. IL-10$^{-/-}$ mice receiving piroxicam showed significant weight loss (Δ−2.05±0.7) while IL-10$^{-/-}$ mice that received piroxicam+ATL-801 showed no weight loss (Δ+0.2±0.5). Microscopic examination revealed marked changes in the colonic mucosa of piroxicam-treated IL-10$^{-/-}$ mice. Further, marked immune cell infiltrates were found in the mucosa and submucosa. Epithelial hyperplasia was common in areas with inflammation. However, IL-10$^{-/-}$ mice treated with ATL-801 showed reduced inflammatory infiltrate as well as epithelial hyperplasia (FIG. 8). The mean histological score was significantly higher in IL-10$^{-/-}$ mice treated with piroxicam group 2.8±1.0 (FIG. 8 upper panel) when compared to the ATL-801 treated groups which showed a histological score of 1.3±0.3. (FIG. 8 lower panel). Control mice as well as mice treated with ATL-801 alone showed normal histology (data not shown). Further, the piroxicam treated group showed significantly reduced colon length 7.0±0.25 cm compared to ATL-801+piroxicam treated group with colon length of 8.4±0.23 cm, p<0.008. Together, these data suggest that inhibition of A2b receptor reduced extent and severity of colitis in IL-10$^{-/-}$ mice.

A2b receptor inhibition suppresses production of pro-inflammatory cytokines: In order to determine the effect of A2b receptor inhibition on pro-inflammatory cytokine synthesis, colonic tissue was obtained from IL-10$^{-/-}$ treated with piroxicam with or without ATL-801. IL-6 and KC was measured in colon culture supernatant as described in the Methods section. IL-6 levels were upregulated in colon cultures of IL-10$^{-/-}$ mice treated with piroxicam alone (1.9±0.3 ng/ml) compared to the ATL-801 treated group (0.46±0.1, p<0.006 and untreated 0.7±0.1, n=3) (FIG. 9A). Similar inhibition of KC secretion was seen in mice treated with piroxicam+ATL-801 (3.7±0.8 ng/ml) compared to piroxicam alone (5.6±0.6 ng/ml) (FIG. 9B). ATL-801 alone had no effect on IL-6 or IL-8 levels (data not shown).

A2b receptor antagonist inhibits proliferation and enhances apoptosis in IL-10−/−colitis: It was further examined the affect of ATL-801 on epithelial cell survival and apoptosis in IL-10$^{-/-}$ model. Epithelial cell proliferation was assessed by determining number of cells positive for ki67 and apoptosis was assessed with caspase-3 and TUNEL staining. As shown in FIG. 10A, proliferation index represented by ki67 positive staining showed significant increase in piroxicam treated mice compared to piroxicam+ATL-801 treated mice. (control:8.0±0.7, piroxicam alone:28.8±2.8, piroxicam+ATL-801: 18.5±1.4, p<0.001, n=4). This inhibition of proliferation inturn reduces hyperplasia. In addition, ATL-801 enhances apoptosis in IL-10$^{-/-}$ model. As shown in the FIG. 10B, mice treated with piroxicam+ATL-801 showed more apoptotic positive cells. (control:4.7±1.5 and piroxicam:4.3±2.3, piroxicam+ATL-801: 10±1.0, TUNEL positive cells out of total (around 500) number of cells counted in each crypt.

Pharmacology

The ability of compounds of the invention to act as an $A_{2B}$ adenosine receptor antagonists can be determined using pharmacological models which are well known to the art or using test procedures described below.

The rat $A_{2B}$ receptor cDNA was subcloned into the expression plasmid pDoubleTrouble using techniques described in Robeva, A. et al., Biochem. Pharmacol., 51, 545-555 (1996). The plasmid was amplified in competent JM109 cells and plasmid DNA isolated using Wizard Megaprep columns (Promega Corporation, Madison, Wis.). $A_{2B}$ adenosine receptors were introduced into HEK-293 cells by means of Lipofectin as described in Feigner, P. L. et al., Proc. Natl. Acad. Sci. USA, 84, 7413-7417 (1987).

Cell Culture

Transfected HEK cells were grown under 5% $CO_2$/95% $O_2$ humidified atmosphere at a temperature of 37° C. Colonies were selected by growth of cells in 0.6 mg/mL G418. Transfected cells were maintained in DMEM supplemented with Hams F12 nutrient mixture (1/1), 10% newborn calf serum, 2 mM glutamine and containing 50 IU/mL penicillin, 50 mg/mL streptomycin, and 0.2 mg/mL Geneticin (G418, Boehringer Mannheim). Cells were cultured in 10 cm diameter round plates and subcultured when grown confluent (approximately after 72 hours).

Radioligand Binding Studies

At $A_{2B}$ receptors. Confluent monolayers of HEK-$A_{2B}$ cells were washed with PBS followed by ice cold Buffer A (10 mM HEPES, 10 mM EDTA, pH 7.4) with protease inhibitors (10 μg/mL benzamidine, 100 μM phenylmethanesulfonyl fluoride, and 2 μg/mL of each aprotinin, pepstatin and leupeptin). The cells were homogenized in a Polytron (Brinkmann) for 20 s, centrifuged at 30,000×g, and the pellets washed twice with buffer HE (10 mM HEPES, 1 mM EDTA, pH 7.4 with protease inhibitors). The final pellet was resuspended in buffer HE, supplemented with 10% sucrose and frozen in aliquots at −80° C. For binding assays membranes were thawed and diluted 5-10 fold with HE to a final protein concentration of approximately 1 mg/mL. To determine protein concentrations, membranes, and bovine serum albumin standards were dissolved in 0.2% NaOH/0.01% SDS and protein determined using fluorescamine fluorescence. Stowell, C. P. et al., Anal. Biochem., 85, 572-580 (1978).

Saturation binding assays for rat $A_{2B}$ adenosine receptors were performed with [$^3$H]ZM214,385 (17 Ci/mmol, Tocris Cookson, Bristol UK) (Ji, X. et al., *Drug Design Discov.*, 16, 216-226 (1999)) or $^{125}$I-ABOPX (2200 Ci/mmol). To prepare $^{125}$I-ABOPX, 10 μL of 1 mM ABOPX in methanol/1 M NaOH (20:1) was added to 50 μL of 100 mM phosphate buffer, pH 7.3. One or 2 mCi of Na $^{125}$I was added, followed by 10 μL of 1 mg/mL chloramine-T in water. After incubation, 20 minutes at room temperature, 50 μL of 10 mg/mL Na-metabisulfite in water was added to quench the reaction. The reaction mixture was applied to a C18 HPLC column, eluting with a mixture of methanol and 5 mM phosphate, pH 6.0. After 5 min at 35% methanol, the methanol concentration was ramped to 100% over 15 min. Unreacted ABOPX eluted in 11-12 minutes; $^{125}$I-ABOPX eluted at 18-19 min in a yield of 50-60% with respect to the initial [125]I.

In equilibrium binding assays the ratio of [127]I/$^{125}$I-ABOPX was 10-20/1. Radioligand binding experiments were performed in triplicate with 20-25 μg membrane protein in a total volume of 0.1 mL HE buffer supplemented with 1 U/mL adenosine deaminase and 5 mM $MgCl_2$. The incubation time was 3 h at 21° C. Nonspecific binding was measured in the presence of 100 μM NECA. Competition experiments were carried out using 0.6 nM $^{125}$I-ABOPX. Membranes were filtered on Whatman GF/C filters using a Brandel cell harvester (Gaithersburg, Md.) and washed 3 times over 15-20 seconds with ice cold buffer (10 mM Tris, 1 mM $MgCl_2$, pH 7.4). $B_{max}$ and $K_D$ values were calculated by Marquardt's nonlinear least squares interpolation for single a site binding models. Marquardt, D. M., *J. Soc. Indust. Appl. Math.*, 11, 431-441.21 (1963). $K_i$ values for different compounds were derived from $IC_{50}$ values as described. Linden, J., *J. Cycl. Nucl. Res.*, 8, 163-172 (1982). Data from replicate experiments are tabulated as means ±SEM.

At other Adenosine Receptors: [³H]CPX. Bruns, R. F. et al., *Naunyn-Schmiedeberg's Arch. Pharmacol.*, 335, 59-63 (1987). [125]I-ZM241385 and $^{125}$I-ABA were utilized in radioligand binding assays to membranes derived from HEK-293 cells expressing recombinant rat $A_1$, $A_{2A}$ and $A_3$ ARs, respectively. Binding of [³H]R—$N^6$-phenylisopropyladenosine. Schwabe, U. et al., *Naunyn-Schmiedeberg's Arch. Pharmacol.*, 313, 179-187 (1980). ([³H]R-PIA, Amersham, Chicago, Ill.) to $A_1$ receptors from rat cerebral cortical membranes and of [³H]CGS 21680. Jarvis, M. F. et al., *J. Pharmacol. Exp. Therap.*, 251, 888-893 (1989). (Dupont NEN, Boston, Mass.) to $A_{2A}$ receptors from rat striatal membranes was performed as described. Adenosine deaminase (3 units/mL) was present during the preparation of the brain membranes, in a pre-incubation of 30 min at 30° C., and during the incubation with the radioligands. All non-radioactive compounds were initially dissolved in DMSO, and diluted with buffer to the final concentration, where the amount of DMSO never exceeded 2%. Incubations were terminated by rapid filtration over Whatman GF/B filters, using a Brandell cell harvester (Brandell, Gaithersburg, Md.). The tubes were rinsed three times with 3 mL buffer each.

At least six different concentrations of competitor, spanning 3 orders of magnitude adjusted appropriately for the $IC_{50}$ of each compound, were used. $IC_{50}$ values, calculated with the nonlinear regression method implemented in (Graph-Pad Prism, San Diego, Calif.), were converted to apparent $K_i$ values as described. Linden, J., *J. Cycl. Nucl. Res.*, 8:163-172 (1982). Hill coefficients of the tested compounds were in the range of 0.8 to 1.1.

Functional Assay

HEK-$A_{2B}$ cells from one confluent T75 flask were rinsed with $Ca^{2+}$ and $Mg^{2+}$-free Dulbecco's phosphate buffered saline (PBS) and incubated in $Ca^{2+}$ and $Mg^{2+}$-free HBSS with 0.05% trypsin and 0.53 mM EDTA until the cells detached. The cells were rinsed twice by centrifugation at 250×g in PBS and resuspended in 10 mL of HBSS composed of 137 mM NaCl, 5 mM KCl, 0.9 mM $MgSO_4$, 1.4 mM $CaCl_2$, 3 mM $NaHCO_3$, 0.6 mM $Na_2HPO_4$, 0.4 mM $KH_3PO_4$, 5.6 mM glucose, and 10 mM HEPES, pH 7.4 and the $Ca^{2+}$-sensitive fluorescent dye indo-1-AM (5 μM) 37° C. for 60 min. The cells were rinsed once and resuspended in 25 mL dye-free HBSS supplemented with 1 U/ml adenosine deaminase and held at room temperature. Adenosine receptor antagonists prepared as 100× stocks in DMSO or vehicle was added and the cells and transferred to a 37° C. bath for 2 minutes. Then the cells (1 million in 2 ml) were transferred to a stirred cuvette maintained at 37° C. within an Aminco SLM 8000 spectrofluorometer (SML instruments, Urbana Ill.). The ratios of indo-1 fluorescence obtained at 400 and 485 nm (excitation, 332 nm) was recorded using a slit width of 4 nm. NECA was added after a 100 s equilibration period.

Cyclic AMP Accumulation

Cyclic AMP generation was performed in DMEM/HEPES buffer (DMEM containing 50 mM HEPES, pH 7.4, 37° C.). Each well of cells was washed twice with DMEM/HEPES buffer, and then 100 μL adenosine deaminase (final concentration 10 IU/mL) and 100 μL of solutions of rolipram and cilostamide (each at a final concentration of 10 μM) were added, followed by 50 μL of the test compound (appropriate concentration) or buffer. After 15 minutes, incubation at 37° C. was terminated by removing the medium and adding 200 μL of 0.1 M HCl. Acid extracts were stored at –20° C. until assay. The amounts of cyclic AMP were determined following a protocol which utilized a cAMP binding protein (PKA) [van der Wenden et al., 1995], with the following minor modifications. The assay buffer consisted of 150 mM $K_2HPO_4$/10 mM EDTA/0.2% BSA FV at pH 7.5. Samples (20 mL) were incubated for 90 minutes at 0° C. Incubates were filtered over GF/C glass microfiber filters in a Brandel M-24 Cell Harvester. The filters were additionally rinsed with 4 times 2 mL 150 mM $K_2HPO_4$/10 mM EDTA (pH 7.5, 4° C.). Punched filters were counted in Packard Emulsifier Safe scintillation fluid after 2 hours of extraction.

Representative compounds of the present invention have been shown to be active in the above affinity testing.

Synthesis and Characterization

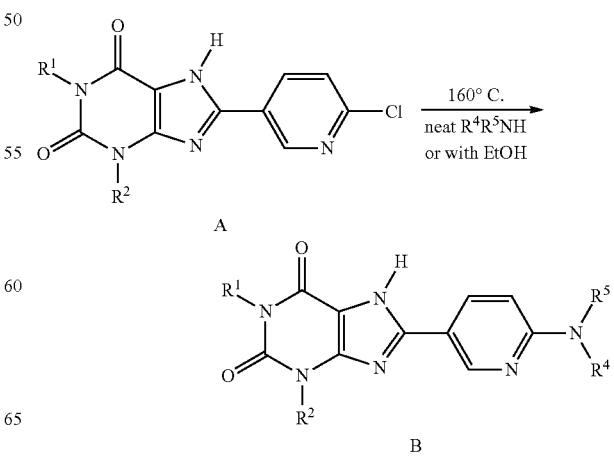

-continued

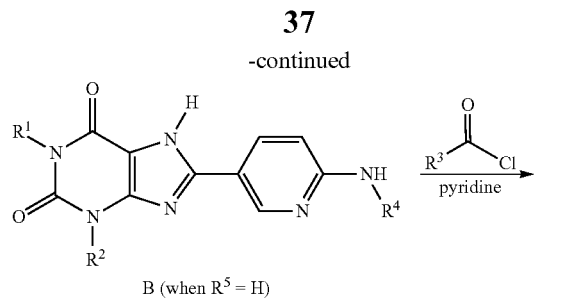

B (when R⁵ = H)

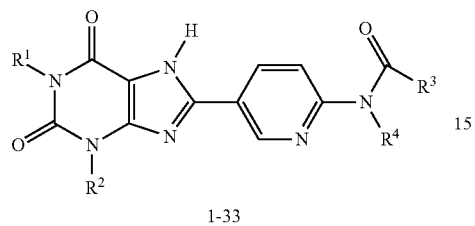

1-33

Proton nuclear magnetic resonance spectroscopy was performed on a Varian-300 MHz spectrometer and spectra were taken in DMSO-$d_6$. Unless noted, chemical shifts are expressed as ppm downfield from relative ppm from DMSO (2.5 ppm). Electro-spray-ionization (ESI) mass spectrometry was performed with a ThermoFinnigan LCQ mass spectrometer.

All xanthine derivatives were homogeneous as judged using TLC (Silica gel 60 $F_{254}$, 0.25 mm, aluminium backed, EM Science, Gibbstown, N.J.) and HPLC (Shimadzu) using Varian C18 5 micron analytical column (4.6 mm×150 mm) in linear gradient solvent system, at a flow rate of 1 mL/min. The solvent system used was MeOH (0.1% formic acid):$H_2O$ (0.1% formic acid). Peaks were detected by UV absorption at 300 nm and 254 nm. NMR and mass spectra were shown to be consistent with the assigned structure.

General Procedures for the Preparation of Chloro Substituted Pyridyl Compounds A 6-Chloronicotinoyl chloride, prepared from 6-hydroxynicotinic acid (1.444 g, 10.4 mmol), in $CH_2Cl_2$ (20 mL) was added dropwise to a solution of 5,6-diamino-1,3-disubstituteduracil (8 mmol) in dry pyridine (8.2 mL) maintained at 5° C. The reaction was warmed to room temperature and stirred for an additional 3 hours. Water (50 mL) was added to quench the reaction. The solvent was evaporated to afford a dark colored oil. The oil was refluxed for 2 h in 2N NaOH (20 mL). After cooling, the pH was carefully adjusted to 7 with concentrated HCl. A solid formed and was collected and washed with water (20 mL), ether (20 mL) and chloroform (20 mL) to provide an off-white solid. The product was used in the next step without further purification.

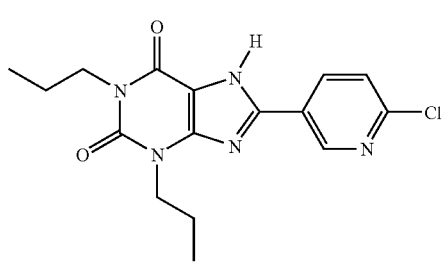

1A

2A

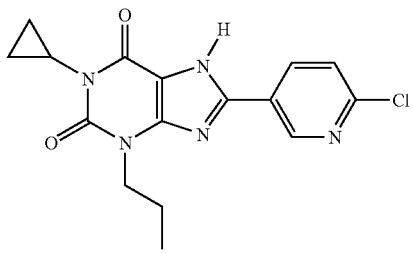

3A

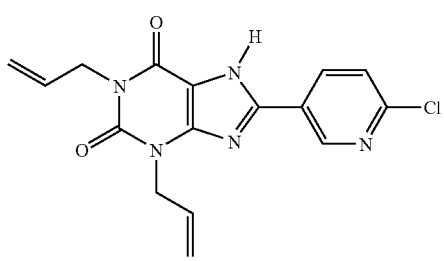

1A: 1,3-Dipropyl-8-(6-chloro-3-pyridyl)xanthine

¹H NMR (DMSO, $d_6$): δ 0.89 (m, 6H), 1.59 (m, 2H), 1.73 (m, 2H), 3.88 (t, 2H, J=7.2 Hz), 4.00 (t, 2H, J=7.2 Hz), 7.68 (d, 1H, J=8.4 Hz), 8.50 (dd, 1H, $J_1$=2.4 Hz, $J_2$=8.4 Hz), 9.07 (d, 1H, J=2.4 Hz).

MS: m/z 348 (M+H)⁺.

2A: 1-Cyclopropyl-3-propyl-8-(6-chloro-3-pyridyl)xanthine

¹H NMR (DMSO, $d_6$): δ 0.72 (m, 2H), 0.91 (t, 3H, J=7.8 Hz), 1.03 (m, 2H), 1.72 (m, 2H), 2.63 (m, 1H), 3.98 (t, 2H, J=7.8 Hz), 7.68 (d, 1H, J=8.4 Hz), 8.46 (dd, 1H, $J_1$=2.4 Hz, $J_2$=8.4 Hz), 9.07 (d, 1H, J=2.4 Hz).

MS: m/z 346 (M+H)⁺.

3A: 1,3-Diallyl-8-(6-chloro-3-pyridyl)xanthine

¹H NMR (DMSO, $d_6$): 4.56 (d, 2H, J=5.1 Hz), 4.70 (d, 2H, J=5.1 Hz), 5.15 (m, 4H), 5.98 (m, 2H), 7.74 (d, 1H, J=8.4 Hz), 8.50 (dd, 1H, $J_1$=2.4 Hz, $J_2$=8.4 Hz), 9.12 (d, 1H, J=2.4 Hz).

MS: m/z 344 (M+H)⁺.

General Procedures for the Preparation of Amino Substituted Pyridyl Compounds B

Compound A (40 mg) and the corresponding substituted amine (0.5 mL or 0.5 g) were put in a pressure tube. (Ethanol, 4 mL, was added as the solvent if the amine in a solid.) The pressure tube was flushed with argon, sealed and stirred at 160° C. for 48-60 h. After cooling, ether (10 mL) was added. The resulting solid was collected and purified by silica gel column or preparative TLC (Solvent A: $CH_2Cl_2$:MeOH=20:1 to 10:1 or Solvent B: $CH_2Cl_2$:MeOH:TEA=20:1:0.1 to 4:1:0.1).

1B
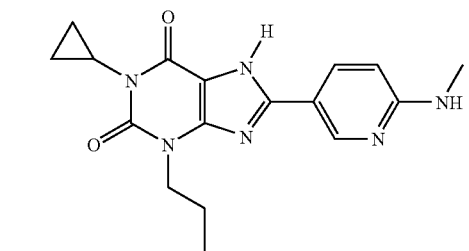
2B
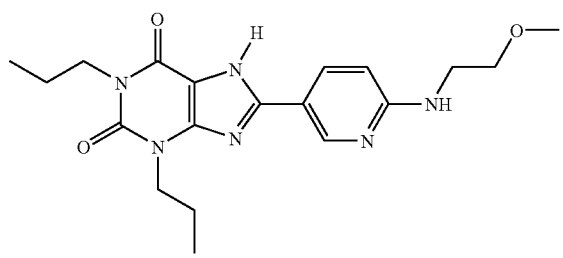
3B
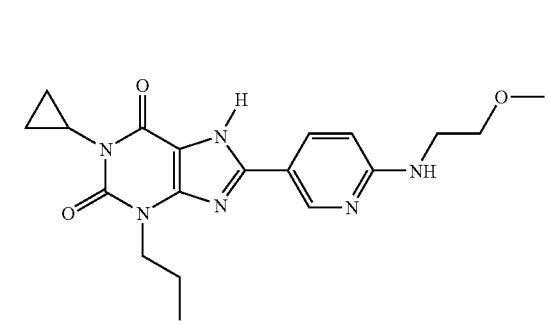
4B
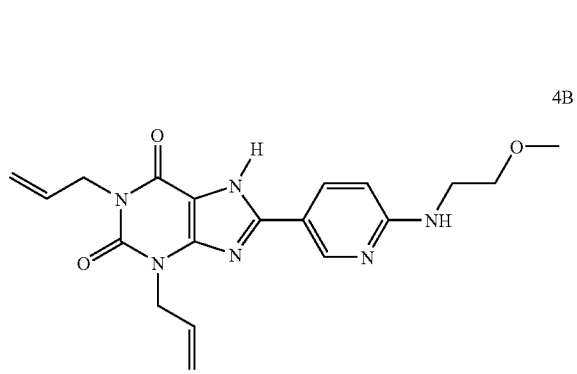
5B
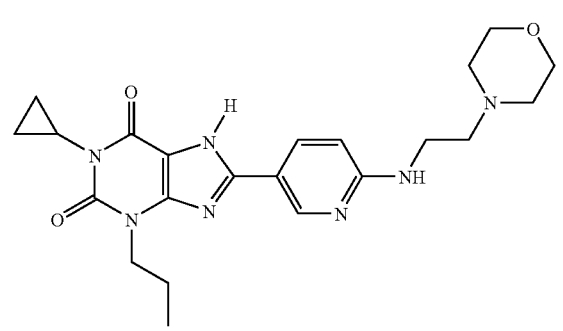
-continued
6B
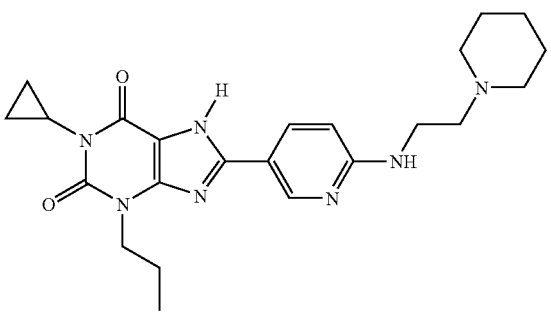
7B
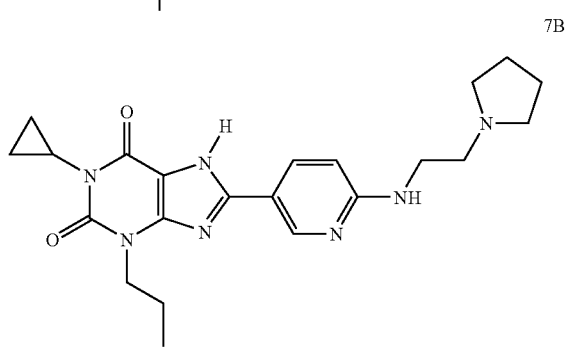
8B
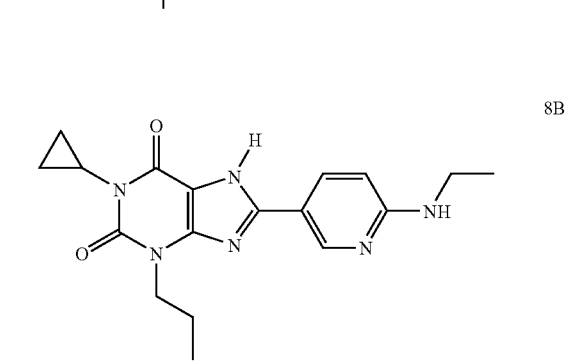
9B
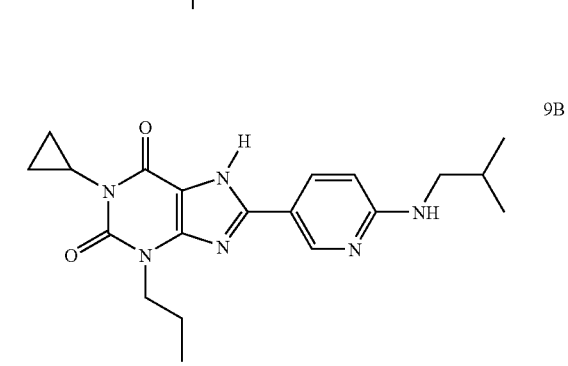
10B
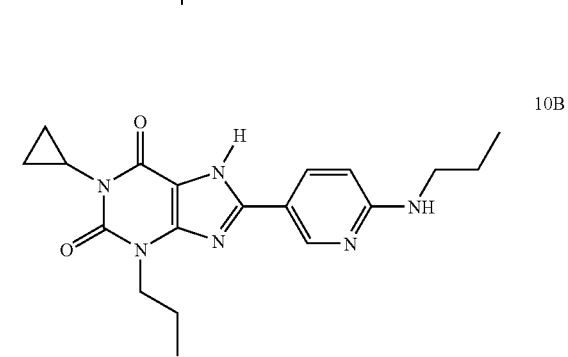

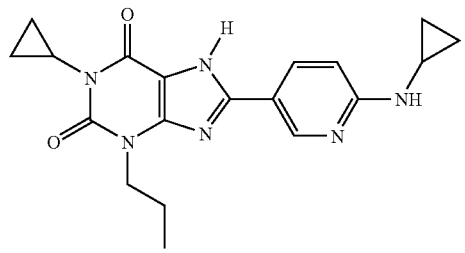

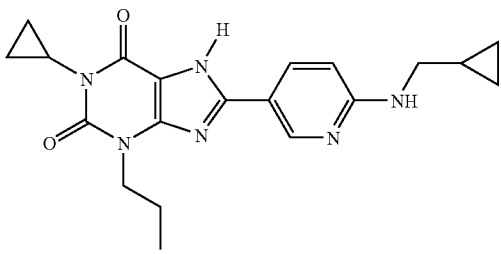

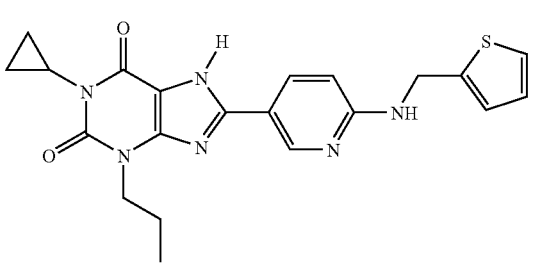

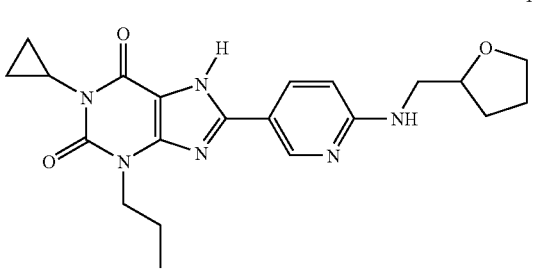

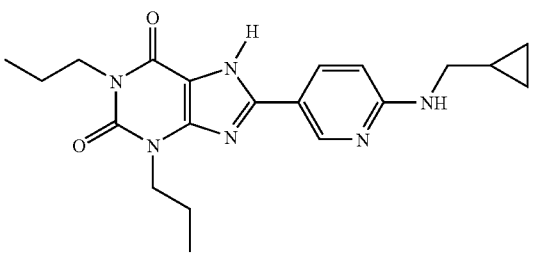

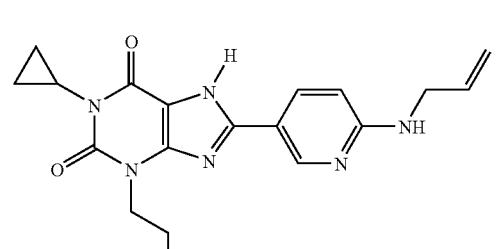

1B: 1-Cyclopropyl-3-propyl-8-[6-methylamino-3-pyridyl]xanthine $^1$H NMR (DMSO, d$_6$): 0.72 (m, 2H), 0.91 (t, 3H, J=7.5 Hz), 1.03 (m, 2H), 1.71 (m, 2H), 2.62 (m, 1H), 2.81 (d, 3H, J=4.5 Hz), 3.96 (t, 2H, J=7.5 Hz), 6.52 (d, 1H), 7.07 (d, 1H, J=4.5 Hz), 8.01 (dd, 1H, J$_1$=2.4 Hz, J$_2$=9.0 Hz), 8.73 (d, 1H, J=2.4 Hz).
MS: m/z 341 (M+H)$^+$.

2B: 1,3-Dipropyl-8-[6-(2-methoxyethyl)amino-3-pyridyl]xanthine $^1$H NMR (DMSO, d$_6$): δ 0.93 (m, 6H), 1.63 (m, 2H), 1.78 (m, 2H), 3.38 (s, 3H), 3.53 (s, 4H), 3.91 (t, 2H, J=7.5 Hz), 4.05 (t, 2H, J=7.5 Hz), 6.65 (d, 1H, J=8.7 Hz), 7.24 (s (br), 1H), 8.06 (dd, 1H, J$_1$=2.4 Hz, J$_2$=8.7 Hz), 8.71 (d, 1H, J=2.4 Hz).
MS: m/z 387 (M+H)$^+$.

3B: 1-Cyclopropyl-3-propyl-8-[6-(2-methoxyethyl)amino-3-pyridyl]xanthine $^1$H NMR (DMSO, d$_6$): 0.74 (m, 2H), 0.94 (t, 3H, J=7.5 Hz), 1.06 (m, 2H), 1.75 (m, 2H), 2.65 (m, 1H), 3.32 (s, 3H), 3.52 (s, 4H), 4.00 (t, 2H, J=7.5 Hz), 6.64 (d, 1H, J=8.7 Hz), 7.23 (s(br), 1H), 8.04 (dd, 1H, J$_1$=2.4 Hz, J$_2$=8.7 Hz), 8.76 (d, 1H, J=2.4 Hz).
MS: m/z 385 (M+H)$^+$.

4B: 1,3-Diallyl-8-[6-(2-methoxyethyl)amino-3-pyridyl]xanthine $^1$H NMR (DMSO, d$_6$): 3.32 (s, 3H), 3.52 (s, 4H), 4.55 (d, 2H, J=5.1 Hz), 4.68 (d, 2H, J=5.1 Hz), 5.15 (m, 4H), 5.95 (m, 2H), 6.64 (d, 1H, J=9.0 Hz), 7.25 (s(br), 1H), 1H, J$_1$=2.4 Hz, J$_2$=9.0 Hz), 8.77 (d, 1H, J=2.4 Hz).
MS: m/z 383 (M+H)$^+$.

5B: 1-Cyclopropyl-3-prolyl-8-[6-(2-morpholinoethyl)amino-3-pyridyl]xanthine $^1$H NMR (DMSO, d$_6$): 0.74 (m, 2H), 0.94 (t, 3H, J=7.5 Hz), 1.06 (m, 2H), 1.75 (m, 2H), 2.46 (t, 4H, J=4.5 Hz), 2.52 (m, 2H), 2.65 (m, 1H), 3.46 (m, 2H), 3.63 (t, 4H, J=4.5 Hz), 4.00 (t, 2H, J=7.2 Hz), 6.62 (d, 1H, J=8.7 Hz), 7.23 (t, 1H, J=5.4 Hz), 8.04 (dd, 1H, J$_1$=2.4 Hz, J$_2$=8.7 Hz), 8.75 (d, 1H, J=2.4 Hz).
MS: m/z 440 (M+H)$^+$.

6B: 1-Cyclopropyl-3-propyl-8-[6-(2-(piperidin-1-yl)ethylamino)-3-pyridyl]xanthine $^1$H NMR (DMSO, d$_6$): 0.74 (m, 2H), 0.94 (t, 3H, J=7.5 Hz), 1.07 (m, 2H), 1.44 (m, 2H), 1.57 (m, 4H), 1.75 (m, 2H), 2.51 (m, 6H), 2.65 (m, 1H), 3.48 (m, 2H), 4.00 (t, 2H, J=7.2 Hz), 6.63 (d, 1H, J=9.0 Hz), 7.05 (t, 1H), 8.05 (dd, 1H, J$_1$=2.4 Hz, J$_2$=9.0 Hz), 8.76 (d, 1H, J=2.4 Hz).
MS: m/z 438 (M+H)$^+$.

7B: 1-Cyclopropyl-3-propyl-8-[6-(2-(pyrrolidin-1-yl)ethylamino)-3-pyridyl]xanthine MS: m/z 424 (M+H)$^+$.

General Procedures for the Preparation of Amide Compounds (1-36):

The amino substituted pyridyl compound B (50 mg) was dissolved in pyridine (25 mg) at 80-100° C. After cooling to room temperature, the desired acid chloride (4-6 equivalents) was added at room temperature. The mixture was stirred at room temperature for 24-60 h. The reaction was quenched with ice and the solvent was removed and the residue was purified by silica gel column (CH$_2$Cl$_2$: MeOH=96: 4) to give compound 1-36 at 60-80% yield.

1: 1-Cyclopropyl-3-propyl-8-[6-(N-[6-(trifluoromethyl)nicotinoyl]-N-methylamino)-3-pyridyl]xanthine HPLC condition: MeOH 40%-95% gradient in 10 minutes, then MeOH 95%. Retention Time=9.77 min.
$^1$H NMR (DMSO, d$_6$): 0.72 (m, 2H), 0.89 (t, 3H, J=7.5 Hz), 1.01 (m, 2H), 1.71 (m, 2H), 2.62 (m, 1H), 3.53 (s, 3H), 3.96 (t, 2H, J=7.5 Hz), 7.53 (d, 1H, J=8.4 Hz,), 7.88 (d, 1H, J=8.4 Hz,), 8.00 (dd, 1H, J$_1$=1.8 Hz, J$_2$=7.8 Hz), 8.38 (dd, 1H, J$_1$=2.4 Hz, J$_2$=8.4 Hz), 8.70 (s, 1H), 8.94 (d, 1H, J=2.4 Hz).
MS: m/z 514 (M+H)$^+$.

2: 1-Cyclopropyl-3-propyl-8-[6-(N-[6-(trifluoromethyl)nicotinoyl]-N-ethylamino)-3-pyridyl]xanthine HPLC condition: MeOH 40%-95% gradient in 10 minutes then MeOH 95%. Time=10.13 min.
$^1$H NMR (DMSO, d$_6$): 0.70 (m, 2H), 0.88 (t, 3H, J=7.5 Hz), 1.02 (m, 2H), 1.19 (3H, J=7.2 Hz), 1.69 (m, 2H), 2.61 (m, 1H), 3.95 (t, 2H, J=7.2 Hz), 4.08 (q, 2H, J=7.5 Hz), 7.46 (d, 1H, J=8.7 Hz), 7.85 (d, 1H, J=8.1 Hz), 7.96 (dd, 1H, J$_1$=8.1 Hz, J$_2$=2.1 Hz), 8.36 (dd, 1H, J$_1$=8.7 Hz, J$_2$=2.1 Hz), 8.66 (s, 1H), 8.96 (d, 1H, J=2.1 Hz).
MS: m/z 528 (M+H)$^+$.

3: 1-Cyclopropyl-3-propyl-8-[6-(N-[6-(trifluoromethyl)nicotinoyl]-N-propylamino)-3-pyridyl]xanthine HPLC condition: MeOH 40%-95% gradient in 10 minutes then MeOH 95%. Retention Time=10.80 min.
$^1$H NMR (DMSO, d$_6$): $^1$H NMR (DMSO, d$_6$): 0.71 (m, 2H), 0.91 (m, 6H), 1.03 (m, 2H), 1.57-1.73 (m, 4H), 2.61 (m, 1H), 3.92-4.04 (m, 4H), 7.47 (d, 1H, J=8.7 Hz), 7.85 (d, 1H, J=8.4 Hz), 7.95 (d, 1H, J=8.4 Hz), 8.36 (dd, 1H, J$_1$=8.7 Hz, J$_2$=2.4 Hz), 8.66 (s, 1H), 8.95 (d, 1H, J=2.4 Hz).
MS: m/z 542 (M+H)$^+$.

4: 1-Cyclopropyl-3-propyl-8-[6-(N-[6-(trifluoromethyl)nicotinoyl]-N-(2-methoxyethyl)amino)-3-pyridyl]xanthine HPLC condition: MeOH 40%-95% gradient in 10 minutes then MeOH 95%. Retention Time=10.08 min.
$^1$H NMR (DMSO, d$_6$): $^1$H NMR (DMSO, d$_6$): 0.71 (m, 2H), 0.88 (t, 3H, J=7.5 Hz) 1.05 (m, 2H), 1.70 (m, 2H), 2.62 (m, 1H), 3.19 (s, 3H), 3.62 (t, 2H, J=5.4 Hz), 3.96 (t, 2H, J=7.5 Hz), 4.21 (t, 2H, J=5.4 Hz), 7.47 (d, 1H, J=8.7 Hz), 7.87 (d, 1H, J=8.1 Hz), 7.96 (d, 1H, J=8.1 Hz), 8.34 (dd, 1H, J=8.7 Hz, J$_2$=2.4 Hz), 8.66 (s, 1H), 8.95 (d, 1H, J=2.4 Hz).
MS: m/z 558 (M+H)$^+$.

5: 1-Cyclopropyl-3-propyl-8-[6-(N-(6-fluoronicotinoyl)-N-(2-methoxyethyl)amino)-3-pyridyl]xanthine HPLC condition: MeOH 40%-95% gradient in 10 minutes then MeOH 95%. Retention Time=9.32 min.
$^1$H NMR (DMSO, d$_6$): 0.74 (m, 2H), 0.92 (t, 3H, J=7.5 Hz), 1.06 (m, 2H), 1.73 (m, 2H), 2.65 (m, 1H), 3.19 (s, 3H), 3.64 (t, 2H, J=5.7 Hz), 3.99 (t, 2H, J=7.5 Hz), 4.22 (t, 2H, J=5.7 Hz), 7.18 (dd, 1H, J$_1$=8.4 Hz, J$_2$=2.4 Hz), 7.41 (d, 1H, J=8.4 Hz), 7.91 (td, 1H, J$_1$=8.4 Hz), 8.18 (d, 1H, J=2.4 Hz), 8.36 (dd, 1H, J$_1$=8.4 Hz, J$_2$=2.1 Hz), 8.76 (d, 1H, J=2.1 Hz).
MS: m/z 508 (M+H)$^+$.

6: 1-Cyclopropyl-3-propyl-8-[6-(N-nicotinoyl-N-(2-methoxyethyl)amino)-3-pyridyl]xanthine HPLC condition: MeOH 40%-95% gradient in 10 minutes then MeOH 95%. Retention Time=8.53 min.
MS: m/z 490 (M+H)$^+$.

7: 1-Cyclopropyl-3-propyl-8-[6-(N-nicotinoyl-N-(cyclopropylmethyl)amino)-3-pyridyl]xanthine HPLC condition: MeOH 40%-95% gradient in 10 minutes then MeOH 95%.
Retention Time=9.77 min.
MS: m/z 486 (M+H)$^+$.

8: 1-Cyclopropyl-3-propyl-8-[6-(N-nicotinoyl-N-(cyclopropyl)amino)-3-pyridyl]xanthine HPLC condition: MeOH 40%-95% gradient in 10 minutes then MeOH 95%. Retention Time=8.67 min.
MS: m/z 472 (M+H)$^+$.

9: 1-Cyclopropyl-3-propyl-8-[6-(N-[6-(trifluoromethyl)nicotinoyl]-N-(cyclopropylmethyl)amino)-3-pyridyl]xanthine HPLC condition: MeOH 40%-95% gradient in 10 minutes then MeOH 95%. Retention Time=10.71 min.
$^1$H NMR (DMSO, d$_6$): 0.19 (m, 2H), 0.41 (m, 2H), 0.72 (m, 2H), 0.91 (t, 3H, J=7.2 Hz), 1.00-1.16 (m, 3H), 1.70 (m, 2H), 2.62 (m, 1H), 3.96 (m, 4H), 7.47 (d, 1H, J=8.4 Hz), 7.86 (d, 1H, J=8.1 Hz,), 7.97 (dd, 1H, J$_1$=2.1 Hz, J$_2$=8.1 Hz), 8.36 (dd, 1H, J$_1$=2.1 Hz, J$_2$=8.4 Hz), 8.68 (s, 1H), 8.98 (d, 1H, J=2.1 Hz).
MS: m/z 554 (M+H)$^+$.

10: 1-Cyclopropyl-3-propyl-8-[6-(N-[6-(trifluoromethyl)nicotinoyl]-N-tetrahydrofuranylmethyl)amino)-3-pyridyl]xanthine HPLC condition: MeOH 40%-95% gradient in 10 minutes then MeOH 95%. Retention Time=10.31 min.
$^1$H NMR (DMSO, d$_6$): 0.71 (m, 2H), 0.88 (t, 3H, J=7.5 Hz), 1.02 (m, 2H), 1.54-1.96 (m, 6H), 2.61 (m, 1H), 3.57 (dt, 2H, J$_1$=6.9 Hz, J$_2$=3.0 Hz), 3.96 (t, 2H, J=7.2 Hz), 4.04-4.18 (m, 3H), 7.48 (d, 1H, J=8.4 Hz), 7.85 (d, 1H, J=8.4 Hz), 7.95 (dd, 1H, J$_1$=8.4 Hz, J$_2$=2.4 Hz), 8.34 (dd, 1H, J$_1$=8.4 Hz, J$_2$=2.4 Hz), 8.66 (s, 1H), 8.93 (d, 1H, J=2.4 Hz).
MS: m/z 584 (M+H)$^+$.

11: 1-Cyclopropyl-3-propyl-8-[6-(N-nicotinoyl-N-ethylamino)-3-pyridyl]xanthine

HPLC condition: MeOH 40%-95% gradient in 10 minutes then MeOH 95%. Retention Time=8.93 min.
$^1$H NMR (DMSO, d$_6$): 0.72 (m, 2H), 0.91 (t, 3H, J=7.2 Hz), 1.04 (m, 2H), 1.19 (t, 3H, J=7.2 Hz), 1.70 (m, 2H), 2.61 (m, 1H), 3.95 (t, 2H, J=7.2 Hz), 4.06 (q, 2H, J=7.2 Hz), 7.33 (m, 2H), 7.80 (dt, 1H, J$_1$=1.5 Hz, J$_2$=8.1 Hz,), 8.31 (dd, 1H, J$_1$=2.4 Hz, J$_2$=8.4 Hz), 8.44 (d, 1H, J=2.1), 8.53 (dd, 1H, J$_1$=2.1 Hz, J$_2$=4.8 Hz), 8.99 (d, 1H, J=2.1 Hz).
MS: m/z 460 (M+H)$^+$.

12: 1-Cyclopropyl-3-propyl-8-[6-(N-nicotinoyl-N-propylamino)-3-pyridyl]xanthine $^1$H NMR (DMSO, d$_6$): 0.72 (m, 2H), 0.88 (t, 6H, J=7.5 Hz), 1.02 (m, 2H), 1.57-1.74 (m, 4H), 2.62 (m, 1H), 3.97 (m, 4H), 7.31 (dd, 1H, J1=7.8 Hz, J$_2$=0.9 Hz), 7.34 (d, 1H, J=8.7 Hz), 7.68 (dt, 1H, J$_1$=7.8 Hz, J$_2$=1.8 Hz,), 8.30 (dd, 1H, J$_1$=8.4 Hz, J$_2$=2.4 Hz), 8.42 (d, 1H, J=2.4 Hz), 8.51 (dd, 1H, J$_1$=4.8 Hz, J$_2$=1.5 Hz), 8.99 (d, 1H, J=2.4 Hz).
HPLC condition: MeOH 40%-95% gradient in 10 minutes then MeOH 95%: Retention Time=9.7 min.
MS: m/z 474 (M+H)$^+$.

13: 1-Cyclopropyl-3-propyl-8-[6-(N-[6-fluoronicotinoyl]-N-[cyclopropylmethyl]amino)-3-pyridyl]xanthine HPLC condition: MeOH 40%-95% gradient in 10 minutes then MeOH 95%. Retention Time=10.09 min.
$^1$H NMR (DMSO, d$_6$): 0.15 (m, 2H), 0.39 (m, 2H), 0.72 (m, 2H), 0.89 (t, 3H, J=7.5 Hz), 1.00-1.20 (m, 3H), 1.71 (m, 2H), 2.63 (m, 1H), 3.95 (m, 4H), 7.13 (dd, 1H, J$_1$=8.4 Hz, J$_2$=2.1 Hz), 7.37 (d, 1H, J=8.4 Hz), 7.88 (m, 1H), 8.16 (s, 1H), 8.33 (dd, 1H, J$_1$=8.4 Hz, J$_2$=2.1 Hz), 9.00 (d, 1H, J=2.1 Hz).
MS: m/z 504 (M+H)$^+$.

14: 1-Cyclopropyl-3-propyl-8-[6-(N-[6-fluoronicotinoyl]-N-methylamino)-3-pyridyl]xanthine HPLC condition: MeOH 40%-95% gradient in 10 minutes then MeOH 95%. Retention Time=9.00 min.
$^1$H NMR (DMSO, d$_6$): 0.72 (m, 2H), 0.90 (t, 3H, J=7.5 Hz), 1.03 (m, 2H), 1.72 (m, 2H), 2.63 (m, 1H), 3.51 (s, 3H), 3.97 (t, 2H, J=7.5 Hz), 7.17 (dd, 1H, J$_1$=8.1 Hz, J$_2$=2.1 Hz), 7.45 (d, 1H, J=8.4 Hz,), 7.93 (m, 1H), 8.20 (s, 1H), 8.36 (dd, 1H, J$_1$=7.5 Hz, J$_2$=2.1 Hz), 8.99 (s, MS: m/z 464 (M+H)$^+$.

15: 1-Cyclopropyl-3-propyl-8-[6-(N-nicotinoyl-N-allylamino)-3-pyridyl]xanthine HPLC condition: MeOH 40%-95% gradient in 10 minutes then MeOH 95%. Retention Time=9.28 min.
$^1$H NMR (DMSO, d$_6$): $^1$H NMR (DMSO, d$_6$): □ 0.71 (m, 2H), 0.88 (t, 3H, J=7.5 Hz), 1.03 (m, 2H), 1.68 (m, 2H), 2.61 (m, 1H), 3.95 (t, 2H, J=7.2 Hz), 4.67 (d, 2H, J=4.5 Hz), 5.16 (m, 2H), 5.92 (m, 1H), 7.37 (m, 2H), 7.73 (d, 1H, J=7.8 Hz), 8.32 (d, 1H, J=8.7 Hz), 8.48 (s, 1H), 8.54 (, d, 1H, J=3.9 Hz), 9.0 (s, 1H).
MS: m/z 472 (M+H)$^+$.

16: 1-Cyclopropyl-3-propyl-8-[6-(N-[6-(trifluoromethyl)nicotinoyl]-N-allylamino)-3-pyridyl]xanthine HPLC condition: MeOH 40%-95% gradient in 10 minutes then MeOH 95%. Retention Time=10.37 min.
$^1$H NMR (DMSO, d$_6$): $^1$H NMR (DMSO, d$_6$): 0.73 (m, 2H), 0.91 (t, 3H, J=7.5 Hz), 1.03 (m, 2H), 1.72 (m, 2H), 2.66 (m, 1H), 3.99 (t, 2H, J=7.2 Hz), 4.73 (d, 2H, J=4.8 Hz), 5.15-5.30 (m, 2H), 5.91-6.00 (m, 1H), 7.53 (d, 2H, J=8.4 Hz), 7.91 (d, 1H, J=8.1 Hz), 8.03 (d, 1H, J=8.1 Hz), 8.40 (dd, 1H, J$_1$=8.4 Hz, J$_2$=2.1 Hz), 8.73 (s, 1H), 8.95 (d, 1H, J=2.1 MS: m/z 540 (M+H)$^+$.

17: 1-Cyclopropyl-3-propyl-8-[6-(N-nicotinoyl-N-(2-[piperidin-1-yl]ethyl)-amino)-3-pyridyl]xanthine HPLC condition: MeOH 40%-95% gradient in 10 minutes then MeOH 95%. Retention Time=4.90 min.
MS: m/z 543 (M+H)$^+$.

18: 1-Cyclopropyl-3-propyl-8-[6-(N-[6-(trifluoromethyl)nicotinoyl]-N-(2-[piperin-1-yl]ethyl)amino)-3-pyridyl]xanthine HPLC condition: MeOH 40%-95% gradient in 10 minutes then MeOH 95%. Retention Time=6.63 min.
MS: m/z 611 (M+H)$^+$.

19: 1-Cyclopropyl-3-propyl-8-[6-(N-nicotinoyl-N-(2-morpholinoethyl)amino)-3-pyridyl]xanthine HPLC condition: MeOH 20%-70% gradient in 10 minutes then MeOH 70%. Retention Time=9.44 min.
MS: m/z 545 (M+H)$^+$.

20: 1-Cyclopropyl-3-propyl-8-[6-(N-[6-(trifluoromethyl)nicotinoyl]-N-(2-morpholinoethyl)amino)-3-pyridyl]xanthine HPLC condition: MeOH 40%-95% gradient in 10 minutes then MeOH 95%. Retention Time=6.36 min.
$^1$H NMR (DMSO, d$_6$): 0.73 (m, 2H), 0.91 (t, 3H, J=7.5 Hz), 1.05 (m, 2H), 1.73 (m, 2H), 2.36 (m, 4H), 2.63 (m, 3H), 3.39 (m, 4H), 3.99 (t, 2H, J=7.5 Hz), 4.20 (t, 2H, J=6.0 Hz), 7.43 (d, 1H, J=8.4 Hz), 7.90 (d, H, J=8.1 Hz), 8.00 (d, 1H, J=8.1 Hz), 8.34 (dd, 1H, J$_1$=8.4 Hz, J$_2$=2.4 Hz), 8.70 (s, 1H), 8.99 (d, 1H, J=2.4 Hz).
MS: m/z 613 (M+H)$^+$.

21: 1-Cyclopropyl-3-propyl-8-[6-(N-[6-fluoronicotinoyl]-N-(2-[piperidin-1-yl]ethyl)amino)-3-pyridyl]xanthine HPLC condition: MeOH 20%-52% gradient in 10 minutes then MeOH 52%.
Retention Time=13.9 min.
$^1$H NMR (DMSO, d$_6$): 0.74 (m, 2H), 0.92 (t, 3H, J=7.5 Hz), 1.06 (m, 2H), 1.45-1.84 (m, 8H), 2.65 (m, 1H), 2.99 (m, 2H), 3.35 (m, 2H), 3.59 (m, 2H), 3.99 (t, 2H, J=7.5 Hz), 4.45 (m, 2H), 7.20 (dd, 1H, J$_1$=8.4 Hz, J$_2$=2.4 Hz), 7.43 (d, 1H, J=8.4 Hz), 7.97 (dt, 1H, J$_1$=8.1 Hz, J$_2$=2.4 Hz), 8.23 (d, H, J=2.4 Hz), 8.35 (dd, 1H, J$_1$=8.4 Hz, J$_2$=2.4 Hz), 9.12 (d, 1H, J=2.4 Hz), 10.13 (s, 1H).
MS: m/z 561 (M+H)$^+$.

22: 1-Cyclopropyl-3-propyl-8-[6-(N-[6-fluoronicotinoyl]-N-(2-morpholinoethyl)amino)-3-pyridyl]xanthine HPLC condition: MeOH 20%-70% gradient in 10 minutes then MeOH 70%. Retention Time=10.13 min.
$^1$H NMR (DMSO, d$_6$): 0.73 (m, 2H), 0.89 (t, 3H, J=7.5 Hz), 1.03 (m, 2H), 1.73 (m, 2H), 2.34 (m, 4H), 2.62 (m, 3H), 3.39 (m, 4H), 3.96 (t, 2H, J=7.5 Hz), 4.16 (m, 2H), 7.14 (dd, 1H, J$_1$=8.7 Hz, J$_2$=2.4 Hz), 7.31 (d, 1H, J=8.7 Hz), 7.89 (td, J$_1$=8.4 Hz, J$_2$=2.4 Hz), 8.16 (d, 1H, J=2.4 Hz), 8.29 (dd, 1H, J$_1$=8.7 Hz, J$_2$=2.4 Hz), 9.00 (s, 1H).
MS: m/z 563 (M+H)$^+$.

23: 1-Cyclopropyl-3-propyl-8-[6-(N-nicotinoyl-N-(2-[pyrrolidin-1-yl]ethyl)amino)-3-pyridyl]xanthine HPLC condition: MeOH 40%-95% gradient in 10 minutes then MeOH 95%. Retention Time=4.62 min.
MS: m/z 529 (M+H)$^+$.

24: 1-Cyclopropyl-3-propyl-8-[6-(N-[6-(trifluoromethyl)nicotinoyl]-N-(2-[pyrrolidin-1-yl]ethyl)amino)-3-pyridyl]xanthine HPLC condition: MeOH 40%-95% gradient in 10 minutes then MeOH 95%. Retention Time=6.43 min.
MS: m/z 597 (M+H)$^+$.

25: 1-Cyclopropyl-3-propyl-8-[6-[(N-nicotinoyl-N-[(thiophen-2-yl)methyl]amino)]-3-pyridyl]xanthine HPLC condition: MeOH 40%-95% gradient in 10 minutes then MeOH 95%. Retention Time=10.10 min.
MS: m/z 528 (M+H)$^+$.

26: 1-Cyclopropyl-3-propyl-8-[6-(N-[6-(trifluoromethyl)nicotinoyl]-N-iso-butylamino)-3-pyridyl]xanthine HPLC condition: MeOH 40%-95% gradient in 10 minutes then MeOH 95%. Retention Time=11.06 min.
$^1$H NMR (DMSO, d$_6$): 0.71 (m, 2H), 0.88 (m, 9H), 1.02 (m, 2H), 1.68 (m, 2H), 1.91 (m, 1H), 2.61 (m, 1H), 3.95 (m, 4H), 7.48 (d, 1H, J=8.4 Hz), 7.83 (d, 1H, J=8.4 Hz), 7.92 (d, 1H, J=8.1 Hz), 8.35 (dd, 1H, J$_1$=8.4 Hz, J$_2$=2.1 Hz), 8.64 (s, 1H), 8.94 (d, 1H, J=2.1 Hz).
MS: m/z 556 (M+H)$^+$.

27: 1,3-Dipropyl-8-[6-(N-nicotinoyl-N-(cyclopropylmethyl)amino)-3-pyridyl]xanthine HPLC condition: MeOH 40%-95% gradient in 10 minutes then MeOH 95%. Retention Time=10.63 min.
$^1$H NMR (DMSO, d$_6$): 0.18 (m, 2H), 0.42 (m, 2H), 0.89 (m, 6H), 1.15 (m, 1H), 1.60 (m, 2H), 1.74 (m, 2H), 3.87 (t, 2H, J=7.2 Hz), 4.01 (m, 4H), 7.34 (m, 2H), 7.71 (d, 1H, J=7.8 Hz), 8.31-8.54 (m, 3H), 8.69 (s, 1H).
MS: m/z 488 (M+H)$^+$.

28: 1,3-Dipropyl-8-[6-(N-[6-(trifluoromethyl)nicotinoyl]-N-cyclopropylmethyl)amino)-3-pyridyl]xanthine HPLC condition: MeOH 40%-95% gradient in 10 minutes then MeOH 95%. Retention Time=11.46 min.
$^1$H NMR (DMSO, d$_6$): 0.18 (m, 2H), 0.42 (m, 2H), 0.89 (m, 6H), 1.16 (m, 1H), 1.60 (m, 2H), 1.74 (m, 2H), 3.87 (t, 2H, J=7.2 Hz), 4.01 (m, 4H), 7.49 (d, 1H, J=8.4 Hz), 7.87 (d, 1H, J=8.4 Hz), 7.97 (d, 1H, J=8.4 Hz), 8.38 (dd, 1H, J$_1$=8.4 Hz, J$_2$=2.4 Hz), 8.69 (s, 1H), 9.00 (d, 1H, J=2.4 Hz).
MS: m/z 556 (M+H)$^+$.

29: 1,3-Dipropyl-8-[6-(N-[6-(trifluoromethyl)nicotinoyl]-N-(2-methoxyethyl)amino)-3-pyridyl]xanthine HPLC condition: MeOH 40%-95% gradient in 10 minutes then MeOH 95%. Retention Time=10.91 min.
$^1$H NMR (DMSO, d$_6$): 0.87 (m, 6H), 1.60 (m, 2H), 1.73 (m, 2H), 3.19 (s, 3H), 3.62 (t, 3H, J=5.1 Hz), 3.86 (t, 2H, J=7.2 Hz), 4.00 (t, 2H, J=7.2 Hz), 4.31 (t, 2H, J=5.1 Hz), 7.48 (d, 1H, J=8.4 Hz), 7.87 (d, 1H, J=8.4 Hz,), 7.96 (d, 1H, J=8.4 Hz), 8.36 (dd, 1H, J$_1$=8.4 Hz, J$_2$=2.4 Hz), 8.66 (s, 1H), 8.95 (d, 1H, J=2.4 Hz).
MS: m/z 560 (M+H)$^+$.

30: 1,3-Dipropyl-8-[6-(N-(6-fluoronicotinoyl)-N-(2-methoxyethyl)amino)-3-pyridyl]xanthine $^1$H NMR (DMSO, d$_6$): 0.88 (m, 6H), 1.57 (m, 2H), 1.72 (m, 2H), 3.18 (s, 3H), 3.60 (t, 2H, J=5.7 Hz), 3.86 (t, 2H, J=7.5 Hz), 4.00 (t, 2H, J=7.5 Hz), 4.19 (t, 2H, J=5.7 Hz), 7.14 (dd, 1H, J$_1$=8.7 Hz, J$_2$=2.7 Hz), 7.39 (d, 1H, J=8.7 Hz,), 7.88 (dt, 1H, J$_1$=8.4 Hz, J$_2$=2.7 Hz), 8.15 (d, 1H, J=2.7 Hz), 8.34 (dd, 1H, J$_1$=8.4 Hz, J$_2$=2.4 Hz), 8.99 (d, 1H, J=2.4 Hz).
HPLC condition: MeOH 40%-95% gradient in 10 minutes then MeOH 95%: Retention Time=10.18 min.
MS: m/z 510 (M+H)$^+$.

31: 1,3-Diallyl-8-[6-(N-[6-(trifluoromethyl)nicotinoyl]-N-(2-methoxyethyl)amino)-3-pyridyl]xanthine $^1$H NMR (DMSO, d$_6$): 3.18 (s, 3H), 3.60 (t, 2H, J=5.4 Hz), 4.21 (t, 2H, J=5.4 Hz), 4.50 (d, 2H, J=4.5 Hz), 4.64 (d, 2H, J=4.5 Hz), 5.02-5.15 (m, 4H), 5.83-6.00 (m, 2H), 7.48 (d, 1H, J=8.7 Hz), 7.86 (d, 1H, J=8.4 Hz,), 7.95 (d, 1H, J=8.4 Hz), 8.35 (dd, 1H, J$_1$=8.4 Hz, J$_2$=2.4 Hz), 8.67 (d, 1H, J=1.5 Hz), 8.95 (d, 1H, J=2.4 Hz).
HPLC condition: MeOH 40%-95% gradient in 10 minutes then MeOH 95%: Retention Time=9.81 min.
MS: m/z 556 (M+H)$^+$.

32: 1,3-Diallyl-8-[6-(N-[6-fluoronicotinoyl]-N-(2-methoxyethyl)amino)-3-pyridyl]xanthine HPLC condition: MeOH 40%-95% gradient in 10 minutes then MeOH 95%. Retention Time=9.00 min.
MS: m/z 506 (M+H)$^+$.

33: 13-Diallyl-8-[6-(N-nicotinoyl-N-(2-methoxyethyl)amino)-3-pyridyl]xanthine HPLC condition: MeOH 40%-95% gradient in 10 minutes then MeOH 95%. Retention Time=8.28 min.
MS: m/z 488 (M+H)$^+$.

34: 1,3-Dipropyl-8-[6-(N-piperazinyl)-3-pyridyl]xanthine

Compound 34 can be formed from compound IA by condensation with piperazine.
HPLC condition: MeOH 20%-75% gradient in 10 minutes then MeOH 75%. Retention Time=9.24 min.
$^1$H NMR (DMSO, d$_6$): 0.87 (q, 6H, J=7.5 Hz), 1.56 (m, 2H), 1.72 (m, 2H), 2.78 (t, 4H, J=4.5 Hz), 3.52 (t, 4H, J=4.5 Hz), 3.85 (t, 2H, J=7.5 Hz), 3.99 (t, 2H, J=7.5 Hz), 6.88 (d, 1H, J=9.0 Hz), 8.13 (dd, 1H, J$_1$=9.0 Hz, J$_2$=2.4 Hz), 8.80 (d, 1H, J=2.4 Hz).
MS: m/z 398 (M+H)$^+$.

35: 1,3-Dipropyl-8-[6-(N-(6-fluoronicotinoyl)-N-(methyl)amino)-3-pyridyl]xanthine HPLC condition: MeOH 40%-95% gradient in 10 minutes then MeOH 95%. Retention Time=10.01 min.
$^1$H NMR (DMSO, d$_6$): $^1$H NMR (DMSO, d$_6$): 0.88 (m, 6H), 1.57 (m, 2H), 1.72 (m, 2H), 3.50 (s, 3H), 3.86 (t, 2H, J=7.5 Hz), 4.00 (t, 2H, J=7.5 Hz), 7.16 (dd, 1H, J$_1$=8.4 Hz, J$_2$=2.4 Hz), 7.45 (d, 1H, J=8.7 Hz), 7.92 (dt, 1H, J$_1$=8.4 Hz, J$_2$=2.4 Hz), 8.19 (d, 1H, 8.36 (dd, 1H, J$_1$=8.7 Hz, J$_2$=2.4 Hz), 8.99 (d, 1H, J=2.4 Hz).
MS: m/z 466 (M+H)$^+$.

36: 1,3-Dipropyl-8-[6-(N-[6-(trifluoromethyl)nicotinoyl]-N-(ethyl)amino]-3-pyridyl]xanthine HPLC condition: MeOH 40%-95% gradient in 10 minutes then MeOH 95%. Retention Time=10.87 min.

$^1$H NMR (DMSO, d$_6$): 0.92 (m, 6H), 1.24 (t, 3H, J=6.9 Hz), 1.55-1.78 (m, 4H), 3.90 (t, 2H, J=7.2 Hz), 4.03 (t, 2H, J=7.2 Hz), 4.12 (q, 2H, J=6.9 Hz), 7.51 (d, 1H, J=8.4 Hz), 7.90 (d, 1H, J=8.4 Hz), 8.00 (dd, 1H, J$_1$=8.4 Hz, J$_2$=1.8 Hz), 8.41 (dd, 1H, J$_1$=8.4 Hz, J$_2$=2.1 Hz), 8.71 (s, 1H), 9.01 (d, 1H, J=1.8 Hz).

$^{13}$C NMR (DMSO, d$_6$): 10.95, 11.11, 13.10, 20.79, 20.78, 42.181, 43.12, 44.46, 108.22, 120.26, 120.45, 120.97, 122.87, 135.71, 136.06, 137.75, 146.44, 146.55, 147.00, 148.25, 149.03, 150.61, 154.08, 155.11, 166.48.

MS: m/z 530 (M+H)$^+$.

What is claimed is:

1. A method for treating ulcerative colitis, comprising:
administering to a patient in need thereof a therapeutically effective amount of an A$_{2B}$ adenosine receptor antagonist, wherein the A2B adenosine antagonist is a compound of formula Id or a stereoisomer or pharmaceutically acceptable salt thereof,

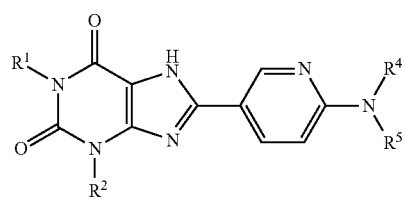

Id wherein R$^1$ and R$^2$ are independently selected from H, (C$_1$-C$_8$)alkyl, (C$_3$-C$_8$)alkenyl, (C$_3$-C$_8$)alkynyl, (C$_1$-C$_8$)alkoxy, (C$_3$-C$_8$)cycloalkyl, (C$_3$-C$_8$)cycloalkyl(C$_1$-C$_8$)alkyl-, (C$_4$-C$_{10}$)heterocycle, (C$_4$-C$_{10}$)heterocycle(C$_1$-C$_8$)alkyl-, (C$_6$-C$_{10}$)aryl, (C$_6$-C$_{10}$)aryl(C$_1$-C$_8$)alkyl-, (C$_5$-C$_{10}$)heteroaryl, and (C$_5$-C$_{10}$)heteroaryl(C$_1$-C$_8$)alkyl-;

R$^4$ and R$^5$ are independently selected from H, (C$_1$-C$_8$)alkyl, (C$_3$-C$_8$)alkenyl, (C$_3$-C$_8$)alkynyl, (C$_1$-C$_8$)alkoxy, (C$_3$-C$_8$)cycloalkyl, (C$_3$-C$_8$)cycloalkyl(C$_1$-C$_8$)alkyl-, (C$_6$-C$_{18}$)polycycloalkyl, (C$_6$-C$_{18}$)polycycloalkyl(C$_1$-C$_8$)alkyl-, (C$_3$-C$_{10}$)heterocycle, (C$_3$-C$_{10}$)heterocycle(C$_1$-C$_8$)alkyl-, —NR$^7$R$^8$ (C$_6$-C$_{10}$)aryl, (C$_6$-C$_{10}$)aryl(C$_1$-C$_8$)alkyl-, (C$_5$-C$_{10}$)heteroaryl, (C$_5$-C$_{10}$)heteroaryl(C$_1$-C$_8$)alkyl-,—(C$_2$-C$_4$—Y)$_q$—(CH$_2$)$_{2-4}$—X$^1$, —C(O)R$^6$, —CO$_2$R$^6$, —C(O)NR$^7$R$^8$ and —S(O)$_2$—NR$^7$R$^8$;

X$^1$ is selected from —OR$^6$, —C(O)R$^6$, —CO$_2$R$^6$ and —NR$^7$R$^8$;

Y is selected from oxy (—O—), thio (—S—), sulfinyl (—SO—), sulfonyl (—S(O)$_2$—) and amine-N(R$^9$) —;

R$^6$ is selected from H, (C$_1$-C$_8$)alkyl, R$^a$O(C$_1$-C$_8$)alkyl, R$^b$R$^c$N(C$_1$-C$_8$)alkyl, halo(C$_1$-C$_8$)alkyl, (C$_3$-C$_6$)cycloalkyl, (C$_3$-C$_6$)cycloalky(C$_1$-C$_4$)alkyl-, (C$_3$-C$_{10}$)heterocycle, (C$_3$-C$_{10}$)heterocycle(C$_1$-C$_8$)alkyl-, (C$_6$-C$_{10}$)aryl, (C$_6$-C$_{10}$)aryl(C$_1$-C$_8$)alkyl-, (C$_4$-C$_{10}$)heteroaryl and (C$_4$-C$_{10}$)heteroaryl(C$_1$-C$_8$)alkyl-;

R$^7$, R$^8$ and R$^9$ are independently selected from H, (C$_1$-C$_8$)alkyl, R$^a$O(C$_1$-C$_8$)alkyl, R$^b$R$^c$N(C$_1$-C$_8$)alkyl, halo(C$_1$-C$_8$)alkyl, (C$_3$-C$_{10}$)heterocycle, (C$_6$-C$_{10}$)aryl, (C$_6$-C$_{10}$)aryl(C$_1$-C$_8$)alkyl-, (C$_4$-C$_{10}$)heteroaryl; —COOR$^a$, —C(O)R$^a$ and —C(O)NR$^b$R$^c$;

alternatively, R$^7$ and R$^8$ together with the atoms to which they are attached, form a saturated or partially unsaturated, mono-, bicyclic- or aromatic ring having 3, 4, 5, 6, 7 or 8 ring atoms and there optionally being 1, 2, 3, or 4 heteroatoms selected from non-peroxide oxy (—O—), thio (—S—), sulfinyl (—SO—), sulfonyl (—S(O)$_2$—) or amine —N(R$^b$)-in the ring;

wherein the alkyl, alkenyl, cycloalkyl, alkynyl, aryl, heterocycle or heteroaryl groups of R$^1$, R$^2$, R$^4$, R$^5$, R$^6$, R$^7$, R$^8$ and R$^9$ are optionally substituted with one or more substituents independently selected from halo, cyano, nitro, —OR$^a$, —SR$^a$, (C$_1$-C$_8$)alkyl, (C$_6$-C$_{10}$)aryl, —O(C$_6$-C$_{10}$)aryl, hydroxy(C$_1$-C$_8$)alkyl, R$^b$R$^c$N(C$_1$-C$_8$)alkyl, halo(C$_1$-C$_8$)alkyl, —NR$^b$R$^c$, —C(O)R$^a$, —COOR$^a$ and —C(O)NR$^b$R$^c$;

R$^a$ is selected from H, and (C$_1$-C$_6$)alkyl;

R$^b$ and R$^c$ are each independently selected from H, (C$_1$-C$_6$)alkyl, (C$_1$-C$_6$)alkoxy, (C$_3$-C$_8$)cycloalkyl, C$_1$-C$_6$)alkylthio, (C$_6$-C$_{10}$)aryl, (C$_6$-C$_{10}$)aryl(C$_1$-C$_6$)alkyl-, heteroaryl and heteroaryl(C$_1$-C$_6$)alkyl-;

alternatively, R$^b$ and R$^c$ together with the nitrogen to which they are attached, form a ring selected from pyrrolidyl, piperidyl, piperazinyl, azepinyl, diazepinyl, morpholinyl and thiomorpholinyl;

m is independently selected from 1 and 2; and, q is independently selected from 1, 2, 3 and 4.

2. The method of claim 1, wherein the compound is selected from:

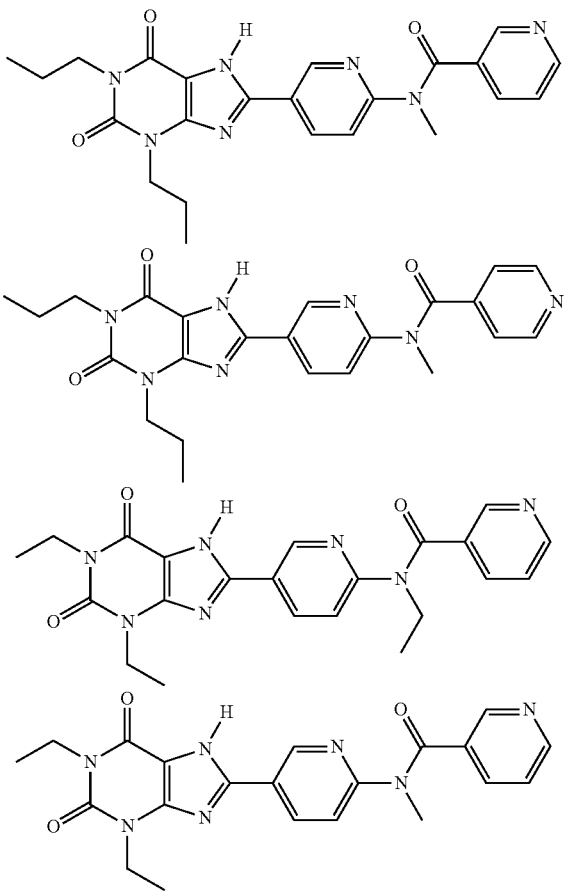

-continued

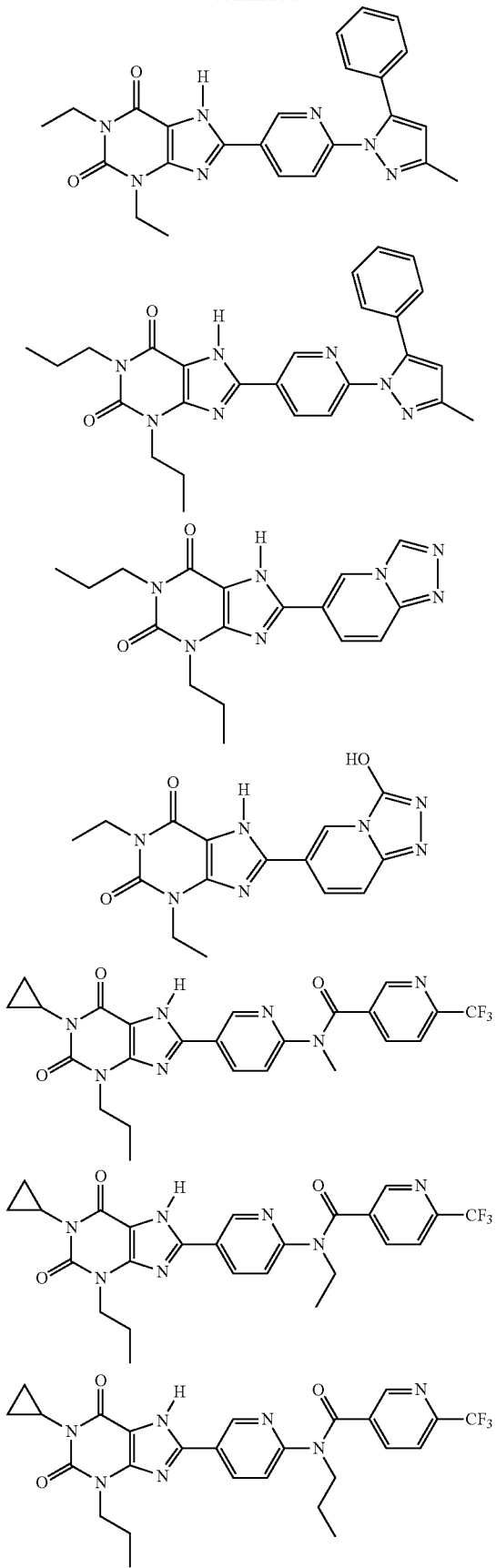
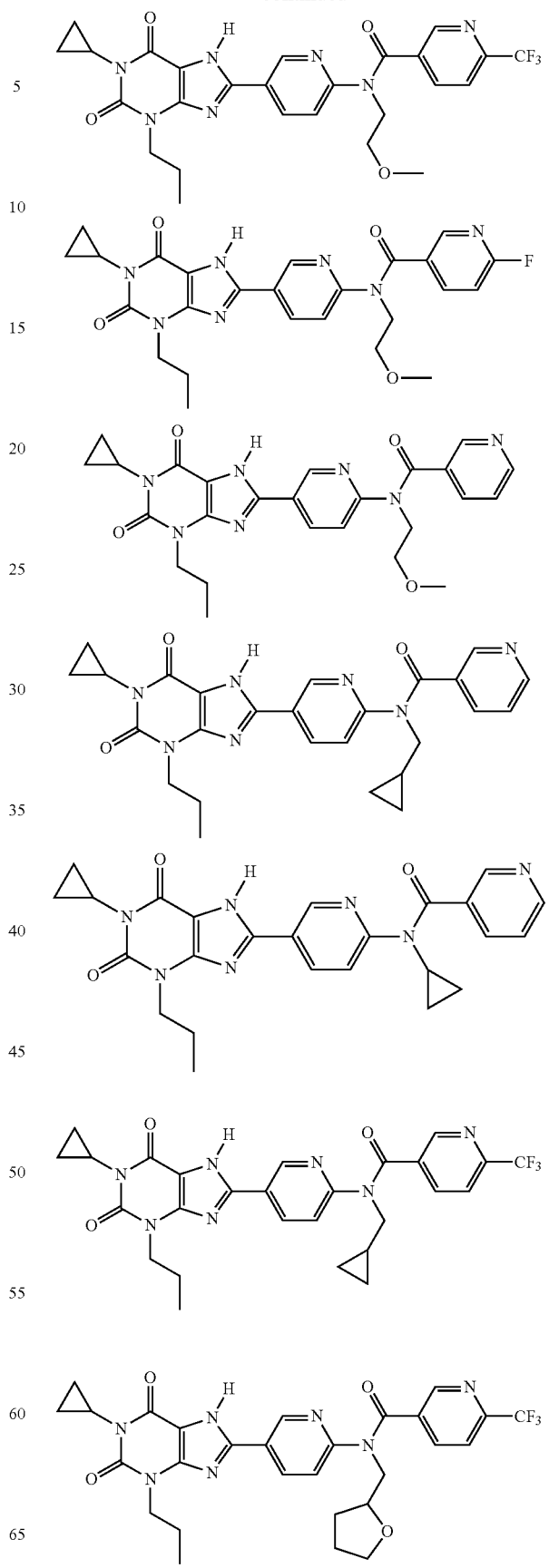

55
-continued
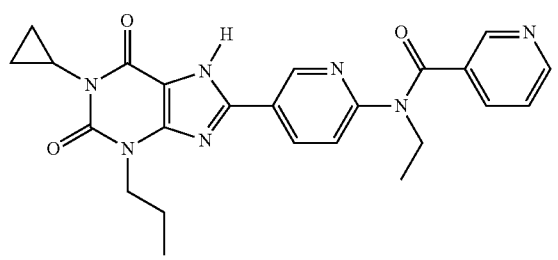
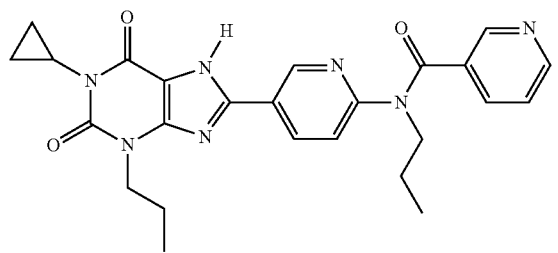
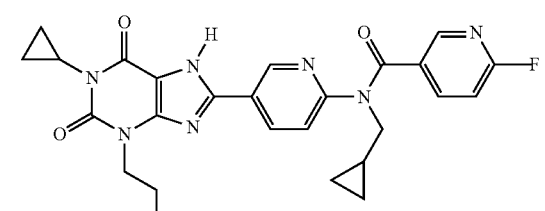
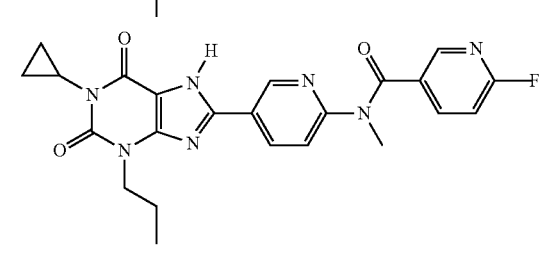
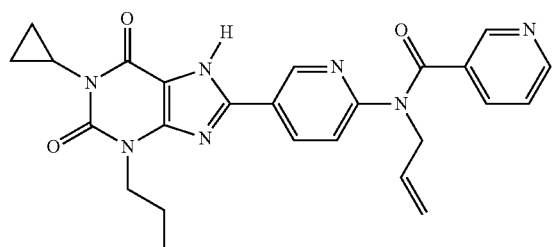
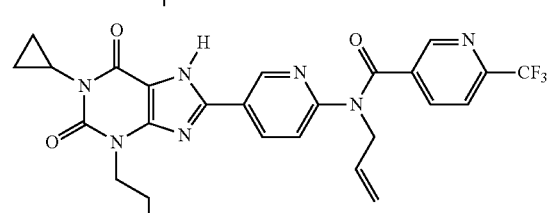
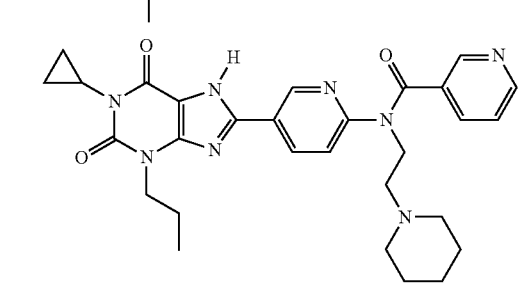
56
-continued
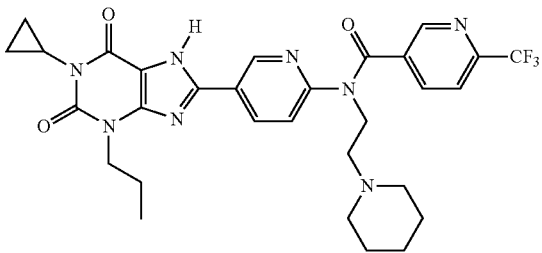
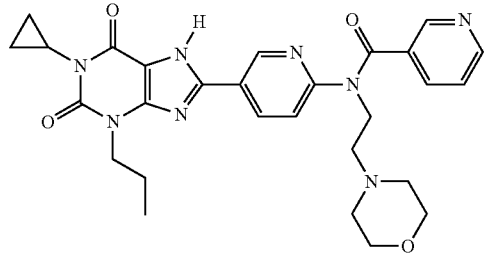
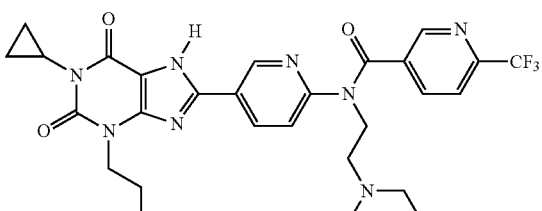
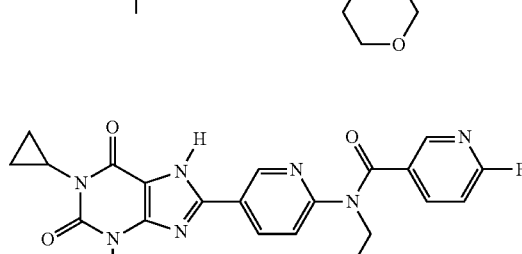
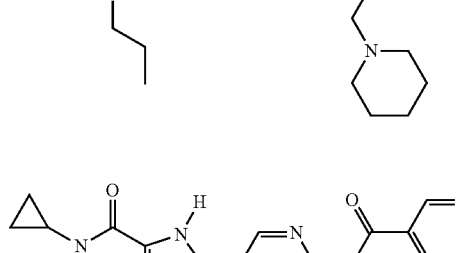
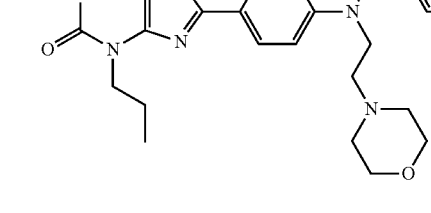
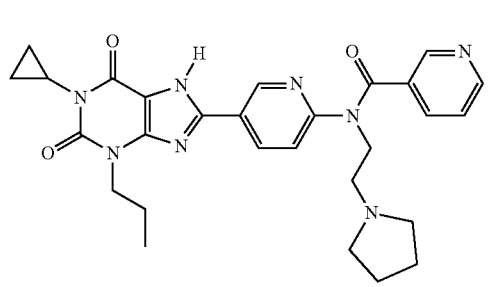

57
-continued
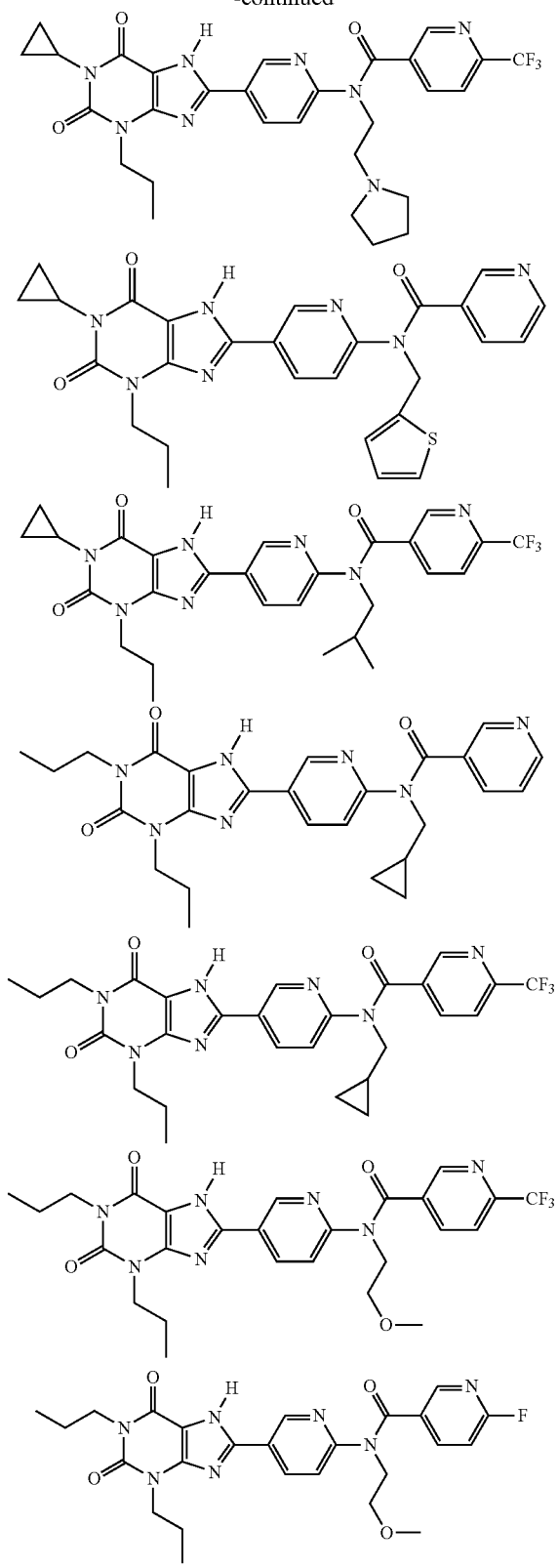
58
-continued
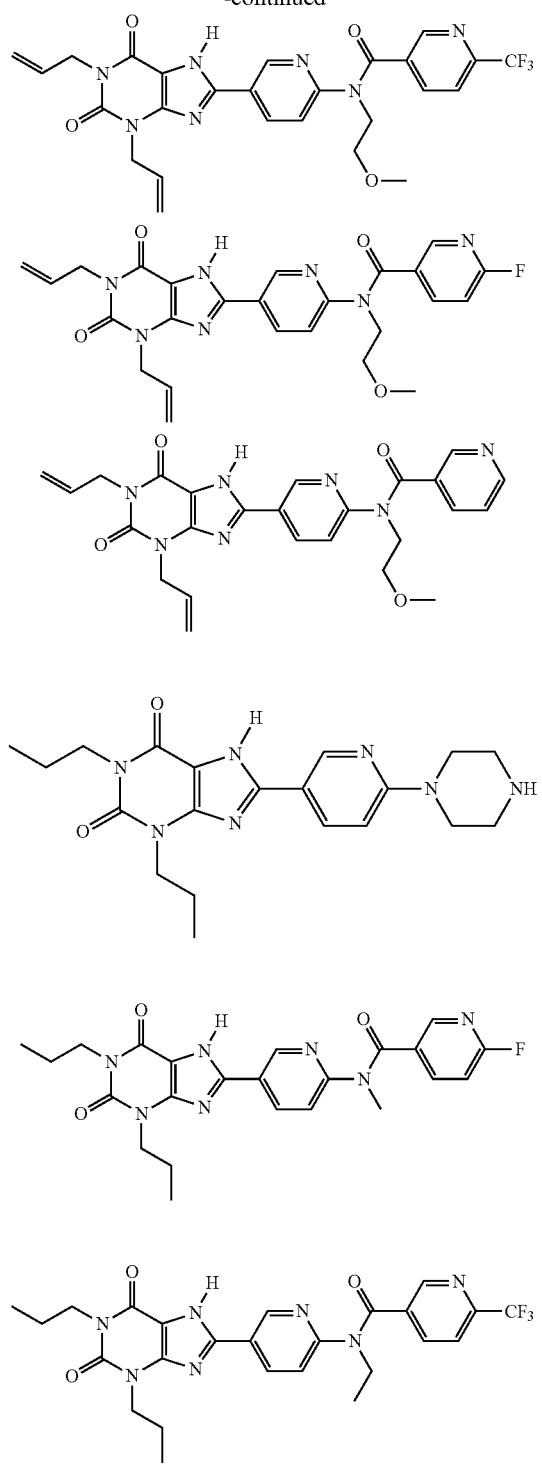
and a pharmaceutically acceptable salt thereof.
* * * * *